(12) United States Patent
Bejot et al.

(10) Patent No.: US 12,036,290 B2
(45) Date of Patent: Jul. 16, 2024

(54) PHARMACEUTICAL FORMULATIONS

(71) Applicants: Blue Earth Diagnostics Limited, Oxford (GB); Siemens Medical Solutions USA, Inc., Malvern, PA (US)

(72) Inventors: Romain Bejot, Oxford (GB); Michael Haka, Knoxville, TN (US); Atilio Anzellotti, Oak Ridge, TN (US)

(73) Assignees: Blue Earth Diagnostics Limited, Oxford (GB); Siemens Medical Solutions USA, Inc., Malvern, PA (US)

(*) Notice: Subject to any disclaimer, the term of this patent is extended or adjusted under 35 U.S.C. 154(b) by 232 days.

(21) Appl. No.: 17/226,848

(22) Filed: Apr. 9, 2021

(65) Prior Publication Data
US 2021/0322581 A1 Oct. 21, 2021

(30) Foreign Application Priority Data

Apr. 9, 2020 (GB) .................................... 2005282

(51) Int. Cl.
| | | |
|---|---|---|
| A61K 51/04 | (2006.01) | |
| A61K 47/02 | (2006.01) | |
| A61K 47/10 | (2017.01) | |
| A61K 47/12 | (2006.01) | |

(52) U.S. Cl.
CPC ............ A61K 51/044 (2013.01); A61K 47/02 (2013.01); A61K 47/10 (2013.01); A61K 47/12 (2013.01); A61K 51/0489 (2013.01)

(58) Field of Classification Search
CPC ............ A61K 51/0497; A61K 51/0402; A61K 51/0482
See application file for complete search history.

(56) References Cited

U.S. PATENT DOCUMENTS

2019/0192660 A1    6/2019  Romoren et al.

FOREIGN PATENT DOCUMENTS

| | | | | |
|---|---|---|---|---|
| CN | 102626522 | A | 8/2012 | |
| CN | 106794264 | A | 5/2017 | |
| EP | 1356827 | A1 * | 10/2003 | ............ A61K 51/04 |
| EP | 1356827 | A1 | 10/2003 | |
| EP | 3636635 | A1 | 4/2020 | |
| JP | 2005519861 | A | 7/2005 | |
| WO | 9501346 | A1 | 1/1995 | |
| WO | 2004/043497 | A1 | 5/2004 | |
| WO | 2013/093025 | A1 | 6/2013 | |
| WO | 2015/118498 | A1 | 8/2015 | |
| WO | 2016062370 | A1 | 4/2016 | |
| WO | 2019/020831 | A1 | 1/2019 | |
| WO | WO-2019020831 | A1 * | 1/2019 | ......... A61K 51/0402 |
| WO | 2019/145293 | A1 | 8/2019 | |
| WO | 2020157128 | A1 | 8/2020 | |
| WO | 2020157177 | A1 | 8/2020 | |
| WO | 2020157184 | A1 | 8/2020 | |
| WO | 2020220020 | A1 | 10/2020 | |
| WO | 2020252598 | A1 | 12/2020 | |
| WO | 2021205185 | A1 | 10/2021 | |
| WO | 2022144463 | A1 | 7/2022 | |
| WO | 2022144467 | A1 | 7/2022 | |
| WO | 2022171869 | A1 | 8/2022 | |
| WO | 2022171901 | A1 | 8/2022 | |

OTHER PUBLICATIONS

Great Britain Search Report for Application No. GB2005282.5, dated Oct. 19, 2020, 2 pages.
Jacobson et al., Radiolysis of 2-[18F]fluoro-2-deoxy-D-glucose ([18F]FDG) and the role of ethanol and radioactive concentration. Appl Radiat Isot. Jun. 2009;67(6):990-5.
Wurzer et al., Radiohybrid Ligands: A Novel Tracer Concept Exemplified by 18F- or 68Ga-Labeled rhPSMA Inhibitors. J Nucl Med. May 2020;61(5):735-742.
International Search Report and Written Opinion for Application No. PCT/GB2021/050877, dated Jul. 12, 2021, 18 pages.
Silver et al., "Prostate-specific membrane antigen expression in normal and malignant human tissues", Clinical Cancer Research, vol. 3, No. 1, pp. 81-85, Jan. 1997.
Afshar-Oromieh et al., "The diagnostic value of PET/CT imaging with the (68)Ga-labelled PSMA ligand HBED-CC in the diagnosis of recurrent prostate", European Journal of Nuclear Medicine and Molecular Imaging, vol. 42, No. 2, pp. 197-209, Feb. 2015.
Benesova et al., "Preclinical Evaluation of a Tailor-Made DOTA-Conjugated PSMA Inhibitor with Optimized Linker Moiety for Imaging and Endoradiotherapy of Prostate Cancer", Journal of Nuclear Medicine, vol. 56, No. 6, pp. 914-620, Jun. 2015.
Robu et al., "Preclinical Evaluation and First Patient Application of 99mTc-PSMA-I&S for SPECT Imaging and Radioguided Surgery in Prostate Cancer", Journal of Nuclear Medicine, vol. 58, No. 2, pp. 235-242, Feb. 2017.
Weineisen et al., "Development and first in human evaluation of Psma I&T: A ligand for diagnostic imaging and endoradiotherapy of prostate cancer", Journal of Nuclear Medicine, vol. 55, No. 1, p. 1083, May 2014.
Rowe et al., "PET imaging of prostate-specific membrane antigen in prostate cancer: current state of the art and future challenges", Prostate Cancer and Prostatic Diseases, vol. 19, No. 3, pp. 223-230, Sep. 2016.
Maurer et al., "Current use of PSMA-PET in prostate cancer management", Nature Reviews Urology, vol. 13, No. 4, pp. 226-235, Apr. 2016.
Zhou et al., "NAAG peptidase inhibitors and their potential for diagnosis and therapy", Nature Reviews Drug Discovery, vol. 4, pp. 1015-1026, Dec. 2005.
Machulkin et al., "Small-molecule PSMA ligands. Current state, SAR and perspectives", Journal of Drug Targeting, vol. 24, No. 8, pp. 679-693, Sep. 2016.

(Continued)

Primary Examiner — Micah Paul Young
(74) Attorney, Agent, or Firm — Bookoff McAndrews, PLLC

(57) ABSTRACT

The present invention relates to a pharmaceutical composition comprising a radiohybrid agent containing a silicon-fluoride and a chelating group wherein either the fluorine is $^{18}$F or the chelating group contains a chelated radioactive metal, wherein the composition has a pH of 4.0-6.0 and further comprises: 0.1-200 mM citrate buffer; 1-100 mg/mL ethanol; and 5-10 mg/mL sodium chloride.

20 Claims, No Drawings

(56) References Cited

OTHER PUBLICATIONS

Barinka et al., "Interactions between Human Glutamate Carboxypeptidase II and Urea-Based Inhibitors: Structural Characterization", vol. 51, No. 24, pp. 7737-7743, Dec. 2008.
Zhang et al., "A Remote Arene-Binding Site on Prostate Specific Membrane Antigen Revealed by Antibody-Recruiting Small Molecules", Journal of American Chemical Society, vol. 132, No. 36, pp. 12711-12716, Sep. 1, 2010.
Liu et al., "Spacer length effects on in vitro imaging and surface accessibility of fluorescent inhibitors of prostate specific membrane antigen", Bioorganic & Medicinal Chemistry Letters, vol. 21, No. 23, pp. 7013-7016, Dec. 2011.
Kiess et al., "Prostate-specific membrane antigen as a target for cancer imaging and therapy ", The Quarterly Journal of Nuclear Medicine and Molecular Imaging, vol. 59, No. 3, pp. 241-268, Sep. 2015.
Eder et al., "68Ga-complex lipophilicity and the targeting property of a urea-based PSMA inhibitor for PET imaging ", Bioconjugate Chemistry, vol. 23, No. 4, pp. 688-697, Apr. 18, 2012.
Rowe et al., "PSMA-Based [(18)F]DCFPyL PET/CT Is Superior to Conventional Imaging for Lesion Detection in Patients with Metastatic Prostate Cancer", Molecular Imaging and Biology, vol. 18, No. 3, pp. 411-419, Jun. 1, 2016.
Dietlein et al., "Comparison of [(18)F]DCFPyL and [ (68)Ga]Ga-PSMA-HBED-CC for PSMA-PET Imaging in Patients with Relapsed Prostate Cancer", Molecular Imaging and Biology, vol. 17, No. 4, pp. 575-584, Aug. 2015.
Cardinale et al., "Preclinical Evaluation of 18F-PSMA-1007, a New Prostate-Specific Membrane Antigen Ligand for Prostate Cancer Imaging", Journal of Nuclear Medicine, vol. 58, No. 3, pp. 425-431, Mar. 2017.
Giesel et al., "18F-Labelled PSMA-1007 shows similarity in structure, biodistribution and tumour uptake to the theragnostic compound PSMA-617", European Journal of Nuclear Medicine and Molecular Imaging, vol. 43, pp. 1929-1930, May 2016.
Giesel et al., "1F-18 labelled PSMA-1007: biodistribution, radiation dosimetry and histopathological validation of tumor lesions in prostate cancer patients", European Journal of Nuclear Medicine and Molecular Imaging, vol. 44, No. 7, pp. 678-688, Apr. 2017.
Lindner et al., "Synthesis and in Vitro and in Vivo Evaluation of SiFA-Tagged Bombesin and RGD Peptides as Tumor Imaging Probes for Positron Emission Tomography", Bioconjugate Chemistry, vol. 25, No. 4, pp. 738-749, Mar. 25, 2014.
Schirmacher et al., "Synthesis of p-(Di-tert-butyl[18F]fluorosilyl)benzaldehyde ([18F]SiFA-A) with High Specific Activity by Isotopic Exchange: A Convenient Labeling Synthon for the 18F-Labeling of N-amino-oxy Derivatized Peptides", Bioconjugate Chemistry, vol. 18, No. 6, pp. 2085-2089, Nov. 21, 2007.
Wangler et al., "Kit-Like 18F-Labeling of Proteins: Synthesis of 4-(Di-tert-butyl[18F]fluorosilyl)benzenethiol (Si[18F]FA-SH) Labeled Rat Serum Albumin for Blood Pool Imaging with PET", Bioconjugate Chemistry, vol. 20, No. 2, pp. 317-321, Jan. 8, 2009.
Wangler et al., "One-step 18F-labeling of carbohydrate-conjugated octreotate-derivatives containing a silicon- fluoride-acceptor (SiFA): in vitro and in vivo evaluation as tumor imaging agents for positron emission tomography (PET)", Bioconjugate Chemistry, vol. 21, No. 12, pp. 2289-2296, Dec. 15, 2010.
Bernard-Gauthier et al., "18F-labeled silicon-based fluoride acceptors: potential opportunities for novel positron emitting radiopharmaceuticals", BioMed Research International, vol. 2014, 20 pages, Jul. 2014.
Niedermoser et al., "In Vivo Evaluation of 18F-SiFAlin-Modified Tate: A Potential Challenge for 68Ga-DOTATATE, the Clinical Gold Standard for Somatostatin Receptor Imaging with PET", Journal of Nuclear Medicine, vol. 56, No. 7, pp. 1100-1105, Jul. 2015.
Notni et al., "A Triazacyclononane-Based Bifunctional Phosphinate Ligand for the Preparation of Multimeric 68Ga Tracers for Positron Emission Tomography", Chemistry - A European Journal, vol. 16, No. 24, pp. 7174-7185, May 2010.
Iovkova et al., "para-Functionalized aryl-di-tert-butylfluorosilanes as potential labeling synthons for (18)F radiopharmaceuticals", Chemistry - A European Journal, vol. 15, No. 9, pp. 2140-2147, 2009.
Weineisen et al., "Synthesis and preclinical evaluation of DOTAGA-conjugated PSMA ligands for functional imaging and endoradiotherapy of prostate cancer", EJNMMI Research, vol. 4, No. 63, Dec. 2014.
Reich et al., "Dendritic poly-chelator frameworks for multimeric bioconjugationt", Chemical Communications, vol. 53, pp. 2586-2589, Feb. 2017.
Notni et al., "Comparative gallium-68 labeling of Trap-, NOTA-, and DOTA-peptides: Practical consequences for the future of gallium-68-PET", EJNMMI Research, vol. 2, No. 28, 5 pages, Jun. 2012.
Wangler et al., "One-step (18)F-labeling of peptides for positron emission tomography imaging using the SiFA methodology", Nature Portfolio, vol. 7, No. 11, pp. 1946-1955, Nov. 2012.
Bouaziz et al., "Toxic Effects of Fluoride by Maternal Ingestion on Kidney Function of Adult Mice and Their Suckling Pups", Fluoride Research, vol. 38, No. 1, pp. 23-31, 2005.
Poesina et al., "Histopathological changes of renal tissue following sodium fluoride administration in two consecutive generations of mice. Correlation with the urinary elimination of fluoride", Romanian Journal of Morphology and Embryology, vol. 55, No. 2, pp. 343-349, 2014.
Inkielewicz et al., "Fluoride Content in Soft Tissues and Urine of Rats Exposed to Sodium Fluoride in Drinking Water", Fluoride Research, vol. 36, No. 4, pp. 263-266, 2003.
Eiber et al., "18F-rhPSMA-7 PET for the Detection of Biochemical Recurrence of Prostate Cancer After Radical Prostatectomy", Journal of Nuclear Medicine, vol. 61, No. 5, pp. 696-701, May 2020.
Oh et al., "Quantitative and Qualitative Analyses of Biodistribution and PET Image Quality of a Novel Radiohybrid PSMA, 18F-rhPSMA-7, in Patients with Prostate Cancer", Journal of Nuclear Medicine, vol. 61, No. 5, pp. 702-709, May 2020.
Kostikov et al., "Oxalic acid supported Si-18F-radiofluorination: one-step radiosynthesis of N-succinimidyl 3-(di-tert-butyl[18F]fluorosilyl)benzoate ([18F]SiFB) for protein labeling", Bioconjugate Chemistry, vol. 23, No. 1, Jan. 18, 2012.
Wurzer et al., "Automated synthesis of [18F]Ga-rhPSMA-7/ -7.3: results, quality control and experience from more than 200 routine productions", EJNMMI Radiopharmacy and Chemistry, vol. 6, No. 4, 15 pages, Jan. 23, 2021.
Sartor et al., "Lutetium-177-PSMA-617 for Metastatic Castration-Resistant Prostate Cancer", New England Journal of Medicine, vol. 385, No. 12, pp. 1091-1103, Sep. 16, 2021.
Wurzer et al., "Synthesis and Preclinical Evaluation of 177Lu-Labeled Radiohybrid PSMA Ligands for Endoradiotherapy of Prostate Cancer", Journal of Nuclear Medicine, vol. 63, No. 10, pp. 1489-1495, Oct. 2022.
Foxton et al., "Preclinical evaluation of a novel radioligand therapy for patients with prostate cancer: biodistribution and efficacy of 177Lu-rhPSMA-10.1 in comparison with 177Lu-PSMA-I&T", Journal of Nuclear Medicine, vol. 63, No. 2, 4 pages, Jun. 2022.
Bundschuh et al., "177 Lu-rhPSMA-10.1 Induces Tumor Response in a Patient With mCRPC After PSMA-Directed Radioligand Therapy With 177 Lu-PSMA-I&T", Clinical Nuclear Medicine, vol. 48, No. 4, pp. 337-338, Apr. 1, 2023.
Litau et al., "Next Generation of SiFAlin-Based TATE Derivatives for PET Imaging of SSTR-Positive Tumors: Influence of Molecular Design on In Vitro SSTR Binding and In Vivo Pharmacokinetics", Bioconjugate Chemistry, vol. 26, No. 12, pp. 2350-2359, Sep. 30, 2015.
Bernard-Gauthier et al., "From Unorthodox to Established: The Current Status of 18F-Trifluoroborate- and 18F- SiFA-Based Radiopharmaceuticals in PET Nuclear Imaging", Bioconjugate Chemistry, vol. 27, No. 2, pp. 267-279, 2016.
Carroll et al., "Orthogonal 18F and 64Culabelling of functionalised bis(thiosemicarbazonato) complexes+", Chemical Communications, vol. 46, No. 23, pp. 4052-4054, Jun. 21, 2010.

(56) References Cited

OTHER PUBLICATIONS

Hueting et al., "A dual radiolabelling approach for tracking metal complexes: investigating the speciation of copper bis(thiosemicarbazonates) in vitro and in vivo", Metallomics, vol. 7, No. 5, pp. 795-804, May 2015.

Westerlund et al., "Increasing the Net Negative Charge by Replacement of DOTA Chelator with DOTAGA Improves the Biodistribution of Radiolabeled Second-Generation Synthetic Affibody Molecules", Molecular Pharmaceutics, vol. 13, No. 5, pp. 1668-1678, Mar. 23, 2016.

Banerjee et al., "Sequential SPECT and Optical Imaging of Experimental Models of Prostate Cancer with a Dual Modality Inhibitor of the Prostate-Specific Membrane Antigent", Angewandte Chemie, vol. 123, No. 39, pp. 9333-9336, Sep. 19, 2011.

Lutje et al., "PSMA Ligands for Radionuclide Imaging and Therapy of Prostate Cancer: Clinical Status", Theranostics, vol. 5, No. 12, pp. 1388-13401, Oct. 18, 2015.

Bailey et al., "Silicon/Fluorine-18/PSMA: A winning team for PET imaging of prostate cancer", Journal of Labelled Compounds and Radiopharmaceuticals Journal, 1 page, May 1, 2017.

Ghesquiere et al., "Metabolism of stromal and immune cells in health and disease", Nature, vol. 511, pp. 167-176, Jul. 10, 2014.

Wurzer et al., "Preclinical comparison of four [18F, natGa]rhPSMA-7 isomers: influence of the stereoconfiguration on pharmacokinetics", EJNMMI Research, vol. 10, No. 1, 10 pages, Dec. 7, 2020.

Kozikowski et al., "Synthesis of urea-based inhibitors as active site probes of glutamate carboxypeptidase II: efficacy as analgesic agents", Journal of Medicinal Chemistry, vol. 47, No. 7, pp. 1729-1738, Mar. 25, 2004.

Plechanovava et al., "Novel Substrate-Based Inhibitors of Human Glutamate Carboxypeptidase II with Enhanced Lipophilicity", Journal of Medicinal Chemistry, vol. 54, No. 21, pp. 7535-7546, Sep. 19, 2011.

Barinka et al., "Substrate specificity, inhibition and enzymological analysis of recombinant human glutamate carboxypeptidase II", Journal of Neurochemistry, vol. 80, No. 4, pp. 477-487, Feb. 2002.

Wang et al., "Bioisosterism of urea-based GCPII inhibitors: Synthesis and structure-activity relationship studies", Bioorganic & Medicinal Chemistry Letters, vol. 20, No. 1, pp. 392-397, Jan. 1, 2010.

Pavlicek et al., "Structural characterization of P1'-diversified urea-based inhibitors of glutamate carboxypeptidase II", Bioorganic & Medicinal Chemistry Letters, vol. 24, No. 10, pp. 2340-2345, May 15, 2014.

\* cited by examiner

PHARMACEUTICAL FORMULATIONS

This application claims priority to GB Application No.: 2005282.5, filed Apr. 9, 2020, the entire contents of which are incorporated herein by reference.

The present invention relates to a pharmaceutical composition of a radiohybrid agent containing a silicon-fluoride and a chelating group wherein either the fluorine is fluorine-18 ($^{18}$F) or the chelating group contains a chelated radioactive metal. The composition has a pH of 4.0-6.0 and further comprises: 0.1-200 mM citrate buffer; and 1-100 mg/mL ethanol; and 5-10 mg/mL sodium chloride.

Prostate Cancer

Prostate Cancer (PCa) remained over the last decades the most common malignant disease in men with high incidence for poor survival rates. Due to its overexpression in prostate cancer, prostate-specific membrane antigen (PSMA) or glutamate carboxypeptidase II (GCP II) proved its eligibility as excellent target for the development of highly sensitive radiolabelled agents for endoradiotherapy and imaging of PCa. Prostate-specific membrane antigen is an extracellular hydrolase whose catalytic center comprises two zinc(II) ions with a bridging hydroxido ligand. It is highly upregulated in metastatic and hormone-refractory prostate carcinomas, but its physiologic expression has also been reported in kidneys, salivary glands, small intestine, brain and, to a low extent, also in healthy prostate tissue. In the intestine, PSMA facilitates absorption of folate by conversion of pteroylpoly-γ-glutamate to pteroylglutamate (folate). In the brain, it hydrolyses N-acetyl-L-aspartyl-L-glutamate (NAAG) to N-acetyl-L-aspartate and glutamate.

Prostate-Specific Membrane Antigen (PSMA)

Prostate-specific membrane antigen (PSMA) is a type II transmembrane glycoprotein that is highly overexpressed on prostate cancer epithelial cells. Despite its name, PSMA is also expressed, to varying degrees, in the neovasculature of a wide variety of non-prostate cancers. Among the most common non-prostate cancers to demonstrate PSMA expression include breast, lung, colorectal, and renal cell carcinoma.

The general necessary structures of PSMA targeting molecules comprise a binding unit that encompasses a zinc-binding group (such as urea, phosphinate or phosphoramidate) connected to a P1' glutamate moiety, which warrants high affinity and specificity to PSMA and is typically further connected to an effector functionality. The effector part is more flexible and to some extent tolerant towards structural modifications.

Two categories of PSMA targeting inhibitors are currently used in clinical settings. On the one side there are tracers with chelating units for radionuclide complexation such as PSMA I&T or related compounds. On the other side there are small molecules, comprising a targeting unit and effector molecules.

$^{18}$F Labelling

Recently, several groups have focused on the development of novel $^{18}$F-labelled urea-based inhibitors for PCa diagnosis. The $^{18}$F-labelled urea-based PSMA inhibitor $^{18}$F-DCFPyl demonstrated promising results in the detection of primary and metastatic PCa. Based on the structure of PSMA-617, the $^{18}$F-labelled analogue PSMA-1007 was recently developed, which showed comparable tumor-to-organ ratios.

An attractive approach for introducing $^{18}$F labels is the use of silicon-fluoride acceptors (SIFA). Silicon-fluoride acceptors are described, for example, in Lindner et al., Bioconjugate Chemistry 25, 738-749 (2014). In order to preserve the silicon-fluoride bond, the use of silicon-fluoride acceptors introduces the necessity of sterically demanding groups around the silicon atom. This in turn renders silicon-fluoride acceptors highly hydrophobic. In terms of binding to the target molecule, in particular to the target molecule which is PSMA, the hydrophobic moiety provided by the silicon-fluoride acceptor may be exploited for the purpose of establishing interactions of the radio-diagnostic or -therapeutic compound with the hydrophobic pocket described in Zhang et al., Journal of the American Chemical Society 132, 12711-12716 (2010). Yet, prior to binding, the higher degree of lipophilicity introduced into the molecule poses a severe problem with respect to the development of radiopharmaceuticals with suitable in vivo biodistribution, i.e. low unspecific binding in non-target tissue.

Despite many attempts, the hydrophobicity problem caused by silicon-fluoride acceptors has only recently been solved by the use of agents having a hydrophilic chelator moiety. Application WO2019/020831 describes a new type of radio-hybrid agent having both a SIFA moiety and a metal chelator. In developing the compounds described therein the inventors have identified improved pharmaceutical formulations for patient delivery. The formulations described herein show improved radio-stability and shelf-life over previously described formulations.

In view of the above, the technical problem underlying the present invention can be seen in providing improved radio-diagnostic formulations which contain a silicon-fluoride acceptor and a metal chelator which are, at the same time, characterized by favourable pharmaco-stability properties.

SUMMARY OF THE INVENTION

As will be become apparent in the following, the present invention established a proof-of-principle using specific conjugates, formulated in specific ways, which bind with high affinity to prostate-specific antigen (PSMA) as target. The composition in which the compounds are prepared and stored affects the chemical and radiochemical stability of the agents. Accordingly, a further technical problem underlying the present invention can be seen in providing improved diagnostics for the medical indication which is cancer, preferably prostate cancer.

These technical problems are solved by the subject-matter of the claims. Accordingly, in the first aspect, the present invention relates to a pharmaceutical composition comprising a radiohybrid agent containing a silicon-fluoride and a chelating group wherein either the fluorine is fluorine-18 ($^{18}$F) or the chelating group contains a chelated radioactive metal wherein the composition has a pH of 4.0-6.0 and further comprises:

(a) 0.1-200 mM citrate buffer; and
(b) 1-100 mg/mL ethanol; and
(c) 5-10 mg/mL sodium chloride.

Alternative compositions that are disclosed herein relate to pharmaceutical compositions of a radiohybrid agent containing a silicon-fluoride and a chelating group wherein either the fluorine is $^{18}$F or the chelating group contains a chelated radioactive metal wherein the composition comprises: (a) 50-200 mM citrate buffer and/or; (b) 10-100 mg/mL ethanol and/or; (c) has a pH of 4.0-6.0.

The formulation may be prepared in a high concentration of citrate buffer, then diluted to lower the citrate concentration. The ethanol concentration may also be lowered by dilution. The composition may be diluted with a solution containing sodium chloride (saline).

Described is a method of producing a composition as described herein, the method comprising preparing a formulation of a radiohybrid agent containing a silicon-fluoride and a chelating group wherein either the fluorine is $^{18}$F or the chelating group contains a chelated radioactive metal, wherein the composition has a pH of 4.0-6.0 and a citrate concentration of at least 10 mM, and diluting the citrate concentration with a solution of sodium chloride.

The pharmaceutical composition may comprise 50-200 mM citrate buffer.

The pharmaceutical composition may comprise 10-100 mg/ml ethanol.

The pharmaceutical composition may have a pH of 4.0 to 6.0.

The pharmaceutical composition may comprise a chelated radioactive metal or an $^{18}$F fluorine.

The pharmaceutical composition may comprise a chelated radioactive metal selected from the cations of: Sc, Cu, Ga, Y, In, Tb, Ho, Lu, Re, Pb, Ac, Th or Er.

The pharmaceutical composition may comprise an $^{18}$F fluorine and a non-radioactive chelated metal ion.

The pharmaceutical composition may comprise $^{19}$F fluorine and a radioactive chelated metal ion.

The pharmaceutical composition may be a composition wherein the metal is radioactive and the fluorine is $^{19}$F.

The pharmaceutical composition may be a composition wherein the fluorine is $^{18}$F and the metal is non-radioactive.

The pharmaceutical composition may comprise a chelated radioactive metal cation selected from: $^{177}$Lu, $^{90}$Y, $^{225}$Ac, $^{68}$Ga or $^{67}$Ga.

The pharmaceutical composition may comprise 60-120 mM citrate buffer.

The pharmaceutical composition may comprise 0.1-200 mM citrate buffer.

The pharmaceutical composition may comprise 0.1-120 mM citrate buffer.

The pharmaceutical composition may comprise 0.1-50 mM citrate buffer.

The pharmaceutical composition may comprise 0.1-20 mM citrate buffer. The pharmaceutical composition may comprise 1-15 mM citrate buffer.

The pharmaceutical composition may comprise 10 mM (±15%) citrate buffer.

The pharmaceutical composition may comprise 10 mM (±10%) citrate buffer.

The pharmaceutical composition may comprise 10 mM (±5%) citrate buffer.

The pharmaceutical composition may comprise 10 mM (±2%) citrate buffer.

The pharmaceutical composition may comprise 10 mM (±1%) citrate buffer.

The pharmaceutical composition may comprise 10 mM citrate buffer.

The pharmaceutical composition may comprise 1-10 mM citrate buffer.

The pharmaceutical composition may comprise 1-10 mM (±15%) citrate buffer.

The pharmaceutical composition may comprise 1-10 mM (±10%) citrate buffer.

The pharmaceutical composition may comprise 1-10 mM (±5%) citrate buffer.

The pharmaceutical composition may comprise 1-10 mM (±2%) citrate buffer.

The pharmaceutical composition may comprise 1-10 mM (±1%) citrate buffer.

The pharmaceutical composition may be formulated with anhydrous citric acid or alternatively citric acid monohydrate, or salts thereof (including sodium citrate). The pharmaceutical composition may be formulated using citric acid monohydrate.

The pharmaceutical composition may be formulated with 1.5-2.5 mg/mL citric acid (anhydrous basis).

The pharmaceutical composition may be formulated with 1.9 mg/mL (±10%) citric acid (anhydrous basis).

The pharmaceutical composition may be formulated with 1.9 mg/mL (±5%) citric acid (anhydrous basis).

The pharmaceutical composition may be formulated with 1.9 mg/mL (±2%) citric acid (anhydrous basis).

The pharmaceutical composition may be formulated with 1.9 mg/mL (±1%) citric acid (anhydrous basis).

The pharmaceutical composition may be formulated with 1.9 mg/mL citric acid (anhydrous basis).

The pharmaceutical composition may have a pH of 4.5-5.5.

The pharmaceutical composition may have a pH of 5 (±15%).

The pharmaceutical composition may have a pH of 5 (±10%).

The pharmaceutical composition may have a pH of 5 (±5%).

The pharmaceutical composition may have a pH of 5 (±2%).

The pharmaceutical composition may have a pH of 5 (±1%).

The pharmaceutical composition may have a pH of 5.

The pharmaceutical composition may have a pH of 5.1.

The pharmaceutical composition may have a pH of 4.9.

The pharmaceutical composition may comprise 5-100 mg/mL ethanol.

The pharmaceutical composition may comprise 10-100 mg/mL ethanol.

The pharmaceutical composition may comprise 10-70 mg/mL ethanol.

The pharmaceutical composition may comprise 40-60 mg/mL ethanol.

The pharmaceutical composition may comprise 50 mg/mL (±15%) ethanol.

The pharmaceutical composition may comprise 50 mg/mL (±10%) ethanol.

The pharmaceutical composition may comprise 50 mg/mL (±5%) ethanol.

The pharmaceutical composition may comprise 50 mg/mL (±2%) ethanol.

The pharmaceutical composition may comprise 50 mg/mL (±1%) ethanol.

The pharmaceutical composition may comprise 50 mg/mL ethanol.

The pharmaceutical composition may comprise 5-50 mg/mL (±15%) ethanol.

The pharmaceutical composition may comprise 5-50 mg/mL (±10%) ethanol.

The pharmaceutical composition may comprise 5-50 mg/mL (±5%) ethanol.

The pharmaceutical composition may comprise 5-50 mg/mL (±2%) ethanol.

The pharmaceutical composition may comprise 5-50 mg/mL (±1%) ethanol.

The pharmaceutical composition may comprise 5-50 mg/mL ethanol.

The pharmaceutical composition may comprise 5-10 mg/mL sodium chloride.

The pharmaceutical composition may comprise 6-9 mg/mL sodium chloride.

The pharmaceutical composition may comprise 7.2 mg/mL (±15%) sodium chloride.

The pharmaceutical composition may comprise 7.2 mg/mL (±10%) sodium chloride.

The pharmaceutical composition may comprise 7.2 mg/mL (±5%) sodium chloride.

The pharmaceutical composition may comprise 7.2 mg/mL (±2%) sodium chloride.

The pharmaceutical composition may comprise 7.2 mg/mL (±1%) sodium chloride.

The pharmaceutical composition may comprise 7.2 mg/mL sodium chloride.

In the pharmaceutical composition the citrate buffer may be prepared from citric acid and sodium hydroxide. Alternatively the citrate buffer may be prepared using appropriate quantities of sodium citrate and HCl.

In the pharmaceutical composition 1-3 mg/mL citric acid (anhydrous basis) and 0.5-1.0 mg/mL sodium hydroxide may be used to prepare the citrate buffer.

In the pharmaceutical composition 1.9 mg/mL (±15%) citric acid (anhydrous basis) and 0.75 mg/mL (±15%) sodium hydroxide may be used to prepare the citrate buffer.

In the pharmaceutical composition 1.9 mg/mL (±10%) citric acid (anhydrous basis) and 0.75 mg/mL (±10%) sodium hydroxide may be used to prepare the citrate buffer.

In the pharmaceutical composition 1.9 mg/mL (±5%) citric acid (anhydrous basis) and 0.75 mg/mL (±5%) sodium hydroxide may be used to prepare the citrate buffer.

In the pharmaceutical composition 1.9 mg/mL (±2%) citric acid (anhydrous basis) and 0.75 mg/mL (±2%) sodium hydroxide may be used to prepare the citrate buffer.

In the pharmaceutical composition 1.9 mg/mL (±1%) citric acid (anhydrous basis) and 0.75 mg/mL (±1%) sodium hydroxide may be used to prepare the citrate buffer.

In the pharmaceutical composition 1.9 mg/mL citric acid (anhydrous basis) and 0.75 mg/mL sodium hydroxide may be used to prepare the citrate buffer.

The pharmaceutical composition may have an end of synthesis (EOS) radioactive concentration (RAC) of 5-500 mCi/mL.

The pharmaceutical composition may have an end of synthesis (EOS) radioactive concentration (RAC) of 5-200 mCi/mL.

The pharmaceutical composition may have an end of synthesis (EOS) radioactive concentration (RAC) of 50-100 mCi/mL.

The pharmaceutical composition may have an end of synthesis (EOS) radioactive concentration (RAC) of 10-100 mCi/mL.

The term "end of synthesis" refers to the point in time when the labelled compound is collected in the product collection vial.

The pharmaceutical composition may have an end of synthesis (EOS) radioactive concentration (RAC) of 20-90 mCi/mL.

The pharmaceutical composition may have an end of synthesis (EOS) radioactive concentration (RAC) of at least 35 mCi/mL.

The pharmaceutical composition may comprise 10 mM (±15%) citrate buffer, 50 mg/mL (±15%) ethanol, 7.2 mg/mL (±15%) sodium chloride, and have a pH of 5 (±15%).

The pharmaceutical composition may comprise 10 mM (±10%) citrate buffer, 50 mg/mL (±10%) ethanol, 7.2 mg/mL (±10%) sodium chloride, and have a pH of 5 (±10%).

The pharmaceutical composition may comprise 10 mM (±5%) citrate buffer, 50 mg/mL (±5%) ethanol, 7.2 mg/mL (±5%) sodium chloride, and have a pH of 5 (±5%).

The pharmaceutical composition may comprise 10 mM (±2%) citrate buffer, 50 mg/mL (±2%) ethanol, 7.2 mg/mL (±2%) sodium chloride, and have a pH of 5 (±2%).

The pharmaceutical composition may comprise 10 mM (±1%) citrate buffer, 50 mg/mL (±1%) ethanol, 7.2 mg/mL (±1%) sodium chloride, and have a pH of 5 (±1%).

The pharmaceutical composition may comprise 10 mM citrate buffer, 50 mg/mL ethanol, 7.2 mg/mL sodium chloride, and have a pH of 5.

The pharmaceutical composition may comprise a radiohybrid agent containing a silicon-fluoride and a chelating group wherein either the fluorine is $^{18}F$ or the chelating group contains a chelated radioactive metal wherein the composition has a pH of 5.0 (±15%) and further comprises:
 (a) 10 mM (±15%) citrate buffer; and
 (b) 50 mg/mL (±15%) ethanol; and
 (c) 7.2 mg/mL (±15%) sodium chloride.

The pharmaceutical composition may comprise a radiohybrid agent containing a silicon-fluoride and a chelating group wherein either the fluorine is $^{18}F$ or the chelating group contains a chelated radioactive metal wherein the composition has a pH of 5.0 (±10%) and further comprises:
 (a) 10 mM (±10%) citrate buffer; and
 (b) 50 mg/mL (±10%) ethanol; and
 (c) 7.2 mg/mL (±10%) sodium chloride.

The pharmaceutical composition may comprise a radiohybrid agent containing a silicon-fluoride and a chelating group wherein either the fluorine is $^{18}F$ or the chelating group contains a chelated radioactive metal wherein the composition has a pH of 5.0 (±5%) and further comprises:
 (a) 10 mM (±5%) citrate buffer; and
 (b) 50 mg/mL (±5%) ethanol; and
 (c) 7.2 mg/mL (±5%) sodium chloride.

The pharmaceutical composition may comprise a radiohybrid agent containing a silicon-fluoride and a chelating group wherein either the fluorine is $^{18}F$ or the chelating group contains a chelated radioactive metal wherein the composition has a pH of 5.0 (±2%) and further comprises:
 (a) 10 mM (±2%) citrate buffer; and
 (b) 50 mg/mL (±2%) ethanol; and
 (c) 7.2 mg/mL (±2%) sodium chloride.

The pharmaceutical composition may comprise a radiohybrid agent containing a silicon-fluoride and a chelating group wherein either the fluorine is $^{18}F$ or the chelating group contains a chelated radioactive metal wherein the composition has a pH of 5.0 (±1%) and further comprises:
 (a) 10 mM (±1%) citrate buffer; and
 (b) 50 mg/mL (±1%) ethanol; and
 (c) 7.2 mg/mL (±1%) sodium chloride.

The pharmaceutical composition may comprise a radiohybrid agent containing a silicon-fluoride and a chelating group wherein either the fluorine is $^{18}F$ or the chelating group contains a chelated radioactive metal wherein the composition has a pH of 5.0 and further comprises:
 (a) 10 mM citrate buffer; and
 (b) 50 mg/mL ethanol; and
 (c) 7.2 mg/mL sodium chloride.

The pharmaceutical composition may be diluted with sodium chloride solution prior to administration. The pharmaceutical composition may be diluted up to 10-fold or more with sodium chloride solution prior to administration. The sodium chloride solution used as a diluent prior to administration may be an aqueous solution of 9 mg/mL (±5%) sodium chloride.

After dilution with sodium chloride solution the pharmaceutical composition may comprise 1.1 mM (±15%) citrate buffer.

After dilution with sodium chloride solution the pharmaceutical composition may comprise 1.1 mM (±10%) citrate buffer.

After dilution with sodium chloride solution the pharmaceutical composition may comprise 1.1 mM (±5%) citrate buffer.

After dilution with sodium chloride solution the pharmaceutical composition may comprise 1.1 mM (±2%) citrate buffer.

After dilution with sodium chloride solution the pharmaceutical composition may comprise 1.1 mM (±1%) citrate buffer.

After dilution with sodium chloride solution the pharmaceutical composition may comprise 1.1 mM citrate buffer.

After dilution with sodium chloride solution the pharmaceutical composition may comprise 5.3 mg/mL (±15%) ethanol.

After dilution with sodium chloride solution the pharmaceutical composition may comprise 5.3 mg/mL (±10%) ethanol.

After dilution with sodium chloride solution the pharmaceutical composition may comprise 5.3 mg/mL (±5%) ethanol.

After dilution with sodium chloride solution the pharmaceutical composition may comprise 5.3 mg/mL (±2%) ethanol.

After dilution with sodium chloride solution the pharmaceutical composition may comprise 5.3 mg/mL (±1%) ethanol.

After dilution with sodium chloride solution the pharmaceutical composition may comprise 5.3 mg/mL ethanol.

After dilution with sodium chloride solution the pharmaceutical composition may comprise 5-10 mg/mL sodium chloride.

After dilution with sodium chloride solution the pharmaceutical composition may comprise 8.8 mg/mL (±15%) sodium chloride.

After dilution with sodium chloride solution the pharmaceutical composition may comprise 8.8 mg/mL (±10%) sodium chloride.

After dilution with sodium chloride solution the pharmaceutical composition may comprise 8.8 mg/mL (±5%) sodium chloride.

After dilution with sodium chloride solution the pharmaceutical composition may comprise 8.8 mg/mL (±2%) sodium chloride.

After dilution with sodium chloride solution the pharmaceutical composition may comprise 8.8 mg/mL (±1%) sodium chloride.

After dilution with sodium chloride solution the pharmaceutical composition may comprise 8.8 mg/mL sodium chloride.

After dilution with sodium chloride solution the pharmaceutical composition may comprise 1.1 mM (±15%) citrate buffer, 5.3 mg/mL (±15%) ethanol, 8.8 mg/mL (±15%) sodium chloride, and have a pH of 5.1 (±15%).

After dilution with sodium chloride solution the pharmaceutical composition may comprise 1.1 mM (±10%) citrate buffer, 5.3 mg/mL (±10%) ethanol, 8.8 mg/mL (±10%) sodium chloride, and have a pH of 5.1 (±10%).

After dilution with sodium chloride solution the pharmaceutical composition may comprise 1.1 mM (±5%) citrate buffer, 5.3 mg/mL (±5%) ethanol, 8.8 mg/mL (±5%) sodium chloride, and have a pH of 5.1 (±5%).

After dilution with sodium chloride solution the pharmaceutical composition may comprise 1.1 mM (±2%) citrate buffer, 5.3 mg/mL (±2%) ethanol, 8.8 mg/mL (±2%) sodium chloride, and have a pH of 5.1 (±2%).

After dilution with sodium chloride solution the pharmaceutical composition may comprise 1.1 mM (±1%) citrate buffer, 5.3 mg/mL (±1%) ethanol, 8.8 mg/mL (±1%) sodium chloride, and have a pH of 5.1 (±1%).

After dilution with sodium chloride solution the pharmaceutical composition may comprise 1.1 mM citrate buffer, 5.3 mg/mL ethanol, 8.8 mg/mL sodium chloride, and have a pH of 5.1.

The pharmaceutical composition may improve product stability by reducing pH. During testing it was identified that the product is less stable under basic conditions, yielding the hydrolysed silanol product (displacement of F— by OH—). Decreasing the pH helped stabilise the product and citrate pH 5 was selected.

Ethanol can be used as a radiolysis protectant. Optimisation of the amount of ethanol lead to the development of the stabilized material as described herein.

Different quantities of components can be combined. For example the buffer can be 0.1-200 mM citrate buffer having a pH of 4.5-5.5 and up to 70 mg/mL ethanol. The composition can contain additional salts for blood isotonicity. The composition contains sodium chloride.

The pharmaceutical composition may bind to PSMA.

The pharmaceutical composition may comprise a radiohybrid agent selected from:

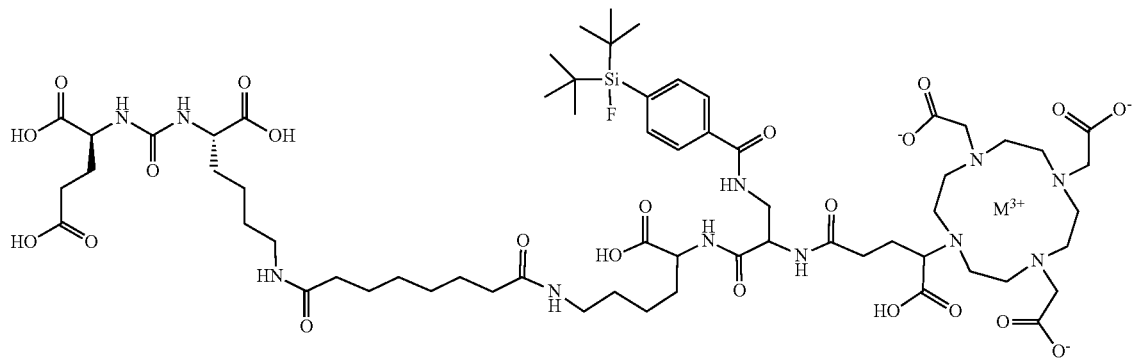

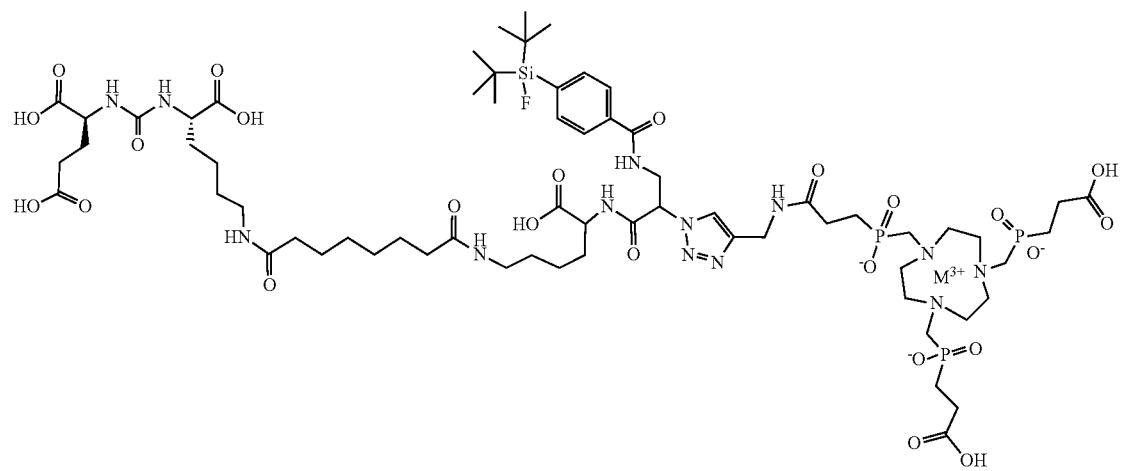
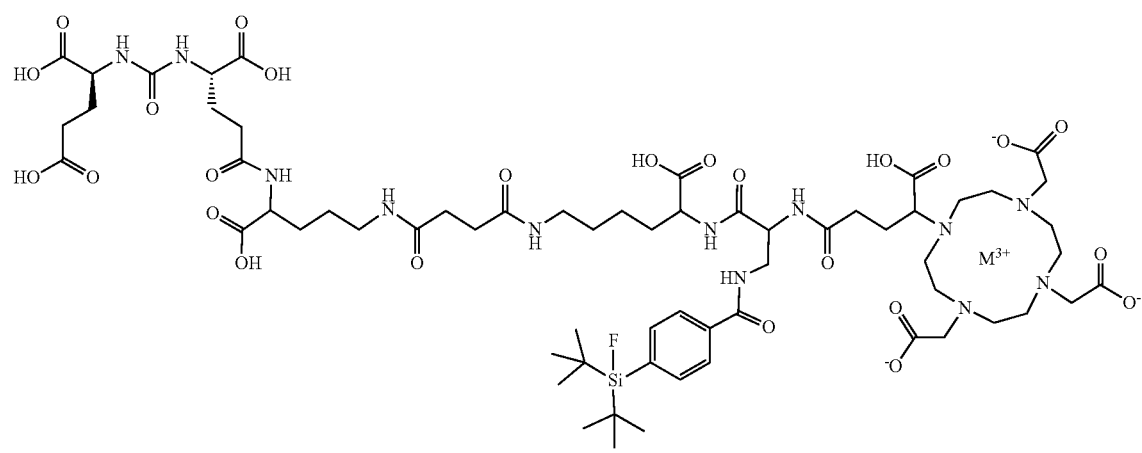
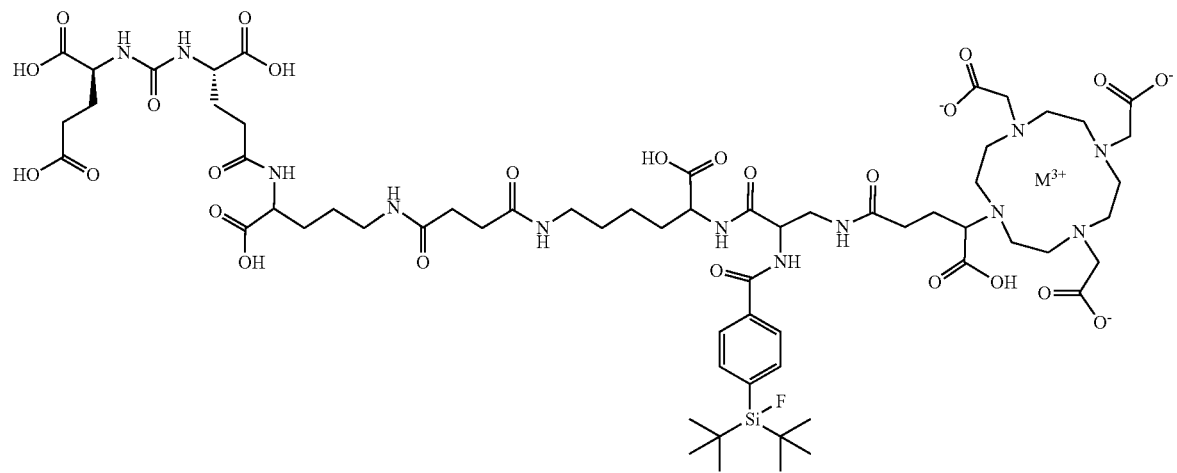

-continued
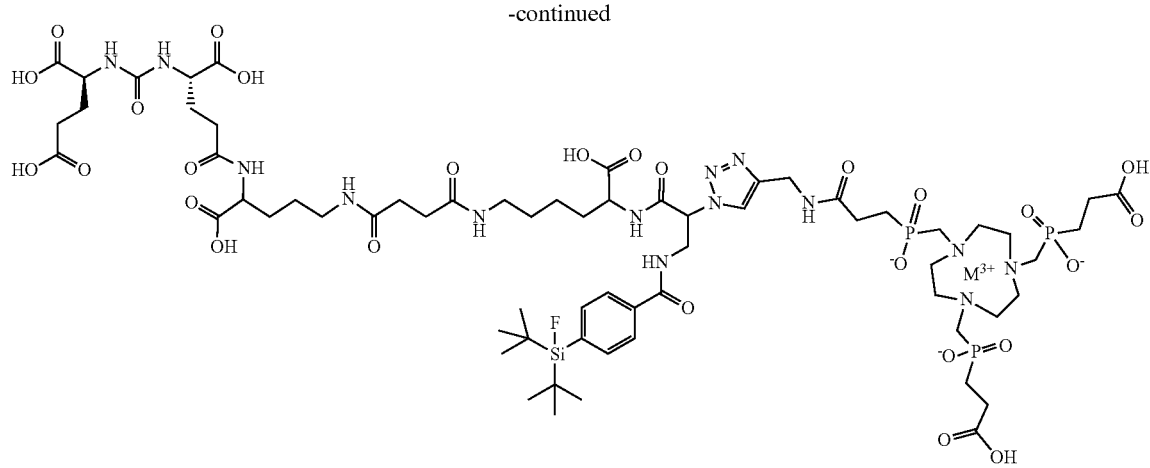
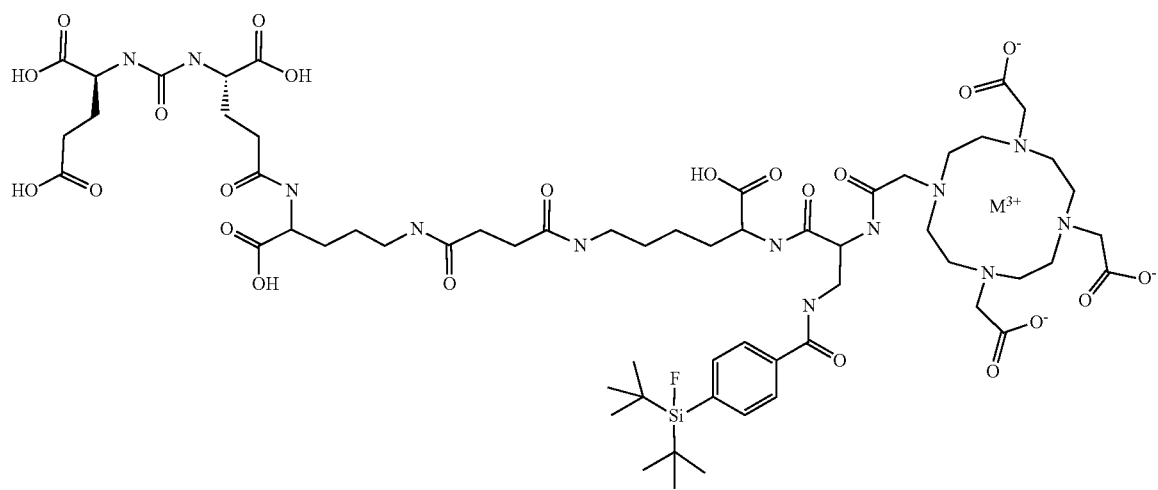
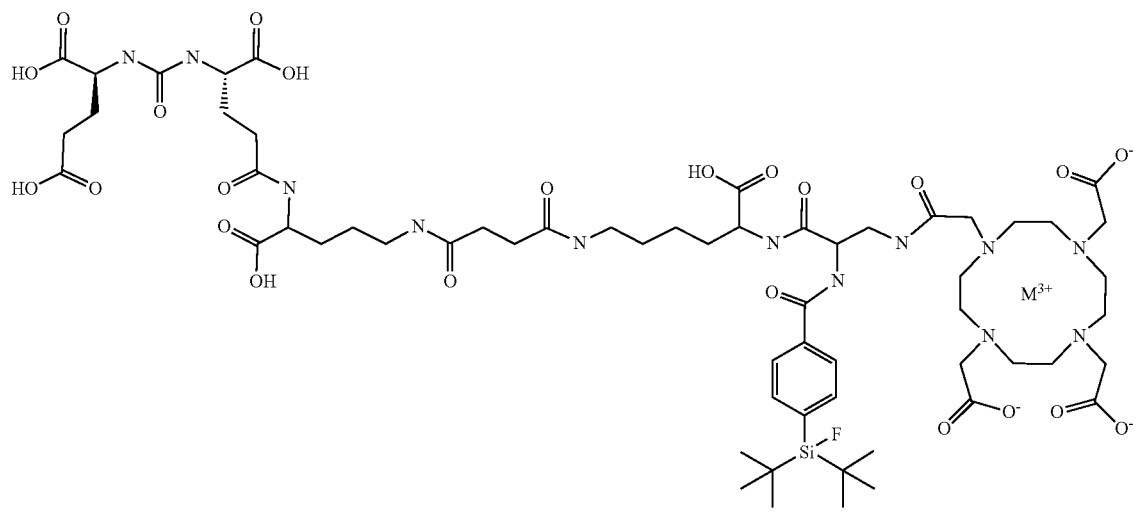
and isomers and salts thereof wherein M³⁺ is a chelated radioactive or non-radioactive metal. The agents may be in the form of pharmaceutically acceptable salts such that for example groups one or more of the groups shown as COOH may be the salts thereof.

The pharmaceutical composition may comprise a radiohybrid agent comprising:

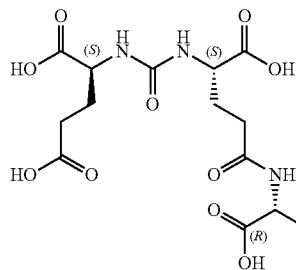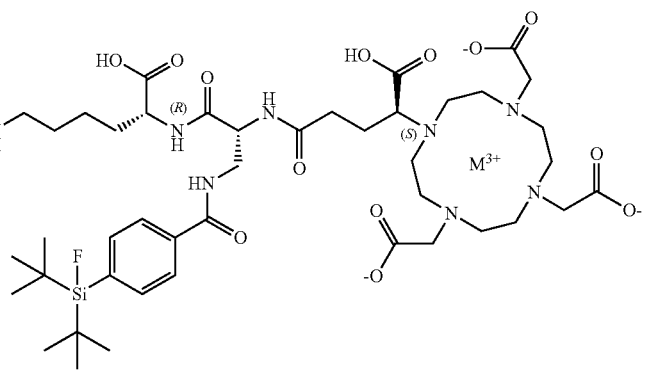

or an isomer or salt thereof.

The pharmaceutical composition may be used as a cancer diagnostic or imaging agent.

The pharmaceutical composition may be used in a method of imaging and/or diagnosing cancer in a patient in need thereof. Thus, there is also presented herein a method of imaging and/or diagnosing cancer comprising administering a conjugate, compound or composition of the invention to a patient in need thereof.

The pharmaceutical composition may be used in the treatment of cancer.

The pharmaceutical composition may be used for the diagnosis, imaging or prevention of neoangiogenesis/angiogenesis.

The pharmaceutical composition may be used as a cancer diagnostic or imaging agent or for use in the treatment of cancer wherein the cancer is prostate, breast, lung, colorectal or renal cell carcinoma.

The pharmaceutical composition comprises a radiohybrid agent having three separate moieties. The three separate moieties are a) one or more ligands which are capable of binding to PSMA, (b) a silicon-fluoride acceptor (SIFA) moiety which comprises a covalent bond between a silicon and a fluorine atom, and (c) one or more chelating groups, containing a chelated nonradioactive or radioactive cation.

Whilst certain ligands which are capable of binding to a disease-relevant target molecule may be cyclic peptides, such cyclic peptides are not chelating groups as envisaged herein, as the problem of the hydrophobic SIFA moiety is not solved in the absence of a further chelating moiety. Thus the radiohybrids of the compositions of the invention require a hydrophilic chelating group in addition to the ligands which are capable of binding to PSMA. The hydrophilic chelating group is required to reduce the hydrophobic nature of the radiohybrids of the compositions caused by the presence of the SIFA moiety.

The ligand in relation to the first aspect of the invention is defined in functional terms. This is the case because the present invention does not depend on the specific nature of the ligand in structural terms. Rather, a key aspect of the invention is the combination, within a single molecule, of a silicon-fluoride acceptor and a chelator or a chelate. These two structural elements, SIFA and the chelator, exhibit a spatial proximity. Preferably, the shortest distance between two atoms of the two elements is less or equal 25 Å, more preferably less than 20 Å and even more preferably less than 15 Å. Alternatively or in addition, it is preferred that not more than 25 covalent bonds separate an atom of the SIFA moiety and an atom the chelator, preferably not more than 20 chemical bonds and even more preferably not more than 15 chemical bonds.

The cation in accordance with item (c) of the can be a radioactive or a non-radioactive cation. Examples are given further below. As a consequence, conjugates can be radioactively labelled at the SIFA moiety, or not radiolabelled at the SIFA moiety. In the former case, the chelating group may be either a complex of a cold (non-radioactive) ion or may be devoid of any ion. In the latter case, the chelator will contain a radioactive cation.

The present inventors discovered that placement of the silicon-fluoride acceptor in the neighbourhood of a hydrophilic chelator such as, but not limited to, DOTAGA or DOTA, shields or compensates efficiently the lipophilicity of the SIFA moiety to an extent which shifts the overall hydrophobicity of compound in a range which renders the compound suitable for in-vivo administration.

A further advantage of the radiohybrids of the compositions, especially of PSMA targeted radiohybrids of the present invention is their surprisingly low accumulation in the kidneys of mice when compared to other PSMA targeted radiopharmaceuticals, such as PSMA I&T. Without wishing to be bound by a particular theory, it seems to be the combination of the structural element SIFA with a chelator which provides for the unexpected reduction of accumulation in the kidneys.

In a preferred embodiment, a ligand in accordance with the invention comprises or consists of a peptide, a peptidomimetic or a substituted urea, substituents including amino acids. It is understood that a ligand which comprises a peptide or peptidomimetic also comprises a non-peptidic and non-peptidomimetic part. In terms of molecular weight, preference is given to molecular weights below 15 kDa, below 10 kDa or below 5 kDa. Accordingly, small proteins are also embraced by the term "ligand". Target molecules are not particularly limited and include enzymes, receptors, epitopes, transporters, cell surface molecules and proteins of the extracellular matrix. Preferred are targets which are disease relevant. Particularly preferred are targets which are causally involved in a given disease, or which are highly overexpressed in a given disease and/or the inhibition of which can cause a beneficial effect in a patient suffering from a given disease. The ligands are preferably high affinity ligands with preferable affinity, expressed as $IC_{50}$, being below 50 nM, below 20 nM or below nM.

Especially preferred are those ligands which bind with high affinity to prostate-specific membrane antigen (PSMA).

Preferably, the silicon-fluoride acceptor (SIFA) moiety has the structure represented by formula (I):

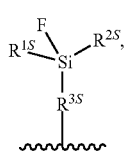

(I)

Wherein F is understood to encompass both $^{19}F$ and $^{18}F$, $R^{1S}$ and $R^{2S}$ are independently a linear or branched C3 to C10 alkyl group, preferably $R^{1S}$ and $R^{2S}$ are selected from isopropyl and tert-butyl, and are more preferably $R^{1S}$ and $R^{2S}$ are tert-butyl; $R^{3S}$ is a C1 to C20 hydrocarbon group which may comprise one or more aromatic and one or more aliphatic units and/or up to 3 heteroatoms selected from O and S, preferably $R^{3S}$ is a C6 to C10 hydrocarbon group which comprises an aromatic ring and which may comprise one or more aliphatic units; more preferably $R^{3S}$ is a phenyl ring, and most preferably, $R^{3S}$ is a phenyl ring wherein the Si-containing substituent and the bond marked by ⁓⁓⁓ are in a para-position, and wherein the SIFA moiety is attached to the remainder of the conjugate via the bond marked by ⁓⁓⁓.

More preferably, the silicon-fluoride acceptor (SIFA) moiety has the structure represented by formula (Ia):

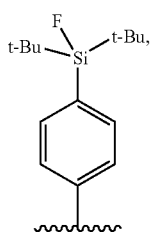

(Ia)

wherein t-Bu indicates a tert-butyl group;
and F is understood to encompass both $^{19}F$ and $^{18}F$.

A preferred chelating group comprises at least one of the following (i), (ii) or (iii).

(i) A macrocyclic ring structure with 8 to 20 ring atoms of which 2 or more, more preferably 3 or more, are selected from oxygen atoms or nitrogen atoms. Preferably, 6 or less ring atoms are selected from oxygen atoms or nitrogen atoms. Especially preferred is that 3 or 4 ring atoms are nitrogen atoms or oxygen atoms. Among the oxygen and nitrogen atoms, preference is given to the nitrogen atoms. In combination with the macrocyclic ring structure, the preferred chelating group may comprise 2 or more, such as 2 to 6, preferably 2 to 4, carboxyl groups and/or hydroxyl groups. Among the carboxyl groups and the hydroxyl groups, preference is given to the carboxyl groups.

(ii) An acyclic, open chain chelating structure with 8 to 20 main chain (back bone) atoms of which 2 or more, more preferably 3 or more are heteroatoms selected from oxygen atoms or nitrogen atoms. Preferably, 6 or less back bone atoms are selected from oxygen atoms or nitrogen atoms. Among the oxygen and nitrogen atoms, preference is given to the nitrogen atoms. More preferably, the open chain chelating structure is a structure which comprises a combination of 2 or more, more preferably 3 or more heteroatoms selected from oxygen atoms or nitrogen atoms, and 2 or more, such as 2 to 6, preferably 2 to 4, carboxyl groups and/or hydroxyl groups. Among the carboxyl groups and the hydroxyl groups, preference is given to the carboxyl groups.

(iii) A branched chelating structure containing a quarternary carbon atom. Preferably the quarternary carbon atom is substituted with 3 identical chelating groups in addition to the SIFA/ligand moiety. The substituted chelating groups can comprise an amide. The substituted chelating groups can comprise an aromatic group. The substituted chelating groups can comprise a hydroxypyridinone.

In preferred specific examples, the chelating group is a residue of a chelating agent selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecan (DO2A) 1,4,7,10-tetracyclododecan-N,N',N'',N'''-tetraacetic acid (DOTA), α-(2-carboxyethyl)-1,4,7,10-tetraazacyclododecane-1,4,7,10-tetraacetic acid (DOTAGA), 1,4,7,10 tetraazacyclododecane N, N', N'', N''' 1,4,7,10-tetra(methylene) phosphonic acid (DOTMP), N,N'-dipyridoxylethylendiamine-N,N'-diacetate-5,5'-bis (phosphat) (DPDP), diethylene triamine N,N',N'' penta (methylene) phosphonic acid (DTMP), diethylenetriaminepentaacetic acid (DTPA), ethylenediamine-N,N'-tetraacetic acid (EDTA), ethyleneglykol-O,O-bis(2-anninoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), tetra 3-hydroxy-N-methyl-2-pyridinone chelators (4-((4-(3-(bis(2-(3-hydroxy-1-methyl-2-oxo-1,2-dihydropyridine-4-carboxamido)ethyl)amino)-2-((bis (2-(3-hydroxy-1-methyl-2-oxo-1,2-dihydropyridine-4-carboxamido)ethyl)amino)methyl)propyl)phenyl)amino)-4-oxobutanoic acid), abbreviated as Me-3,2-HOPO, 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), tris(hydroxypyridinone) (THP), terpyridin-bis (methyleneamintetraacetic acid (TMT), 1,4,7-triazacyclononane-1,4,7-tris[methylene(2-carboxyethyl)phosphinic acid] (TRAP), 1,4,7,10-tetraazacyclotridecan-N,N',N'',N'''-tetraacetic acid (TRITA), 3-[[4,7-bis[[2-carboxyethyl(hydroxy)phosphoryl]methyl]-1,4,7-triazonan-1-yl]methyl-hydroxy-phosphoryl]propanoic acid, and triethylenetetraaminehexaacetic acid (TTHA), which residue is provided by covalently binding a carboxyl group contained in the chelating agent to the remainder of the conjugate via an ester or an amide bond.

Particular chelators are shown below:

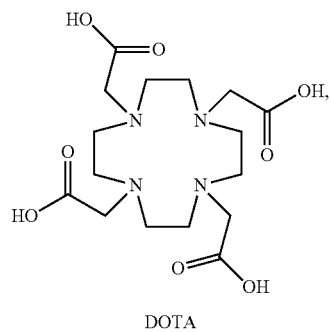
DOTA

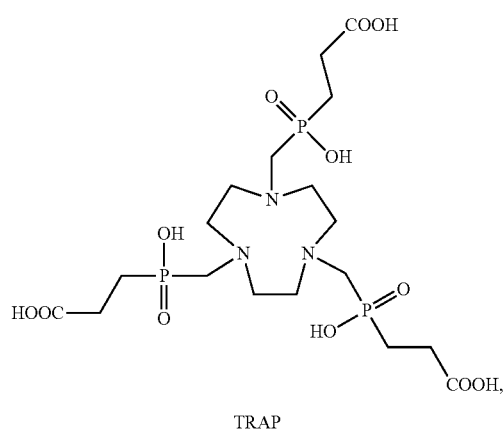
TRAP

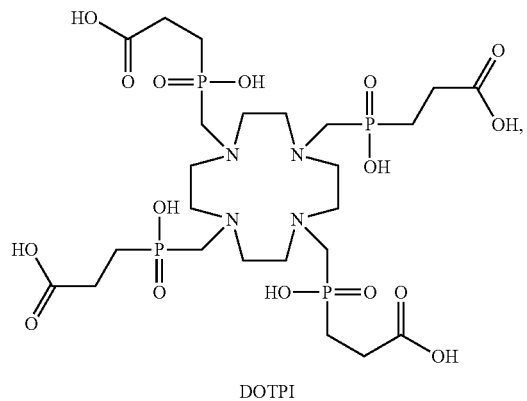
DOTPI

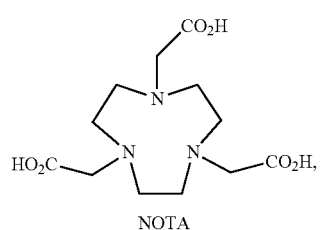
NOTA

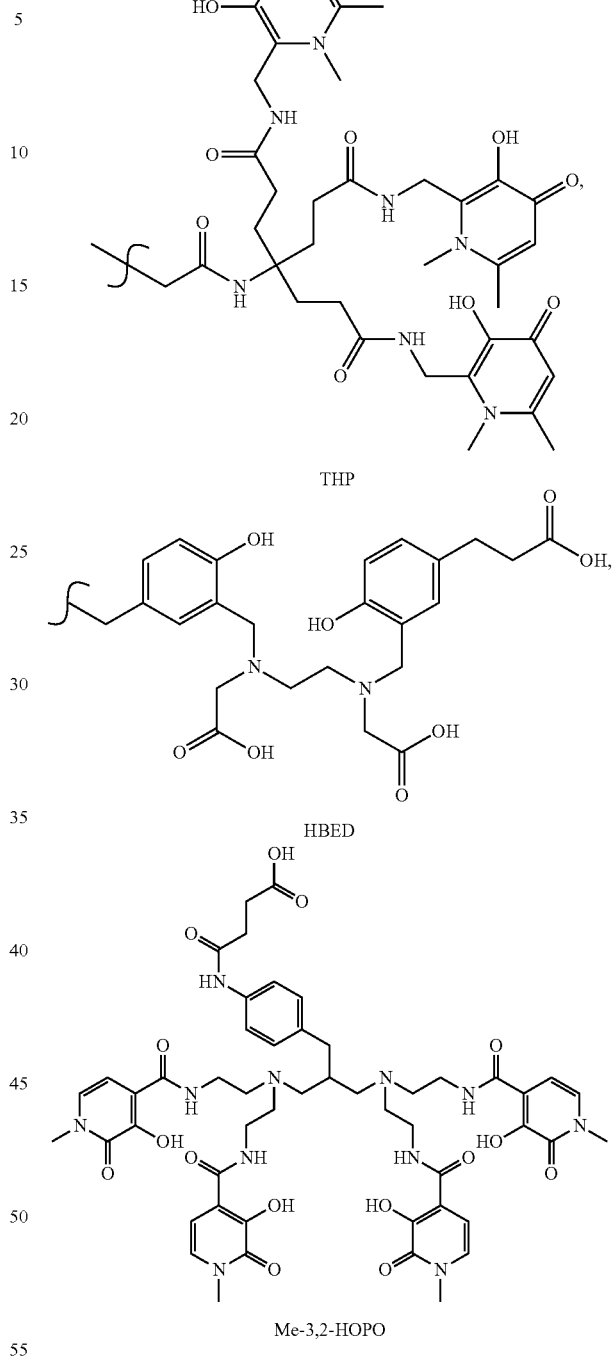

Among the above exemplary chelating agents, particular preference is given to a chelating agent selected from TRAP, DOTA and DOTAGA.

Metal- or cation-chelating macrocyclic and acyclic compounds are well-known in the art and available from a number of manufacturers. While the chelating moiety in accordance with the present invention is not particularly limited, it is understood that numerous moieties can be used in an off-the-shelf manner by a skilled person without further ado.

The chelating group may comprise a chelated cation which is non-radioactive.

Preferred examples of cations that may be chelated by the chelating group are the non-radioactive cations of Sc, Cr, Mn, Co, Fe, Ni, Cu, Ga, Zr, Y, Tc, Ru, Rh, Pd, Ag, In, Sn, Te, Pr, Pm, Tb, Sm, Gd, Tb, Ho, Dy, Er, Yb, Tm, Lu, Re, Pt, Hg, Au, Pb At, Bi, Ra, Ac, Th; more preferably the cations of Sc, Cu, Ga, Y, In, Tb, Ho, Lu, Re, Pb, Bi, Ac, Th and Er. The cation may be Ga. The cation may be Lu.

The chelating group may comprise a chelated cation which is radioactive.

Preferred examples of cations that may be chelated by the chelating group are the cations of $^{43}$Sc, $^{44}$Sc, $^{47}$Sc, $^{51}$Cr, $^{52}$Mn, $^{58}$Co, $^{52}$Fe, $^{56}$Ni, $^{57}$Ni, $^{62}$Cu, $^{64}$Cu, $^{64}$Cu, $^{67}$Cu, $^{66}$Ga, $^{67}$Ga, $^{68}$Ga, $^{89}$Zr, $^{90}$Y, $^{89}$Y, <Tc, $^{99m}$Tc, $^{97}$Ru, $^{105}$Rh, $^{109}$Pd, $^{111}$Ag, $^{110}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{152}$Tb, $^{155}$Tb, $^{161}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{221}$At, $^{212}$Bi, $^{213}$Bi, $^{223}$Ra, $^{225}$Ac, $^{227}$Th a cationic molecule comprising $^{18}$F or a cation such as $^{18}$F—[AlF]$^{2+}$; more preferably the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F. Cations may be selected from Lu-177, Y-90, or Ac-225. Preferred cations may be positron emitting isotopes such as $^{68}$Ga.

Accordingly, the ligand is preferably capable of binding to prostate-specific membrane antigen (PSMA).

More preferably, the ligand has the structure represented by formula (II):

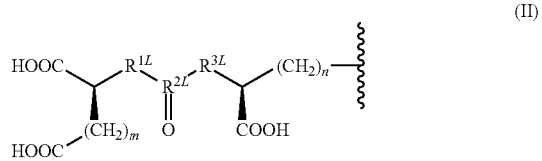

(II)

wherein m is an integer of 2 to 6, preferably 2 to 4, more preferably 2; n is an integer of 2 to 6, preferably 2 to 4, more preferably 2 or 3; $R^{1L}$ is $CH_2$, NH or O, preferably NH; $R^{3L}$ is $CH_2$, NH or O, preferably NH; $R^{2L}$ is C or P(OH), preferably C; and wherein the ligand is attached to the remainder of the conjugate via the bond marked by ∿∿∿.

The ligand can have the structure represented by formula (IIa):

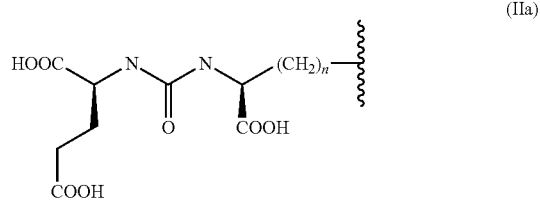

(IIa)

wherein n is an integer of 2 to 6; and wherein the ligand is attached to the remainder of the conjugate via the bond marked by ∿∿∿.

A number of PSMA binders are known in the art which are all suitable in accordance with the invention. The above preferred embodiment is a structural definition of a preferred group of PSMA binders.

It is particularly preferred that the conjugate of the first aspect is a compound of formula (III):

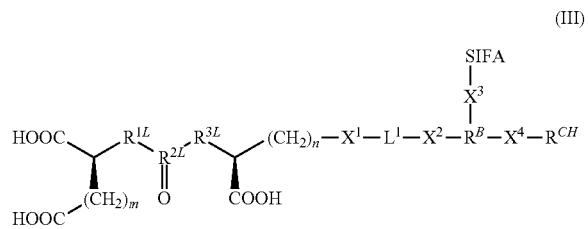

(III)

or a pharmaceutically acceptable salt thereof, wherein:

SIFA is a silicon-fluoride acceptor (SIFA) moiety which comprises a covalent bond between a silicon and a fluorine atom and which is labeled with $^{18}$F; preferably SIFA is the SIFA moiety of formula (I) and more preferably of formula (Ia) defined above;

m is an integer of 2 to 6, preferably 2 or 3, more preferably 2;

n is an integer of 2 to 6, preferably 2 or 3, more preferably 2 or 4;

$R^{1L}$ is $CH_2$, NH or O, preferably NH;

$R^{3L}$ is $CH_2$, NH or O, preferably NH;

$R^{2L}$ is C or P(OH), preferably C;

$X^1$ is selected from an amide bond, an ether bond, a thioether bond, an ester bond, a thioester bond, an urea bridge, and an amine bond, preferably an amide bond;

$X^2$ is selected from an amide bond, an ether bond, a thioether bond, an ester bond, a thioester bond, an urea bridge, and an amine bond, preferably an amide bond;

$L^1$ is a divalent linking group with a structure selected from an oligoamide, an oligoether, an oligothioether, an oligoester, an oligothioester, an oligourea, an oligo (ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo ether-urea), an oligo (thioether-ester), an oligo(thioether-thioester), an oligo (thioether-urea), an oligo(ester-thioester), an oligo(ester-urea), and an oligo(thioester-urea), preferably with a structure selected from an oligoamide and an oligo (ester-amide).

$L^1$ can be optionally substituted with one or more substituents independently selected from —OH, —OCH$_3$, —COOH, —COOCH$_3$, —NH$_2$, and —NHC(NH)NH$_2$.

$X^3$ is selected from an amide bond, and ester bond, an ether, an amine, and a linking group of the formula:

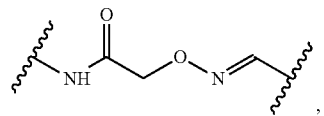 [SMILES: */C=N/OCC(=O)N*]

, wherein the bond marked by ∿∿∿ at the NH group is bound to R B and the other bond marked by ∿∿∿ is bound to SIFA; preferably $X^3$ is an amide bond; R B is a trivalent coupling group.

$X^4$ is selected from an amide bond, an ether bond, a thioether bond, and ester bond, a thioester bond, a urea bridge, an amine bond, a linking group of the formula:

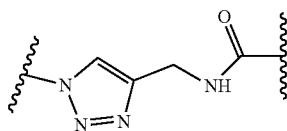 [SMILES: *C(=O)NCc1cn(*)nn1]

wherein the amide bond marked by ⌇⌇⌇ is formed with the chelating group, and the other bond marked by ⌇⌇⌇ is bound to $R^B$; and a linking group of the formula:

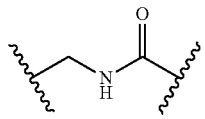

wherein the bond marked by ⌇⌇⌇ at the carbonyl end is formed with the chelating group, and the other bond marked by ⌇⌇⌇ is bound to $R^B$; preferably $X^4$ is an amide bond.

$R^{CH}$ is chelating group containing a chelated nonradioactive or nonradioactive cation, preferably a nonradioactive or radioactive metal cation, wherein preferred embodiments of said chelating group and of the optional chelated cation are as defined above.

The term "oligo" as used in oligoamide, oligoether, oligothioether, oligoester, oligothioester, oligourea, oligo(ether-amide), oligo(thioether-amide), oligo(ester-amide), oligo(thioester-amide), oligo(urea-amide), oligo(ether-thioether), oligo(ether-ester), oligo(ether-thioester), oligo (ether-urea), oligo(thioether-ester), oligo(thioether-thioester), oligo (thioether-urea), oligo(ester-thioester), oligo(ester-urea), and oligo(thioester-urea) is preferably to be understood as referring to a group wherein 2 to 20, more preferably wherein 2 to 10 subunits are linked by the type of bonds specified in the same terms. As will be understood by the skilled reader, where two different types of bonds are indicated in brackets, both types of bonds are contained in the concerned group (e.g. in "oligo (ester-amide)", ester bonds and amide bonds are contained).

It is preferred that $L^1$ comprises a total of 1 to 5, more preferably a total of 1 to 3, and most preferably a total of 1 or 2 amide and/or ester bonds, preferably amide bonds, within its backbone.

The term oligoamide therefore describes a moiety having a chain of $CH_2$ or CHR groups interspersed with groups selected from NHCO or CONN. Each occurrence of the R moiety is an optional substituent selected from —OH, —OCH$_3$, —COOH, —COOCH$_3$, —NH$_2$, and —NHC(NH)NH$_2$.

It is also preferred that —$X^1$-$L^1$-$X^2$— represents one of the following structures (L-1) and (L-2):

—NH—C(O)—R$^6$—C(O)—NH—R$^7$—NH—C(O)—   (L-1)

—C(O)—NH—R$^8$—NH—C(O)—R$^9$—C(O)—NH—
R$^{10}$—NH—C(O)—   (L-2)

wherein $R^6$ to $R^{10}$ are independently selected from C2 to C10 alkylene, preferably linear C2 to C10 alkylene, which alkylene groups may each be substituted by one or more substituents independently selected from —OH, —OCH$_3$, —COOH, —COOCH$_3$, —NH$_2$, and —NHC(NH)NH$_2$.

Especially preferred is that the total number of carbon atoms in $R^6$ and $R^7$ is 4 to 20, more preferably 4 to 16, without carbon atoms contained in optional substituents. Especially preferred is that the total number of carbon atoms in $R^8$ to $R^{10}$, is 6 to 20, more preferably 6 to 16, without carbon atoms contained in optional substituents.

It is particularly preferred that —$X^1$-$L^1$-$X^2$— represents one of the following structures (L-3) and (L-4):

—NH—C(O)—R$^{11}$—C(O)—NH—R$^{12}$—CH
(COOH)—NH—C(O)—   (L-3)

—C(O)—NH—CH(COOH)—R$^{13}$—NH—C(O)—
R$^{14}$—C(O)—NH—R$^{15}$—CH(COOH)—NH—C
(O)—   (L-4)

wherein $R^{11}$ to $R^{15}$ are independently selected from C2 to C8 alkylene, preferably linear C2 to C8 alkylene.

Especially preferred is that the total number of carbon atoms in $R^{11}$ and $R^{12}$ or $R^{13}$ to $R^{15}$, respectively, is 8 to 18, more preferably 8 to 12, yet more preferably 9 or 10.

Preferably, $R^B$ has the structure represented by formula (IV):

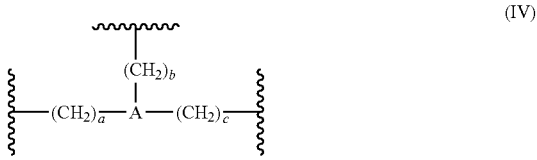

(IV)

wherein: A is selected from N, $CR^{16}$, wherein $R^{16}$ is H or C1-C6 alkyl, and a 5 to 7 membered carbocyclic or heterocyclic group; preferably A is selected from N and CH, and more preferably A is CH; the bond marked by ⌇⌇⌇ at $(CH_2)_a$ is formed with $X^2$, and a is an integer of 0 to 4, preferably 0 or 1, and most preferably 0; the bond marked by ⌇⌇⌇ at $(CH_2)_b$ is formed with $X^3$, and b is an integer of 0 to 4, preferably of 0 to 2, and more preferably 0 or 1; and the bond marked by ⌇⌇⌇ at $(CH_2)_c$ is formed with $X^4$, and c is an integer of 0 to 4, preferably of 0 to 2, and more preferably 0 or 1.

Even more preferred as a conjugate in accordance with the invention is a compound of formula (IIIa):

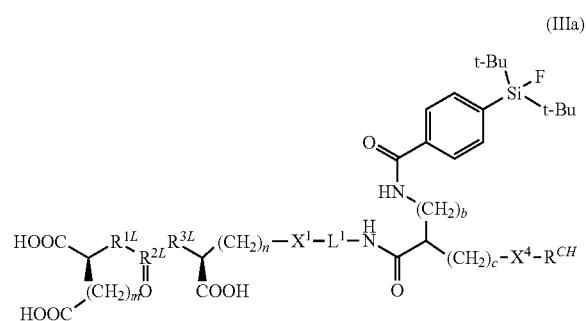

(IIIa)

or a pharmaceutically acceptable salt thereof, wherein m, n, $R^{1L}$, $R^{2L}$, $R^{3L}$, $L^1$, b, c, $X^4$ and $R^{CH}$ are as defined above, including all preferred embodiments thereof.

It is preferred for the compound of formula (IIIa) that b+c≥1.

It is also preferred for the compound of formula (IIIa) that b+c≤3.

It is more preferred for the compound of formula (IIIa) that b is 1 and c is 0.

It is also preferred for the compound of formula (III) that —$X^4$—$R^{CH}$ represents a residue of a chelating agent selected from DOTA and DOTAGA bound with one of its carboxylic groups via an amide bond to the remainder of the conjugate.

In a preferred embodiment of the compound of formula (III), said compound is a compound of formula (IIIb):

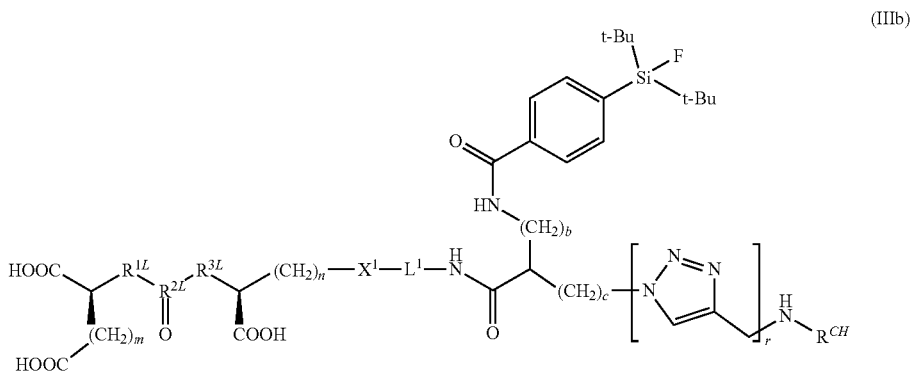

(IIIb)

or a pharmaceutically acceptable salt thereof, wherein m, n, $R^{1L}$_, $R^{2L}$_, $R^{3L}$, $X^1$, $L^1$, b, c, $X^4$ and $R^{CH}$ are as defined above; and r is 0 or 1.

Especially preferred is that —N(H)—$R^{CH}$ represents a residue of a chelating agent selected from DOTA and DOTAGA bound with one of its carboxylic groups via an amide bond to the remainder of the conjugate.

In order to be used in PET imaging, the radiohybrids of the compositions require a positron emitting atom. The radiohybrids of the compositions include $^{18}$F for medical use. Most preferred radiohybrids of the invention are wherein F includes $^{18}$F and $M^{3+}$ refers to a nonradioactive or radioactive metal cation.

Whilst the structures shown herein are shown having COOH groups, the pH of the solution affects whether the groups are salts or acids. Some of the acid groups may be the charged salts. Thus compounds disclosed herein include the carboxylate salts of the compounds shown. Included herein are compositions of the compounds below, or salts thereof:

PSMA-SIFA1 (5)

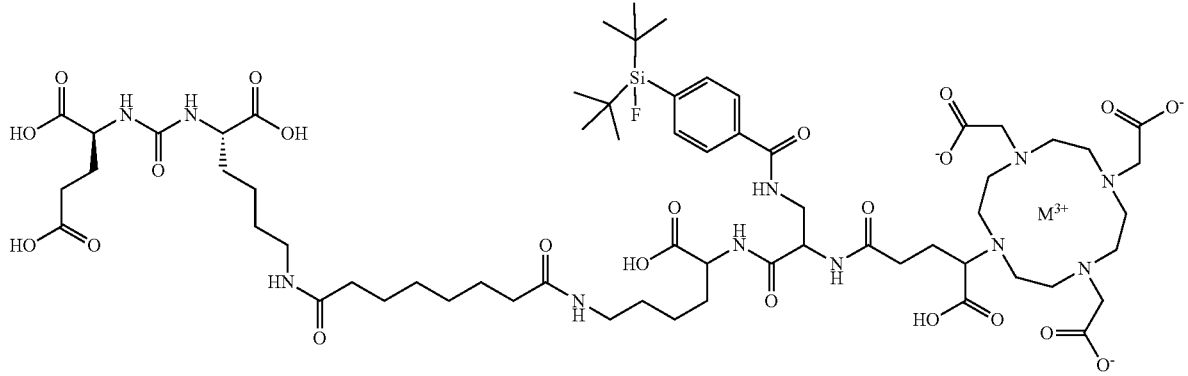

and isomers thereof:
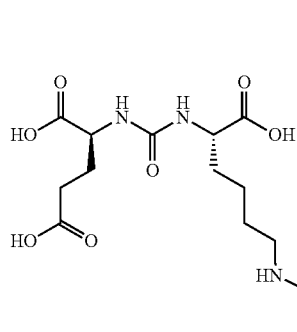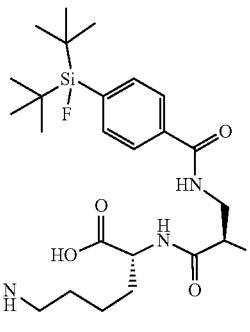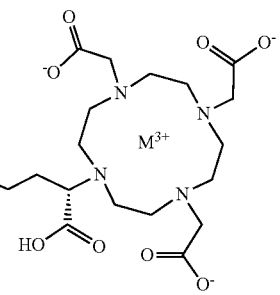
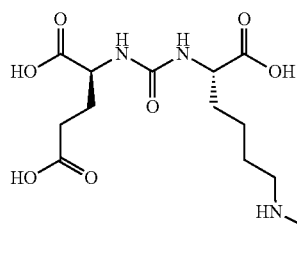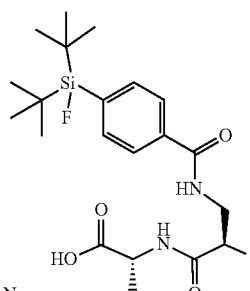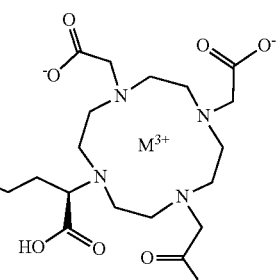
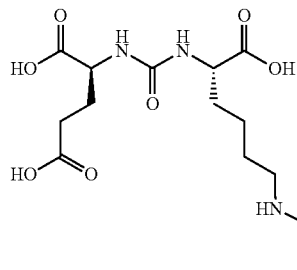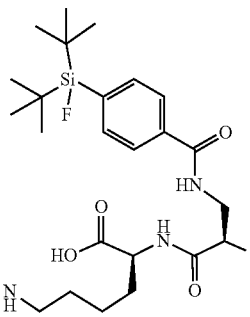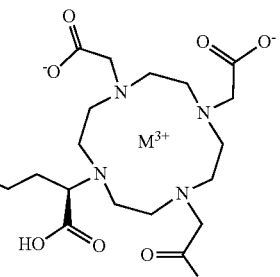
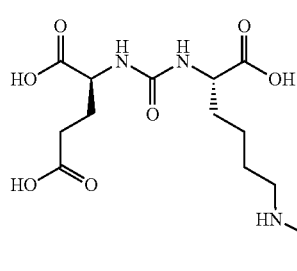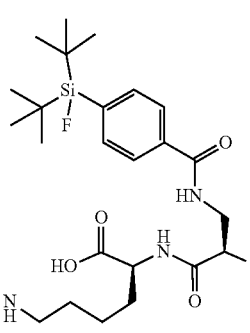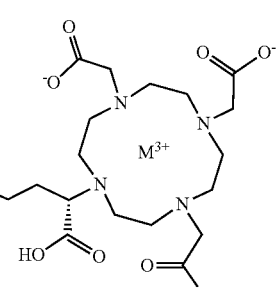

-continued
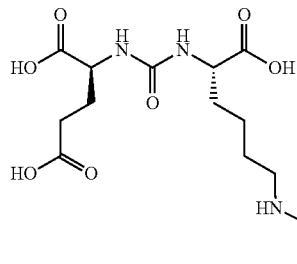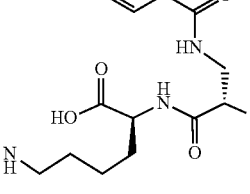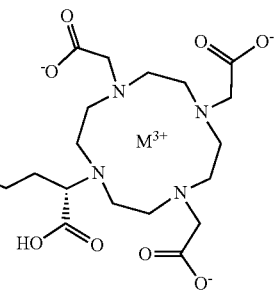
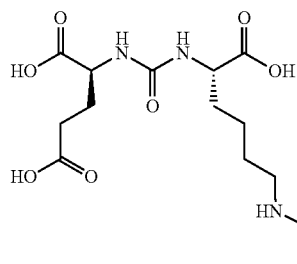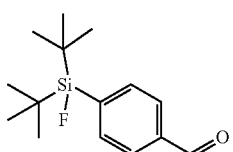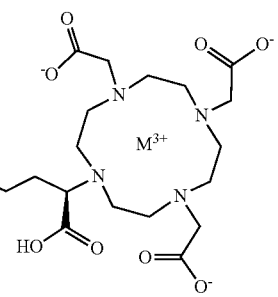
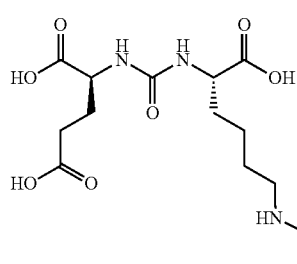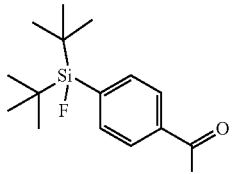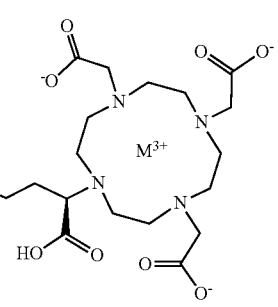
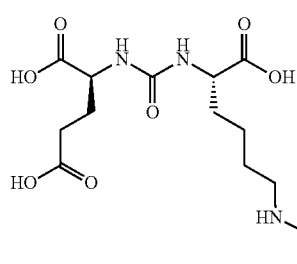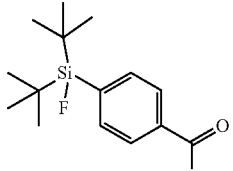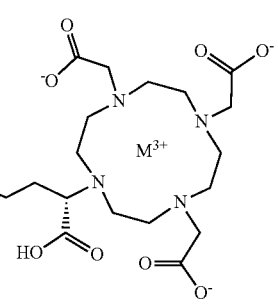

PSMA-SIFA2 (6)
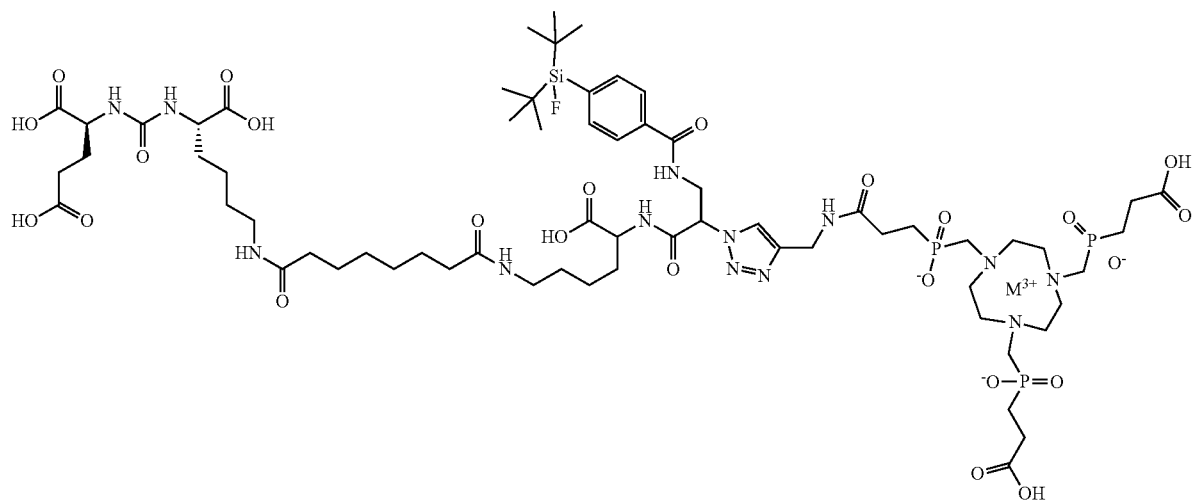
and isomers thereof
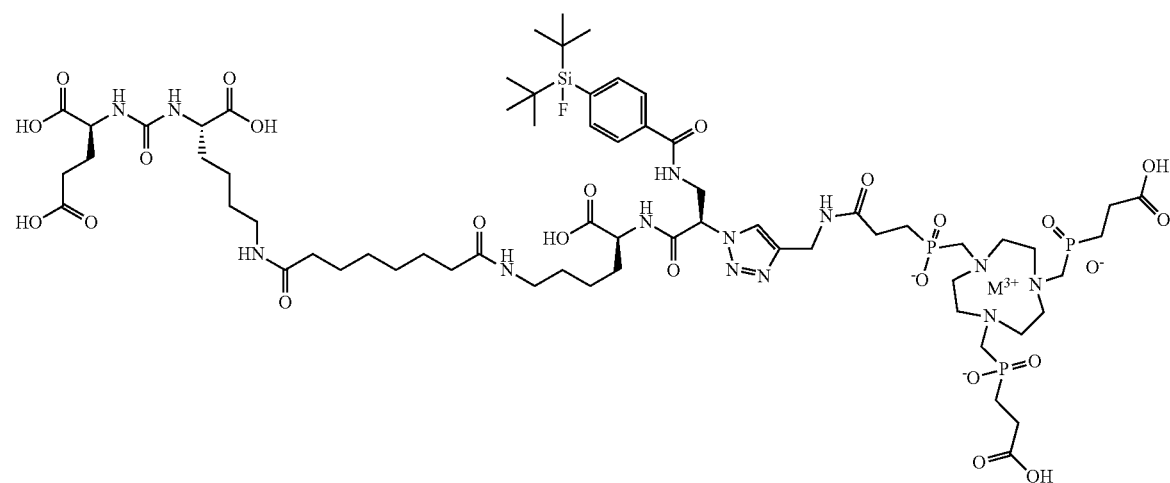
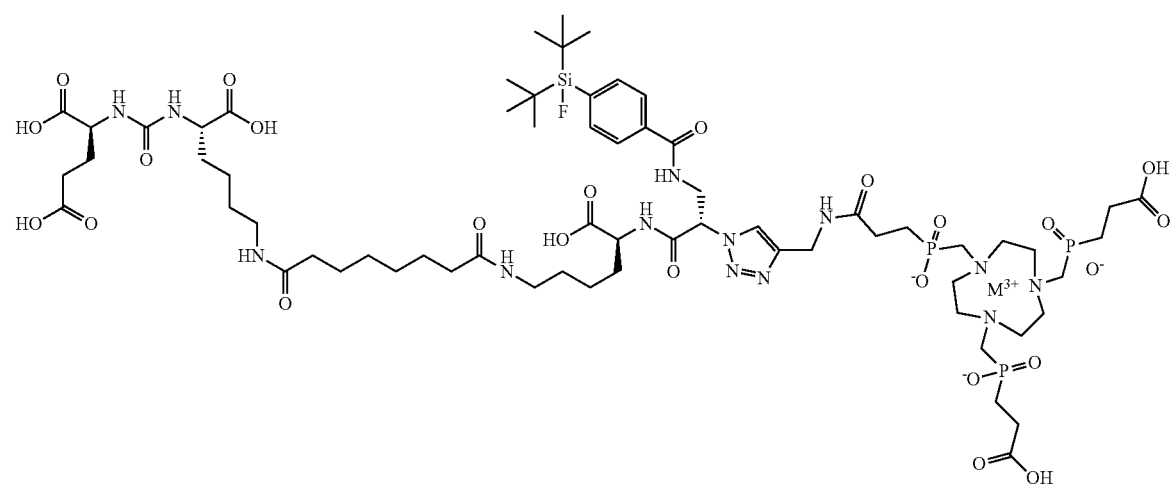

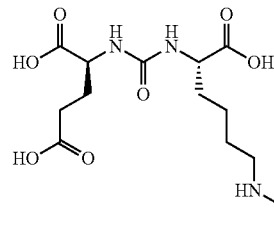
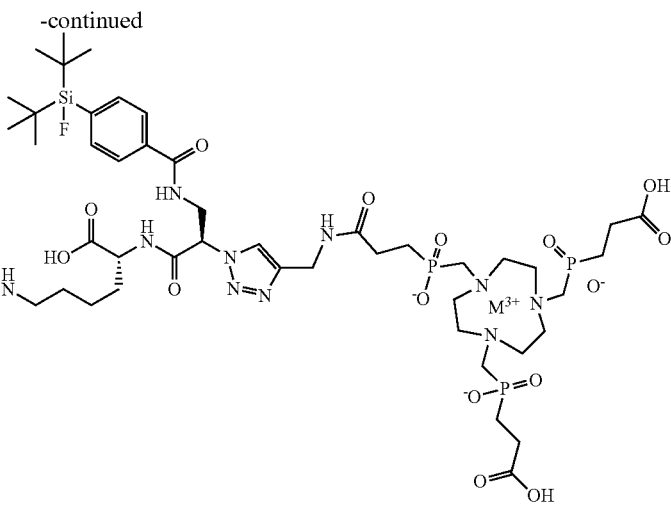
-continued
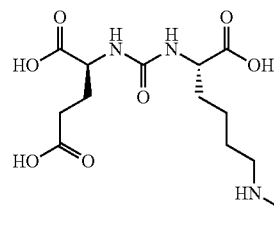
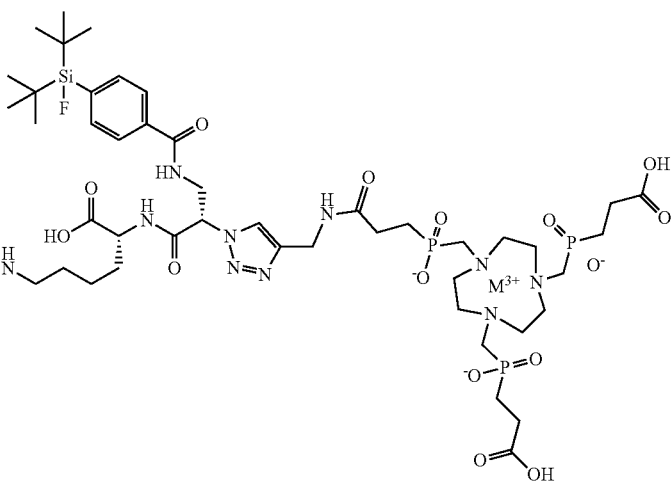
PSMA-SIFA3 (7)
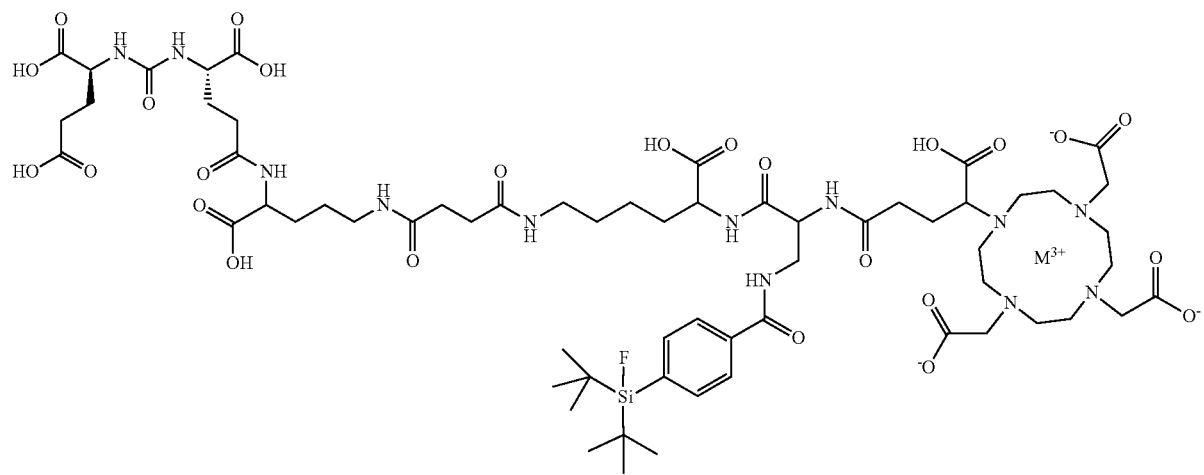

and isomers thereof
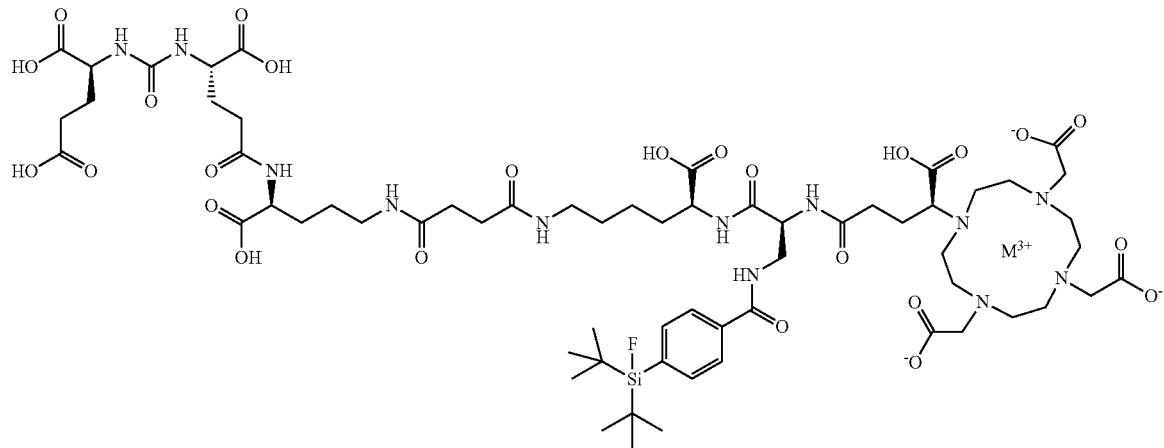
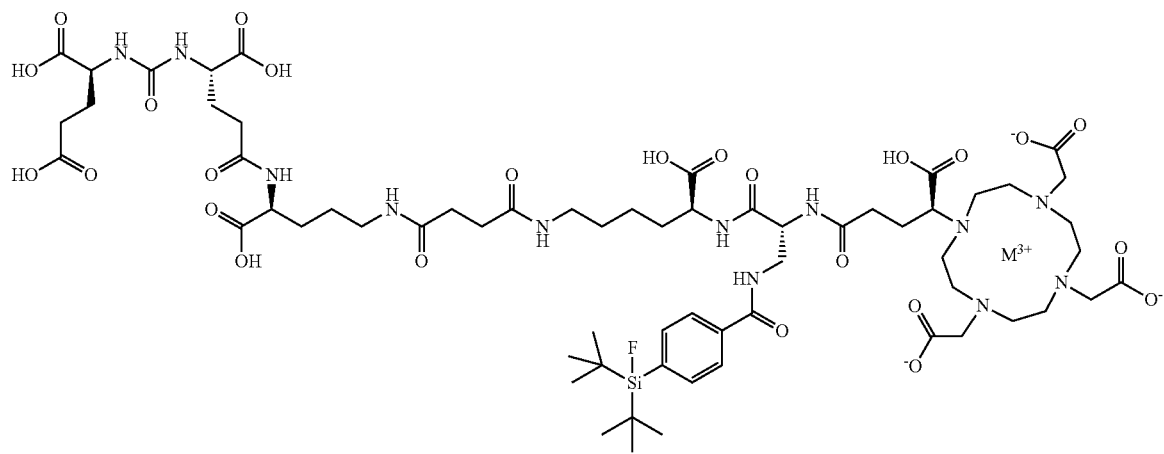
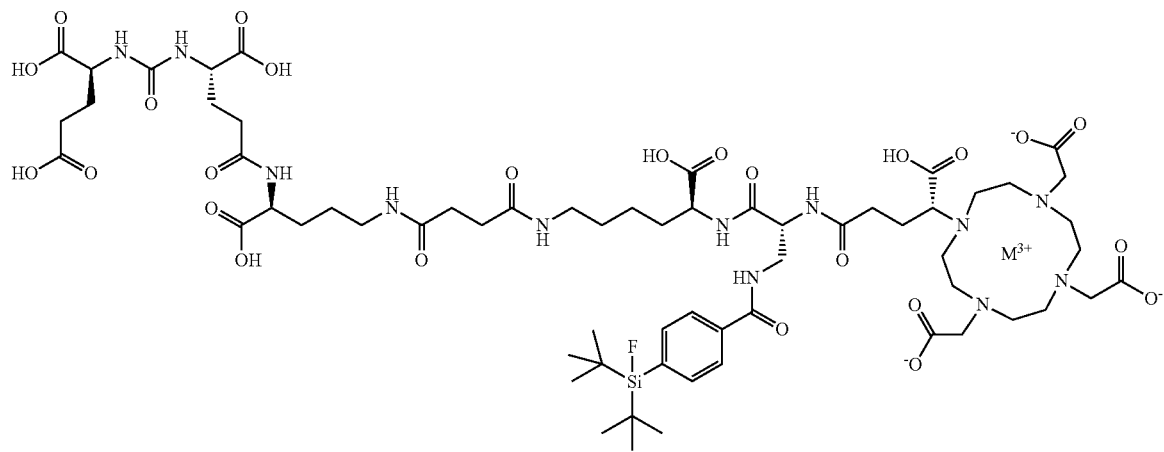

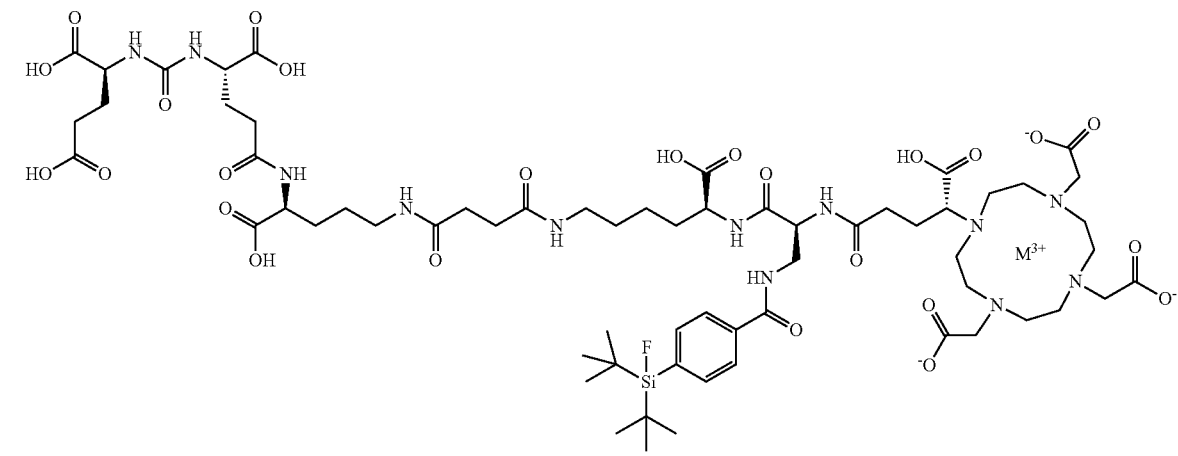
lp;4p
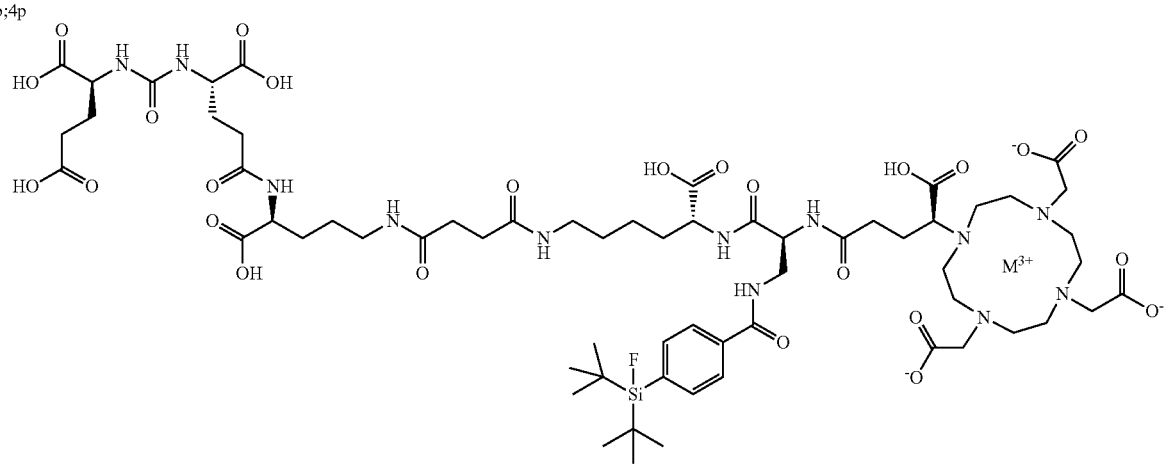
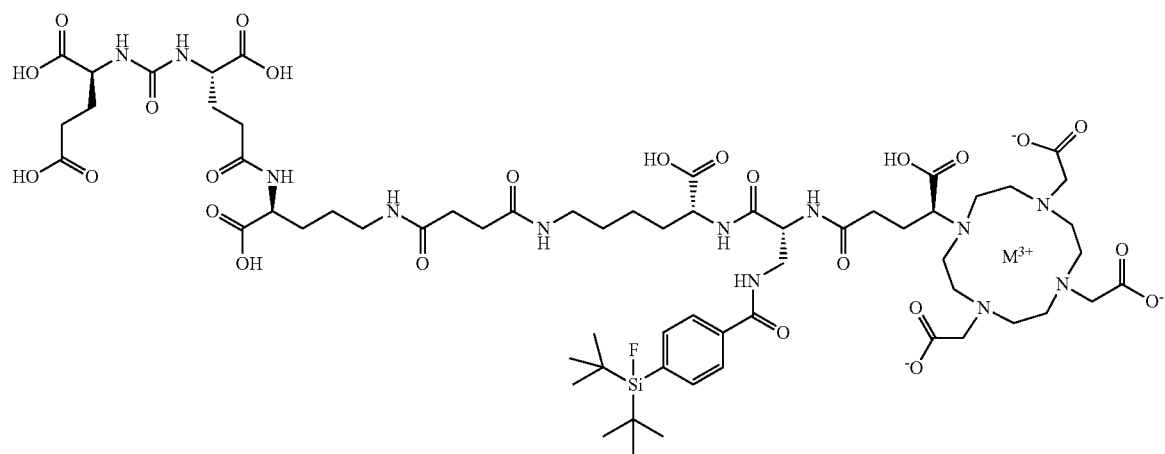

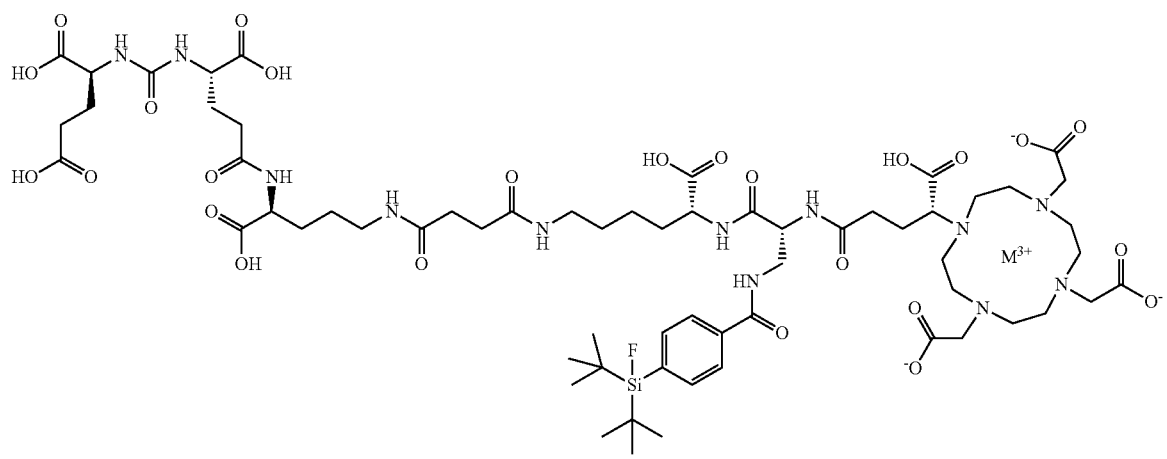
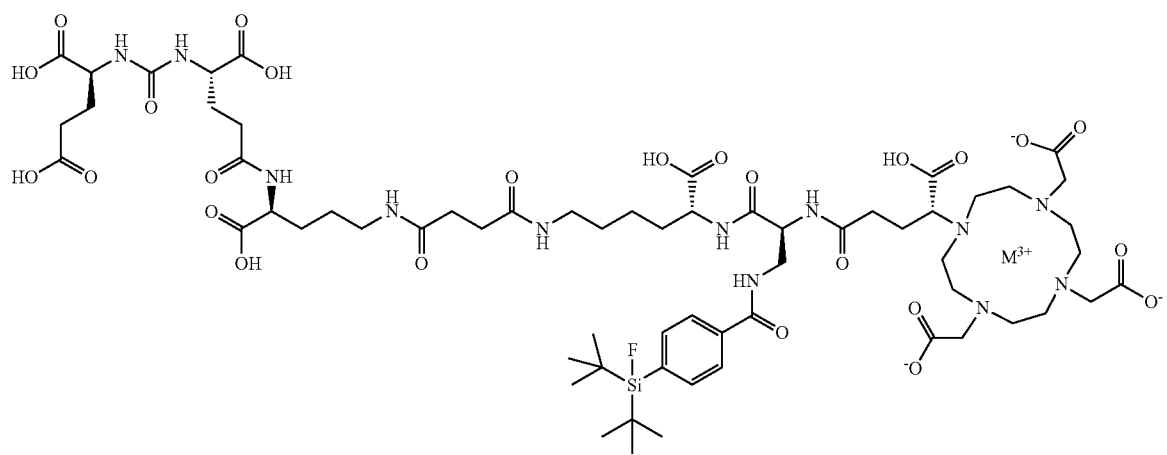
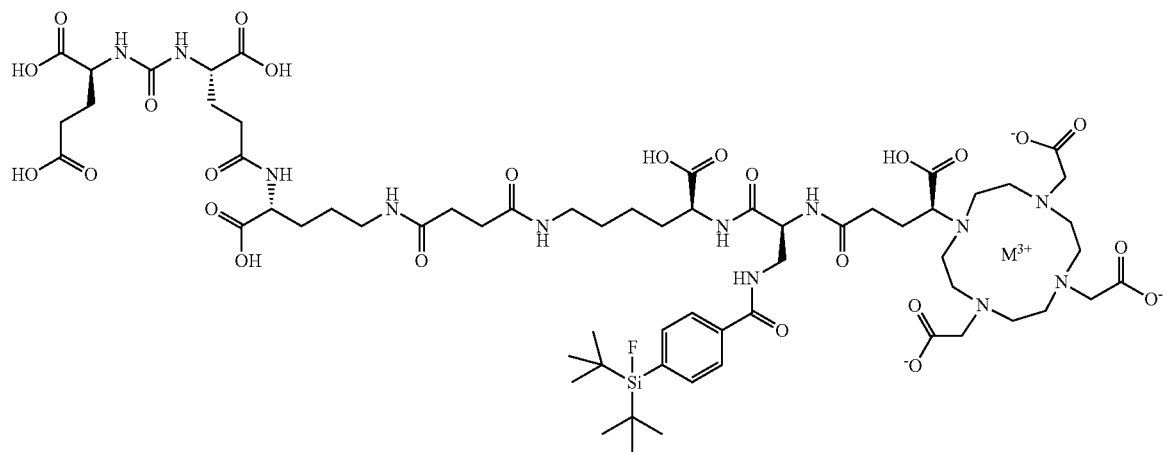

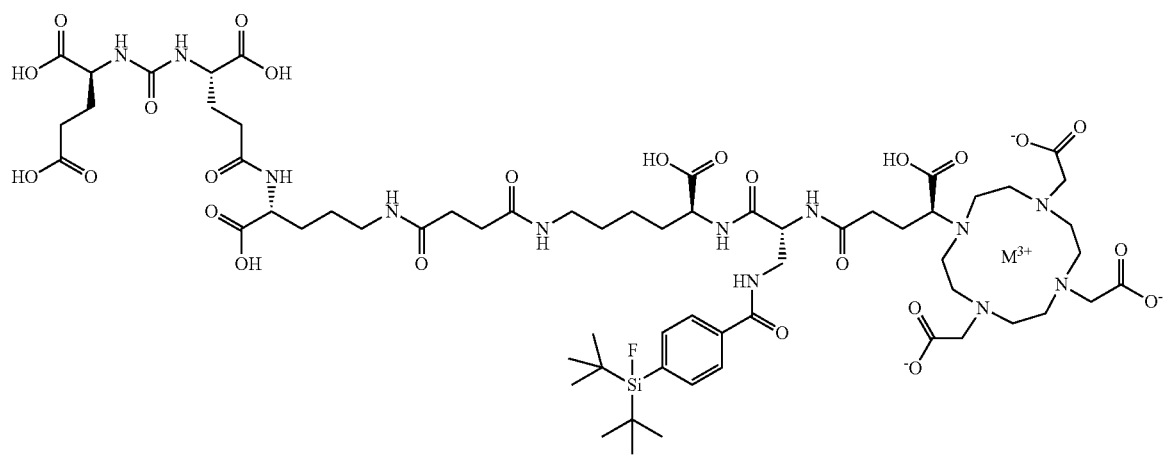
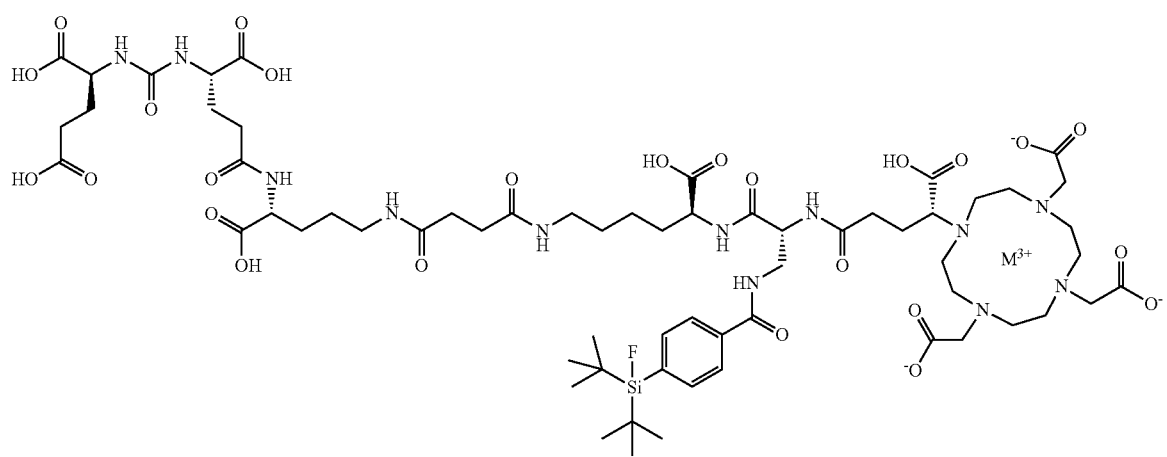
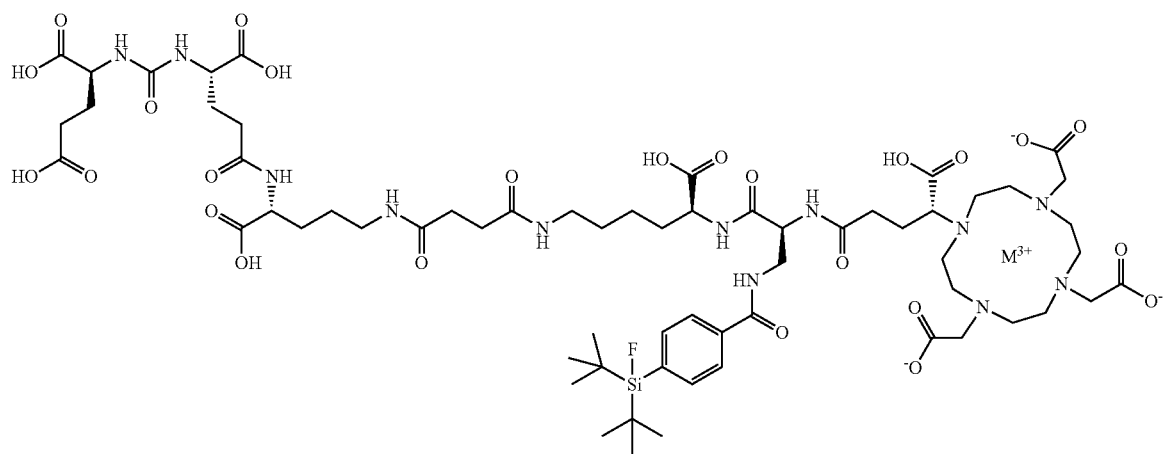

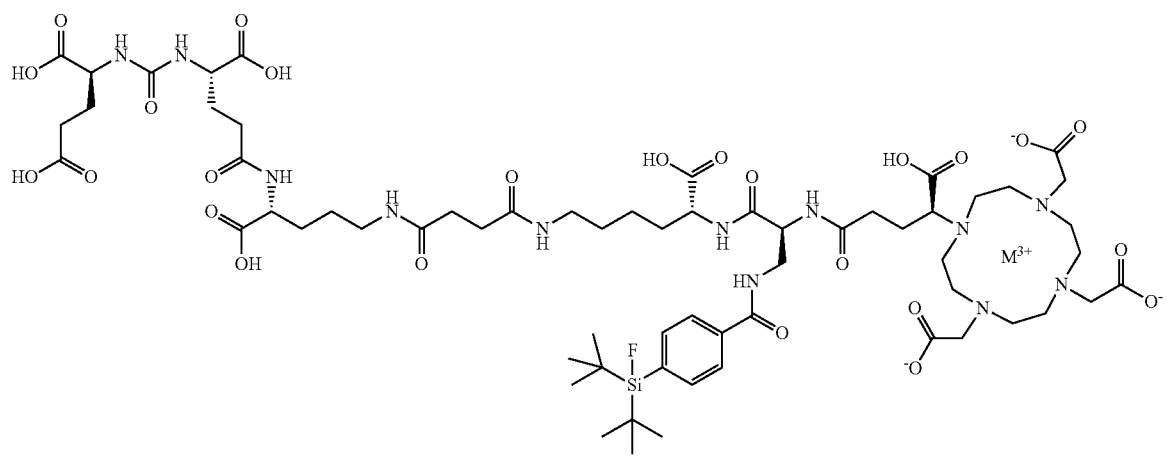
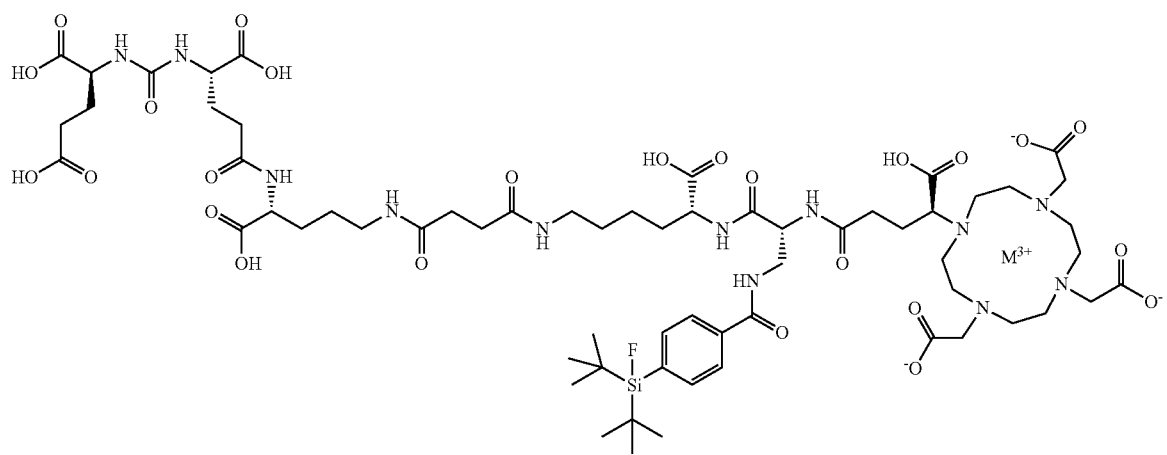
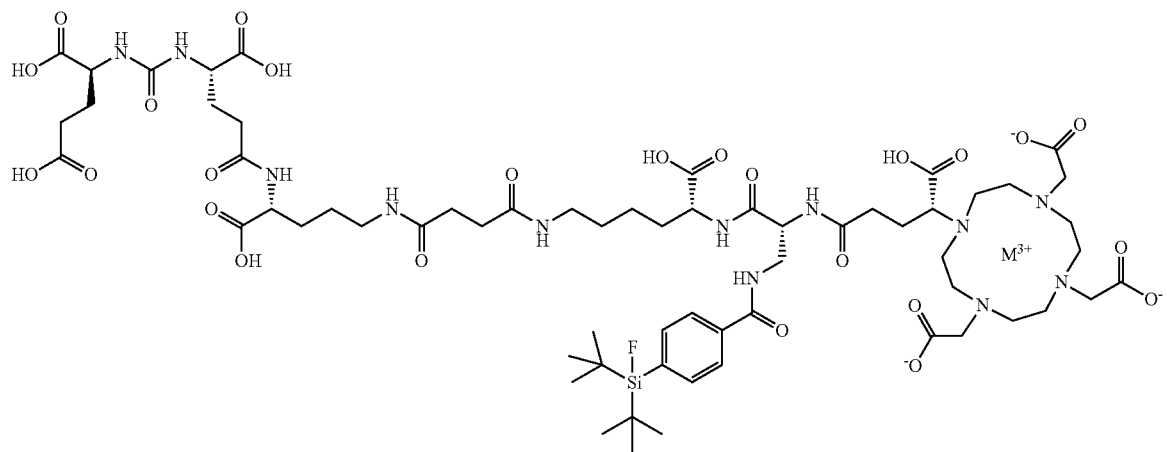

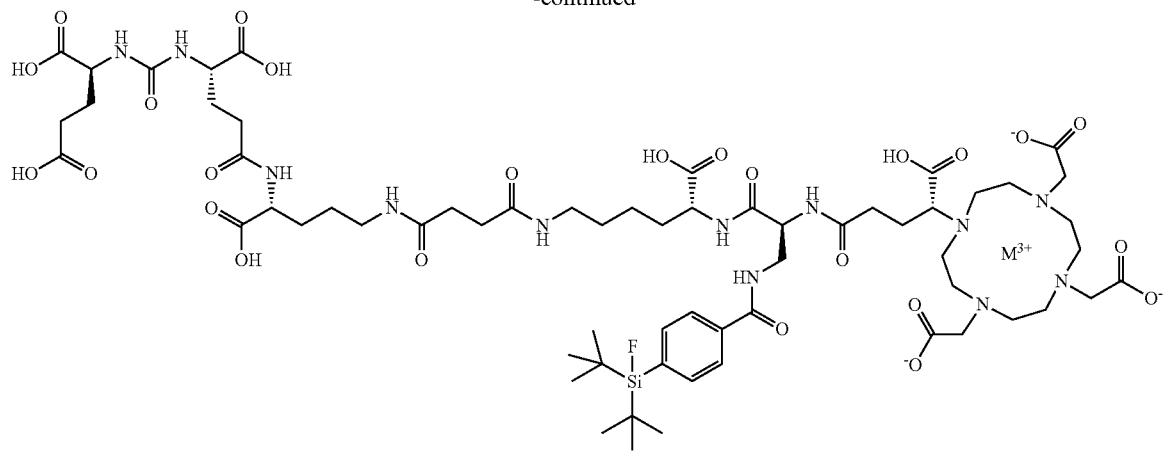
20
PSMA-SIFA4 (8)
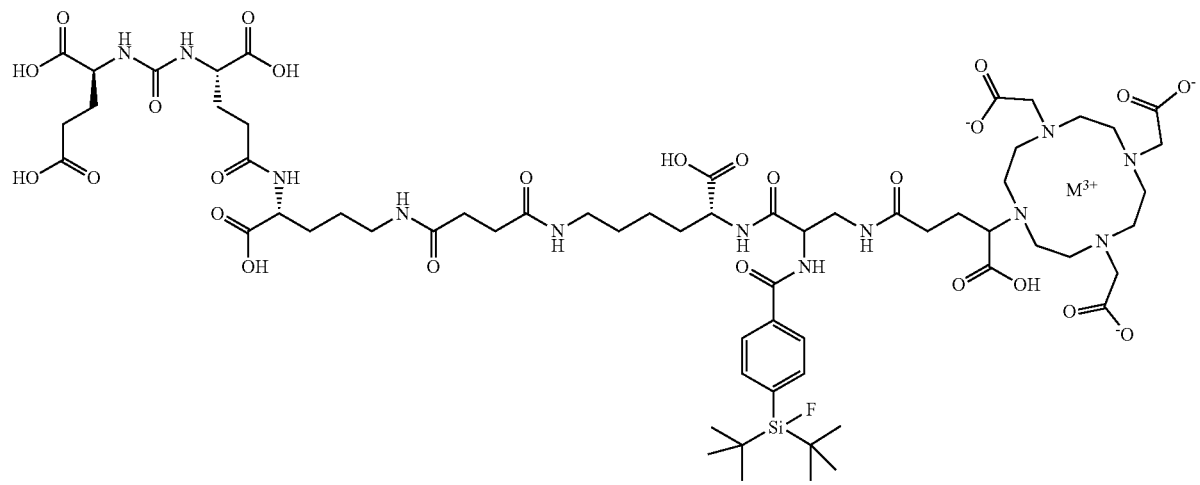
and isomers thereof
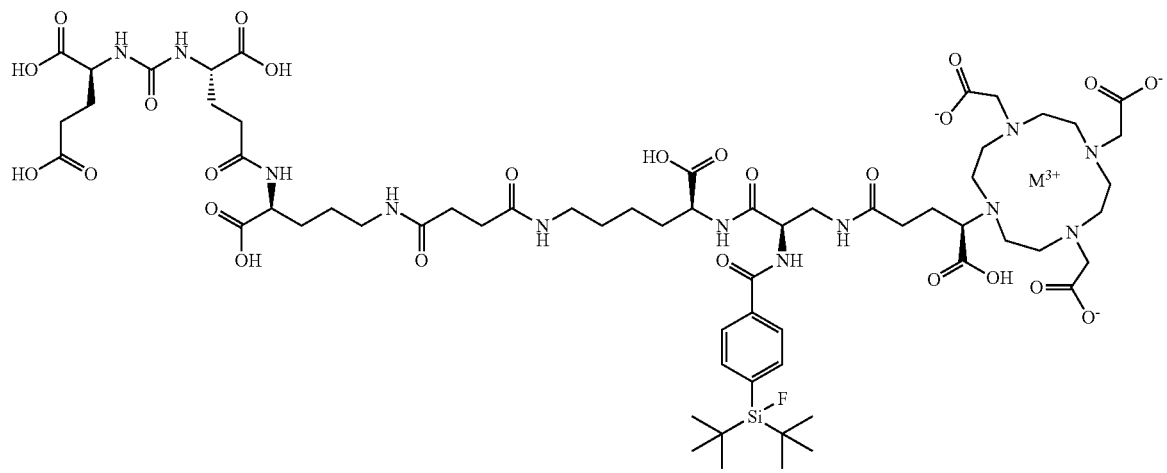

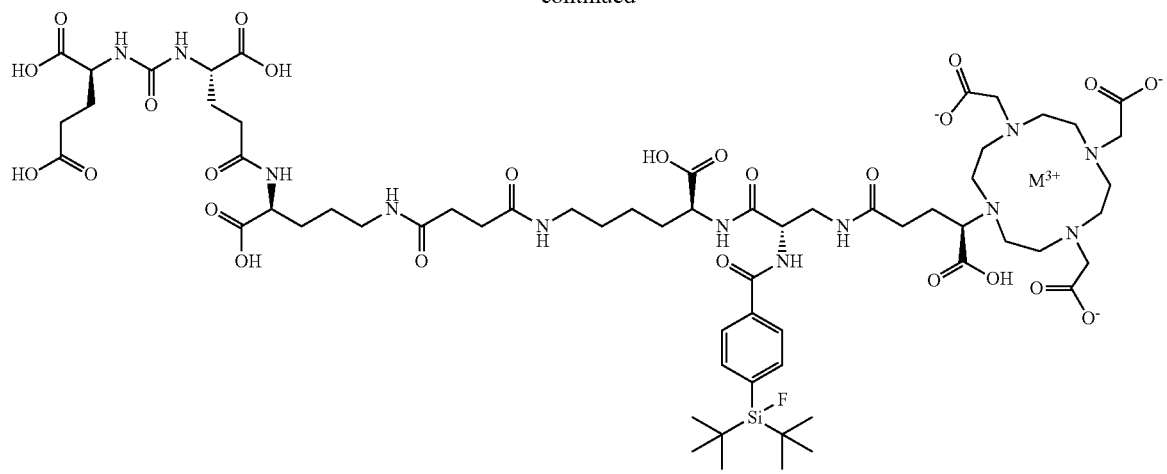
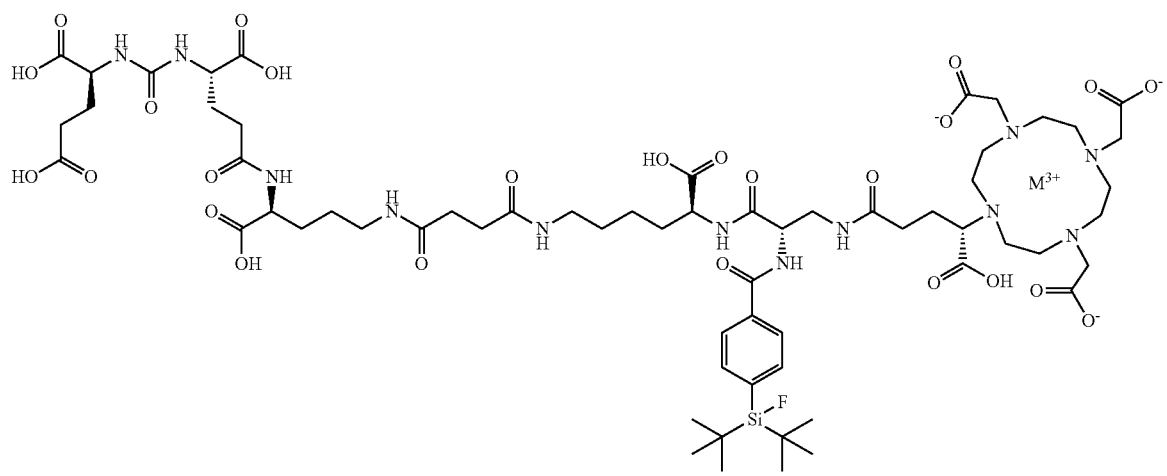
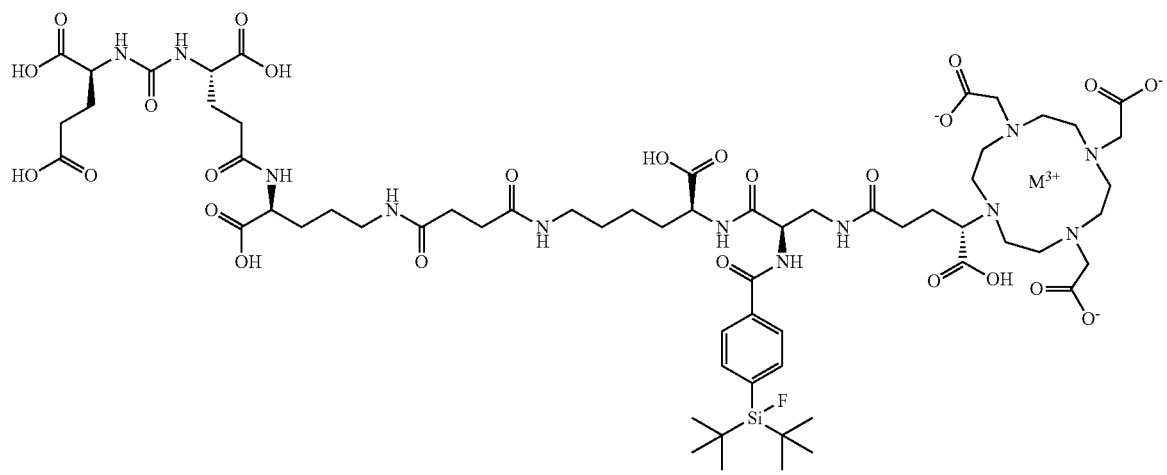

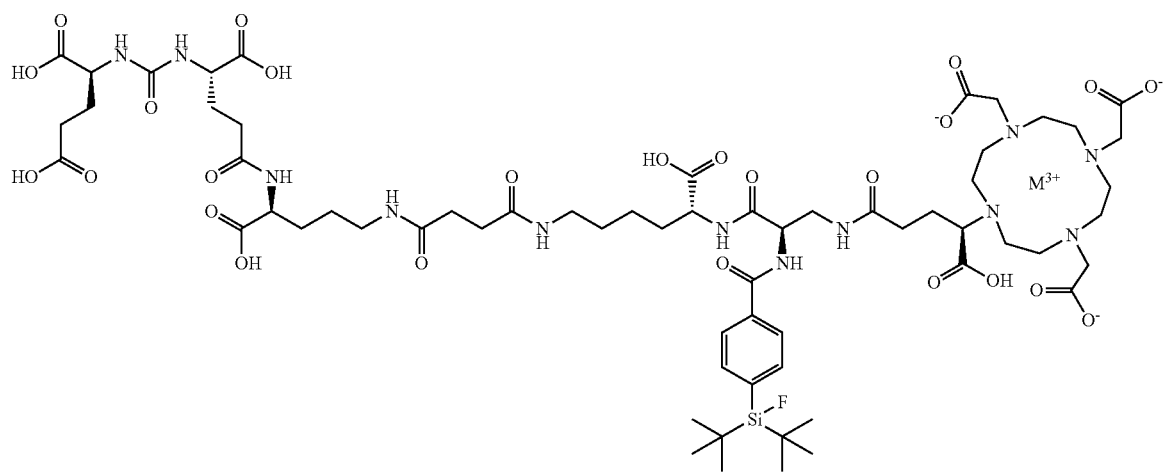
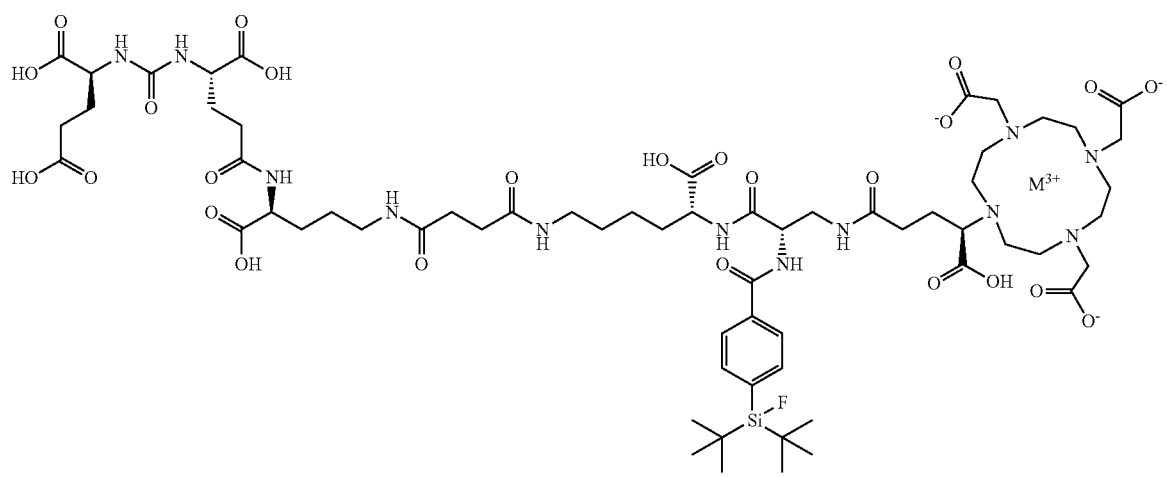
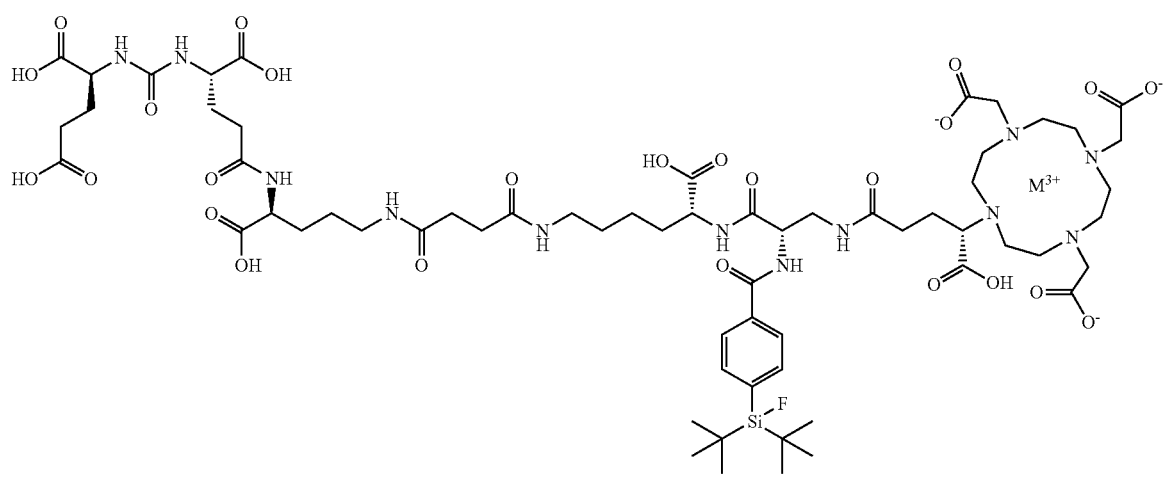

-continued
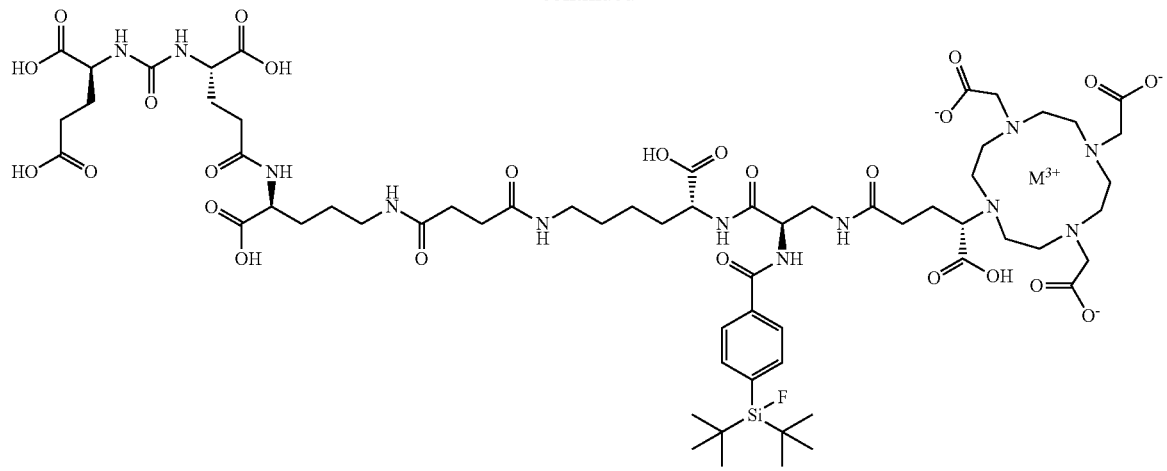
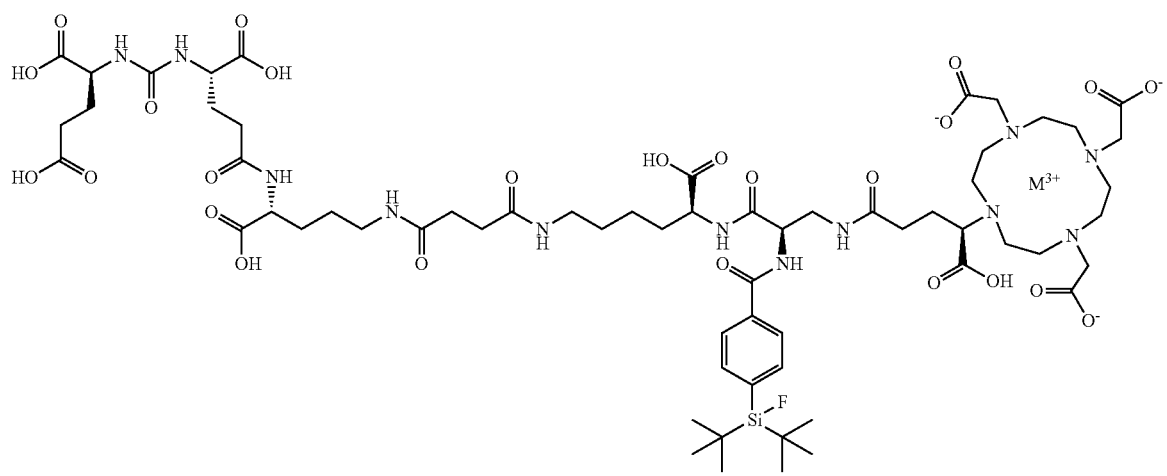
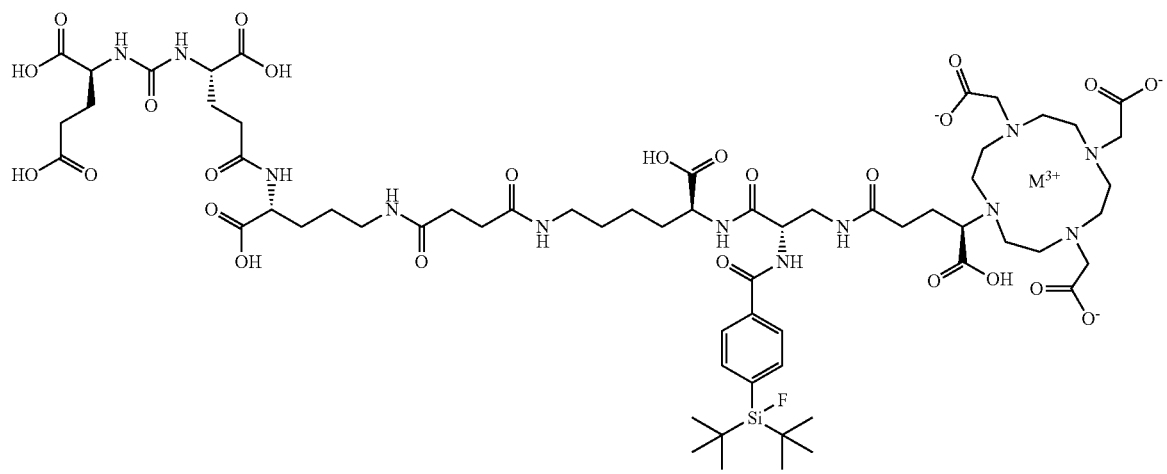

-continued
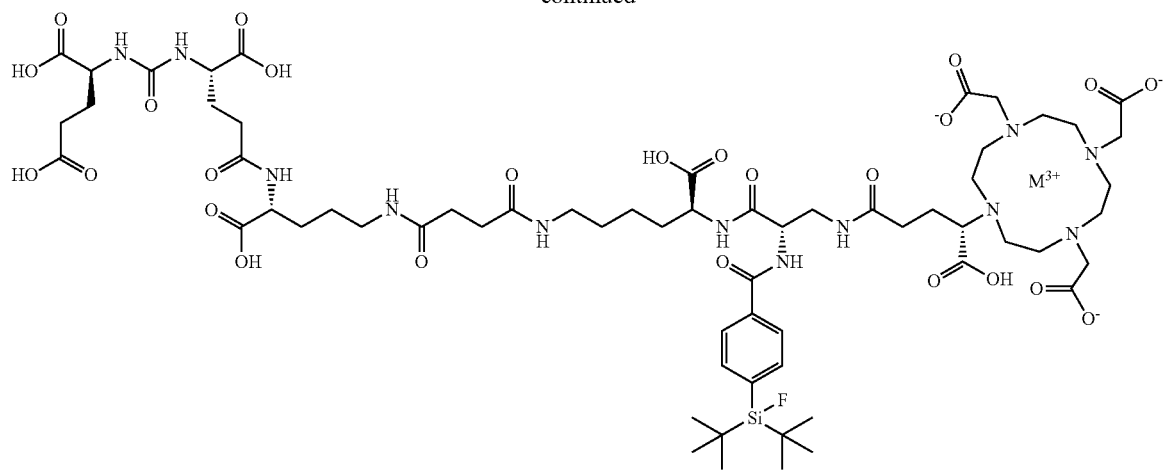
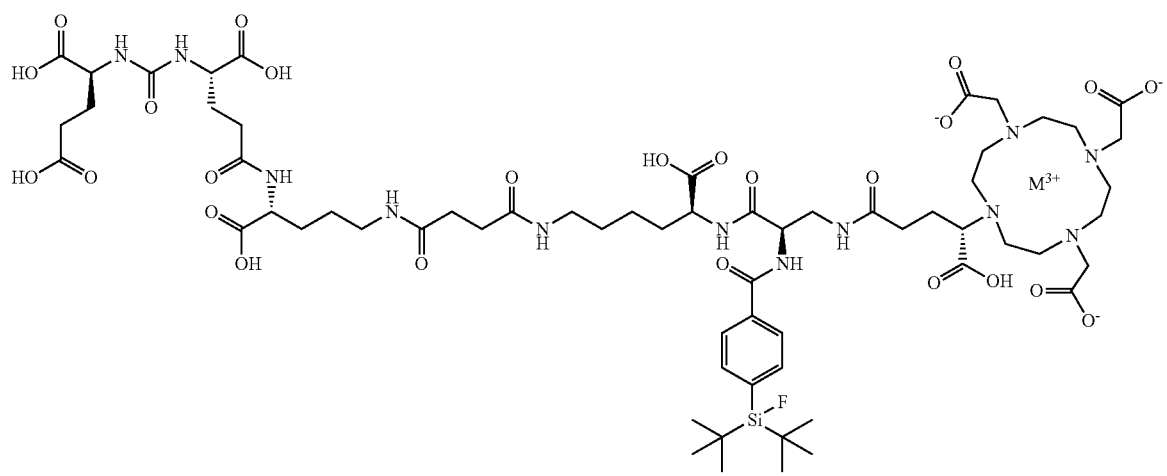
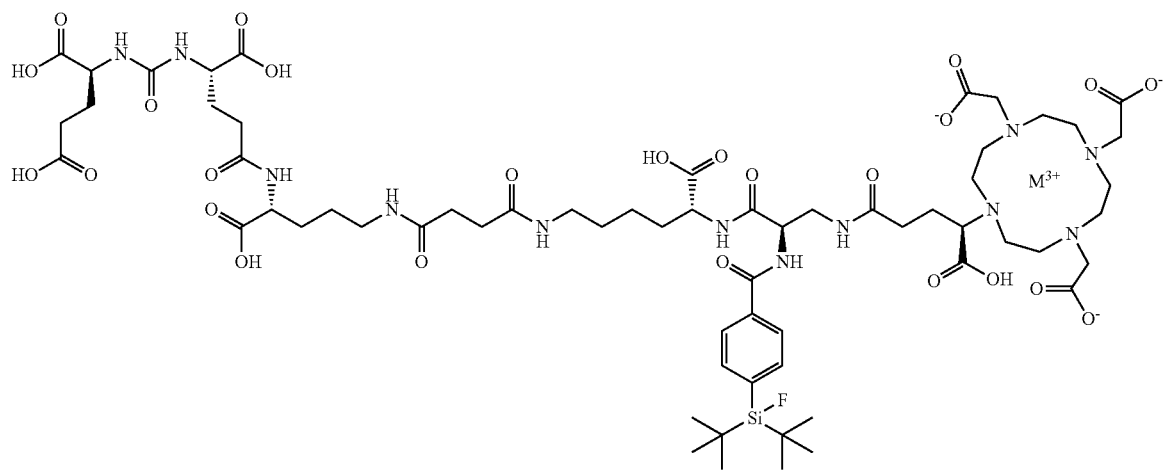

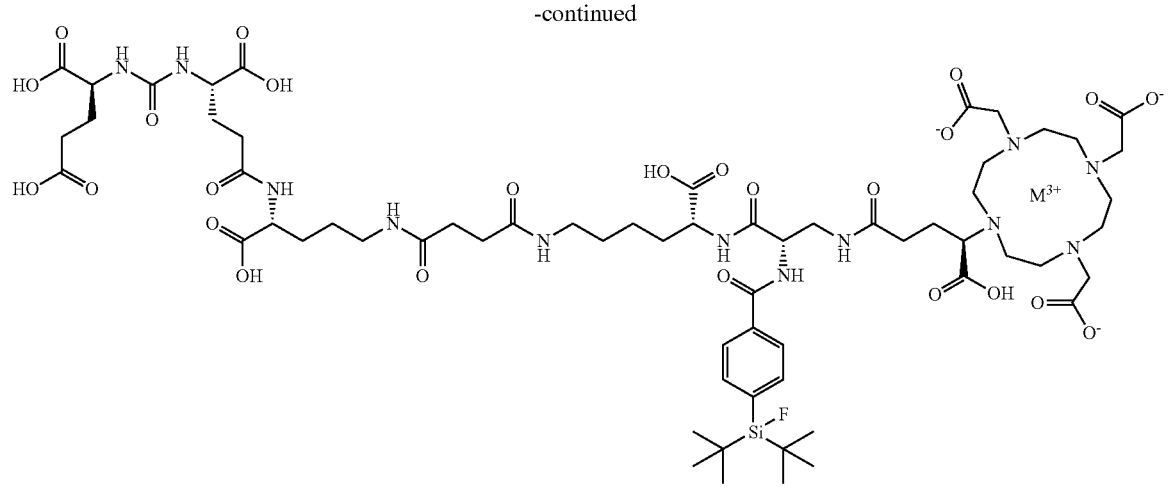
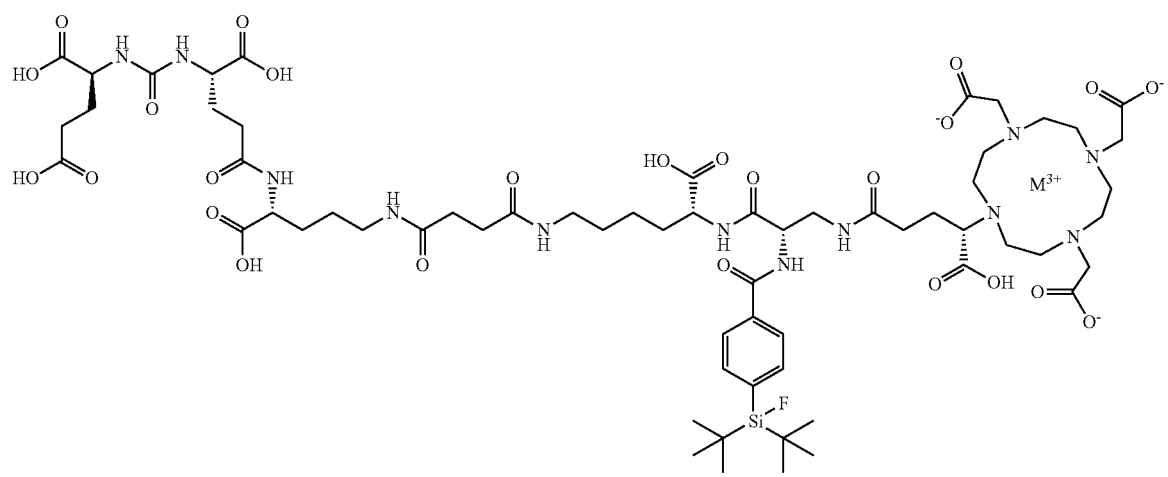
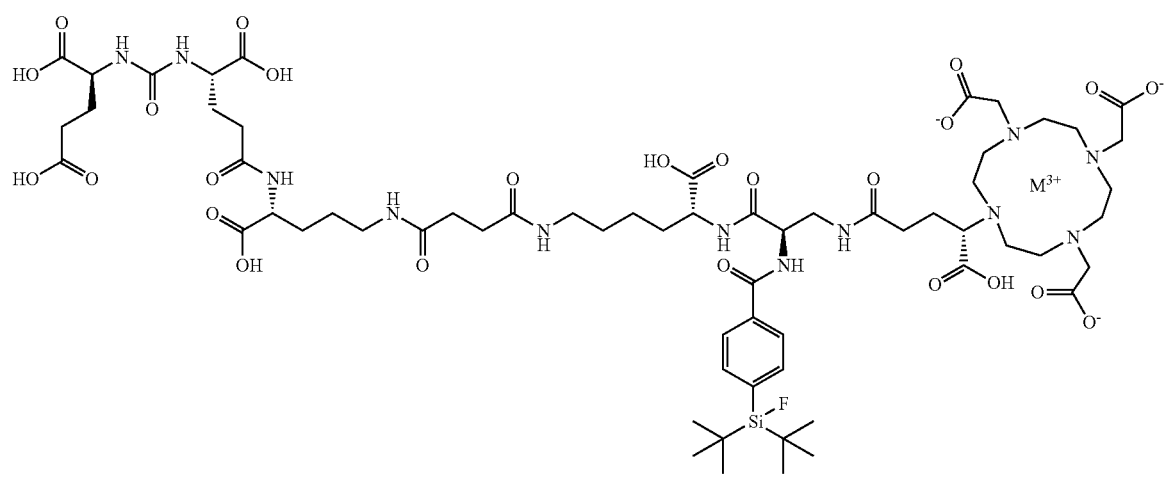

PSMA-SIFA5 (9)
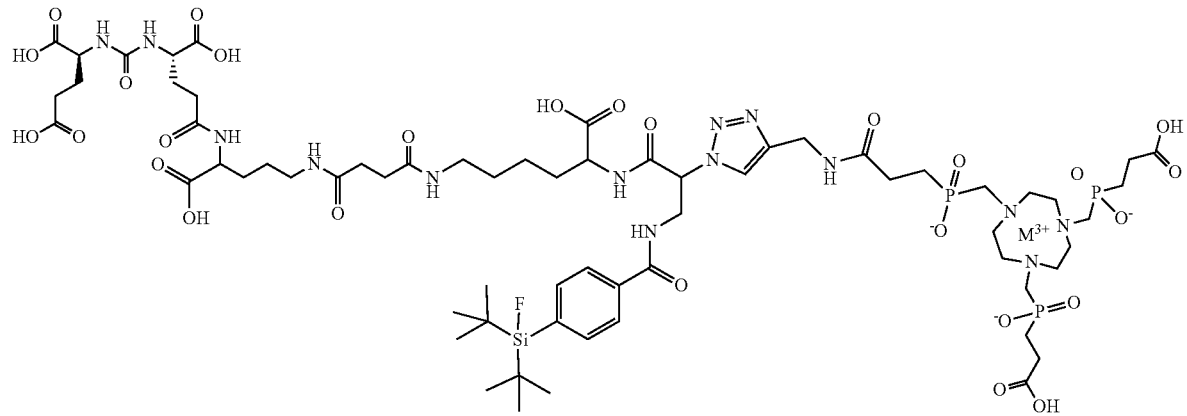
and isomers thereof
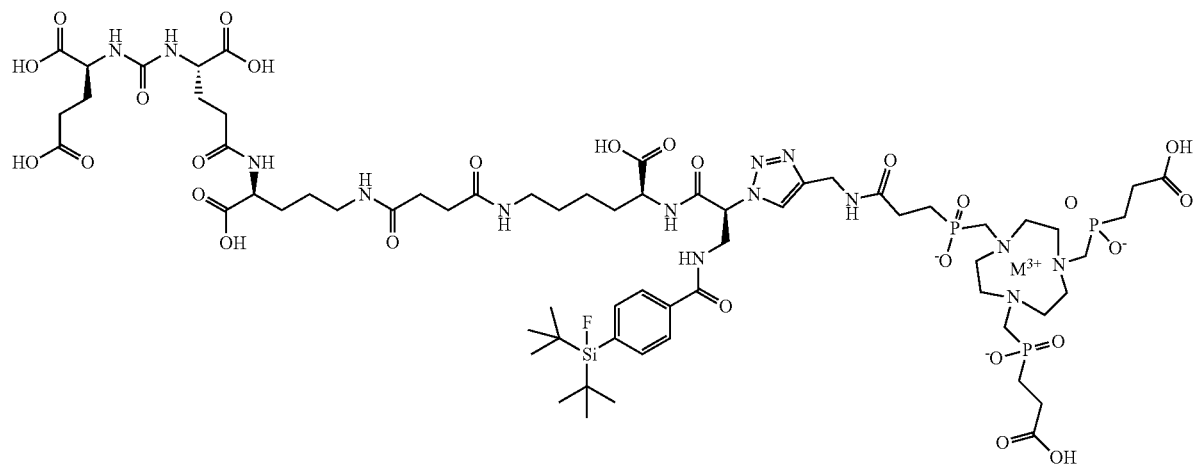
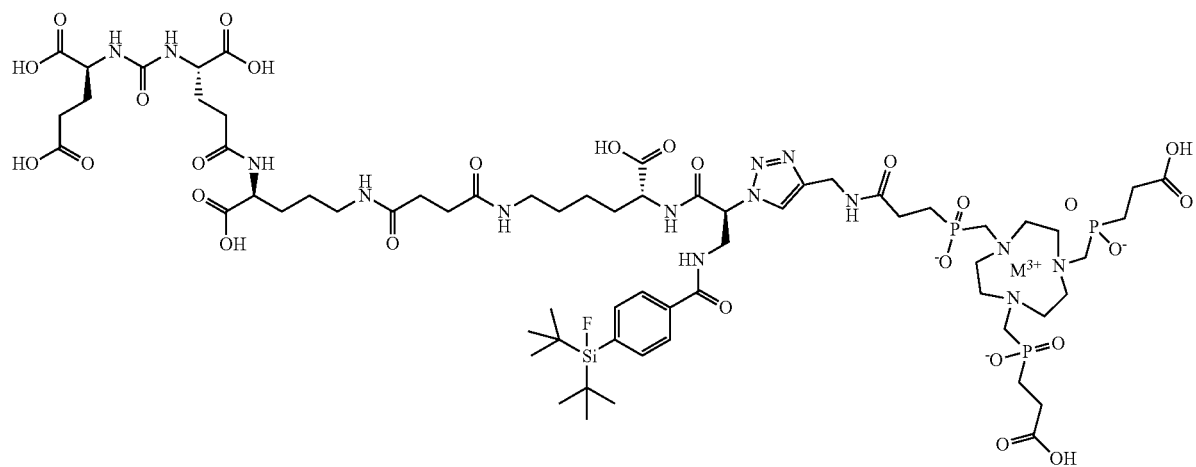

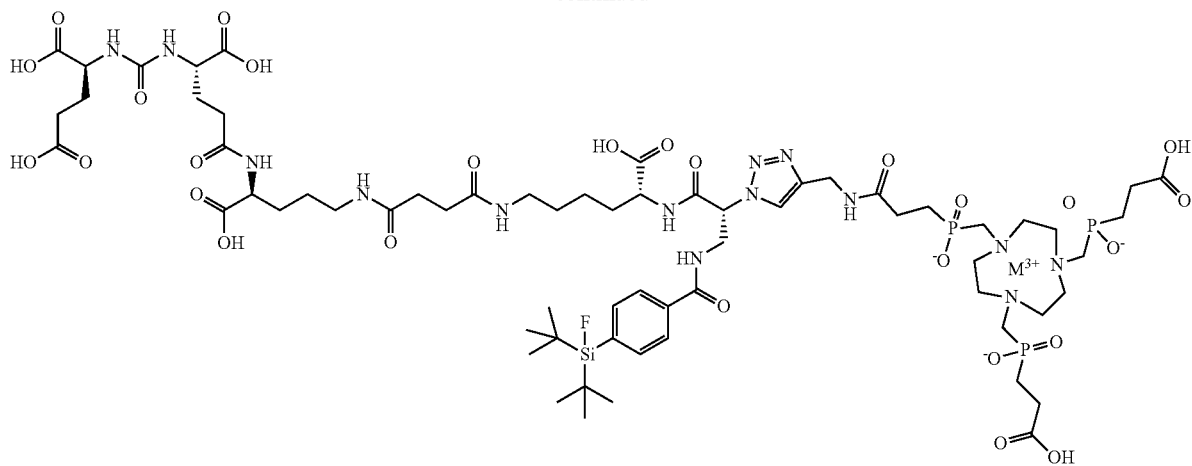
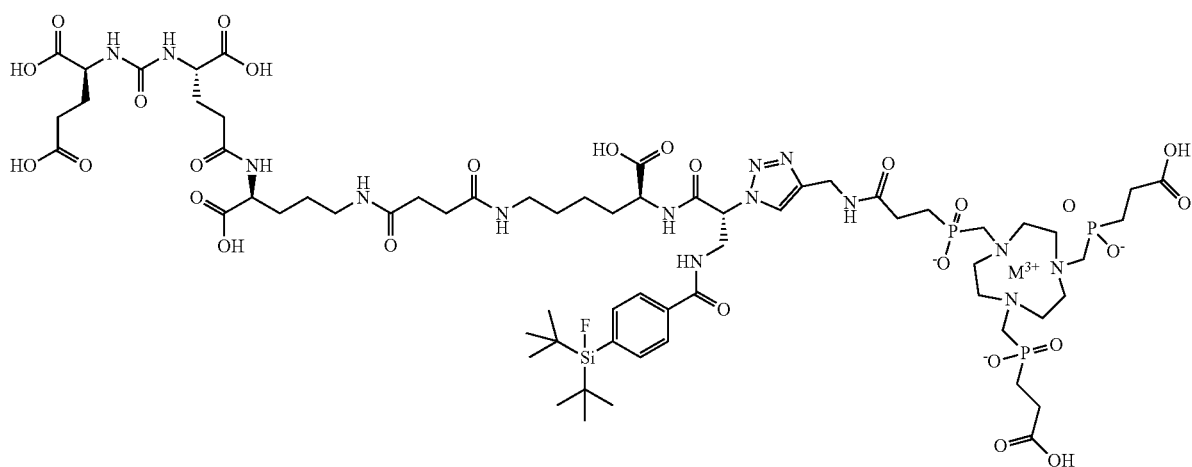
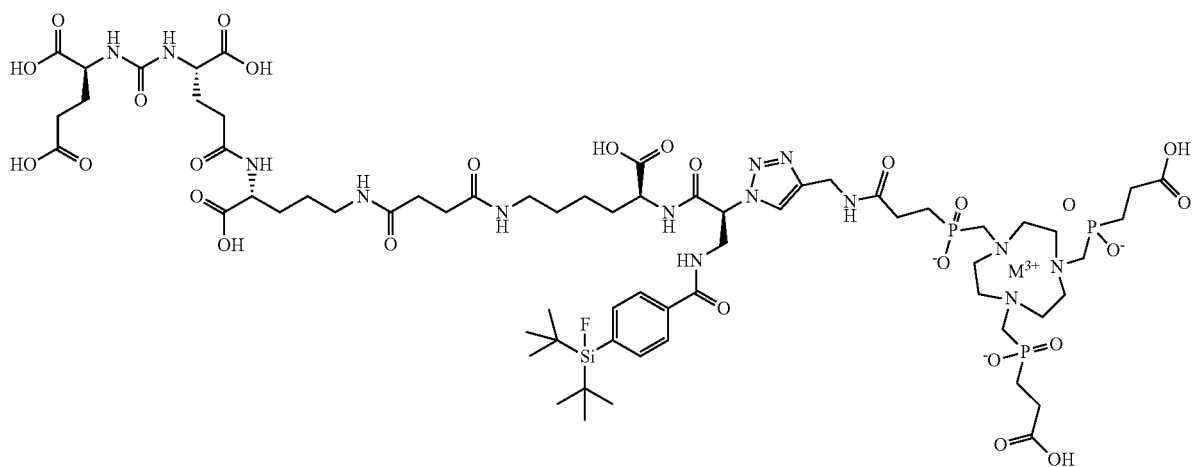

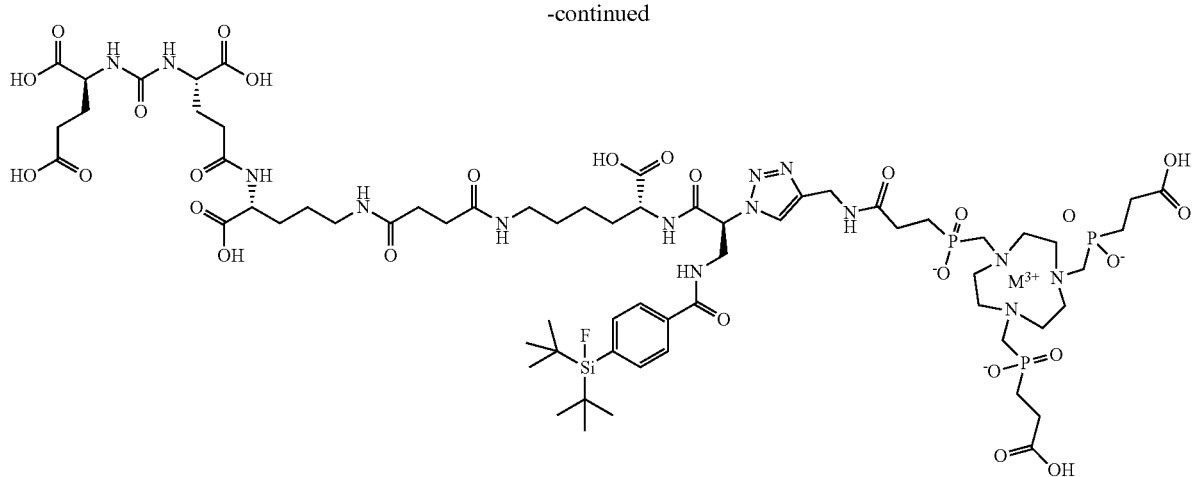
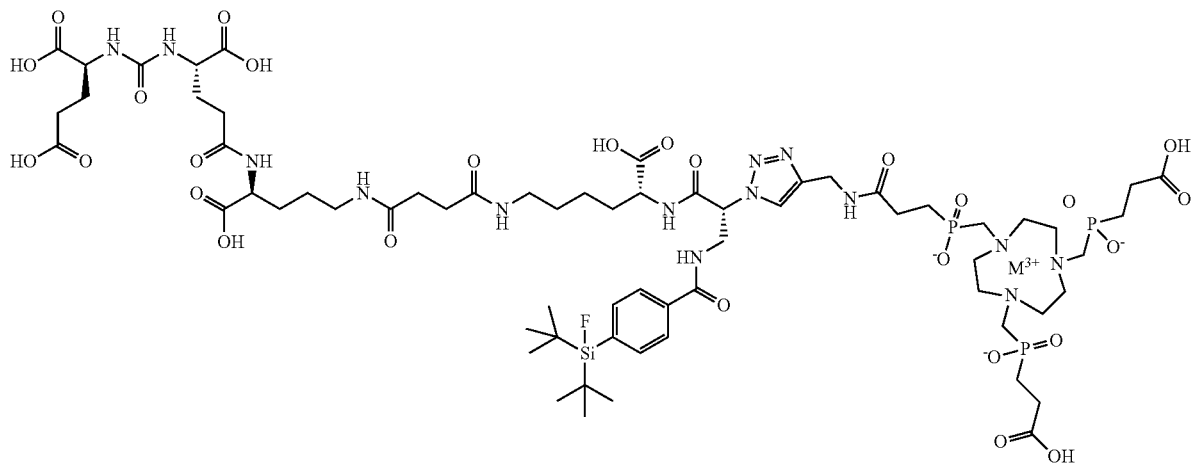
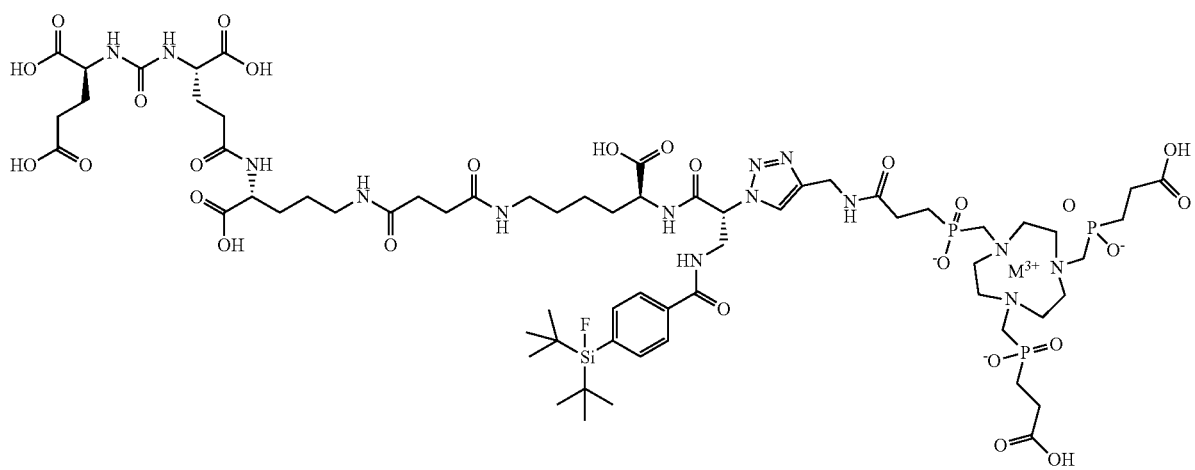

PSMA-SIFA 10
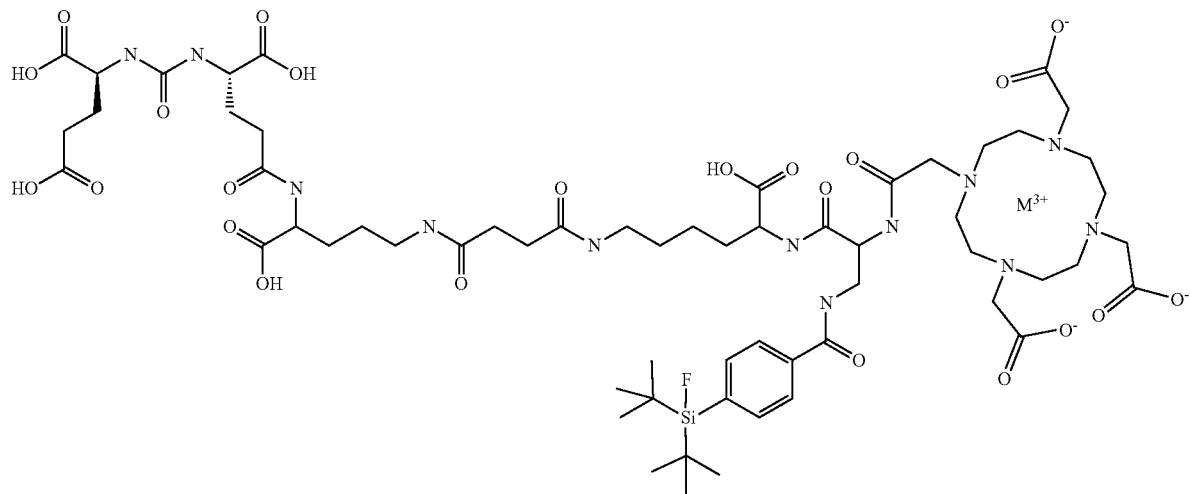 [SMILES: CC(C)(C)[Si](F)(c1ccc(C(=O)NCC(NC(=O)CN2CCN(CC(=O)[O-])CCN(CC(=O)[O-])CCN(CC(=O)[O-])CC2)C(=O)NC(CCCCNC(=O)CCC(=O)NCCCC(NC(=O)CC[C@H](NC(=O)N[C@@H](CCC(=O)O)C(=O)O)C(=O)O)C(=O)O)C(=O)O)cc1)C(C)(C)C ; "M3+"]
and isomers thereof:
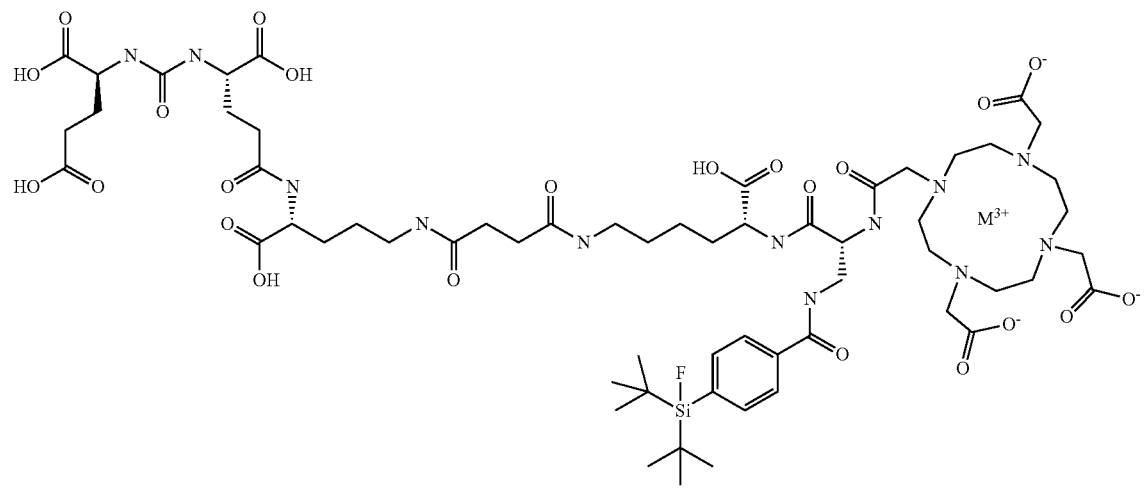
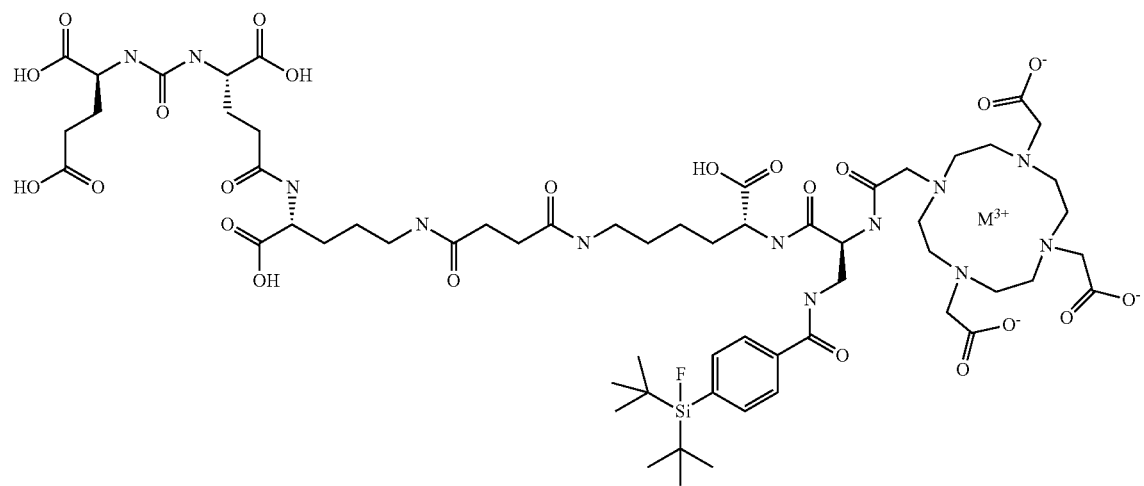

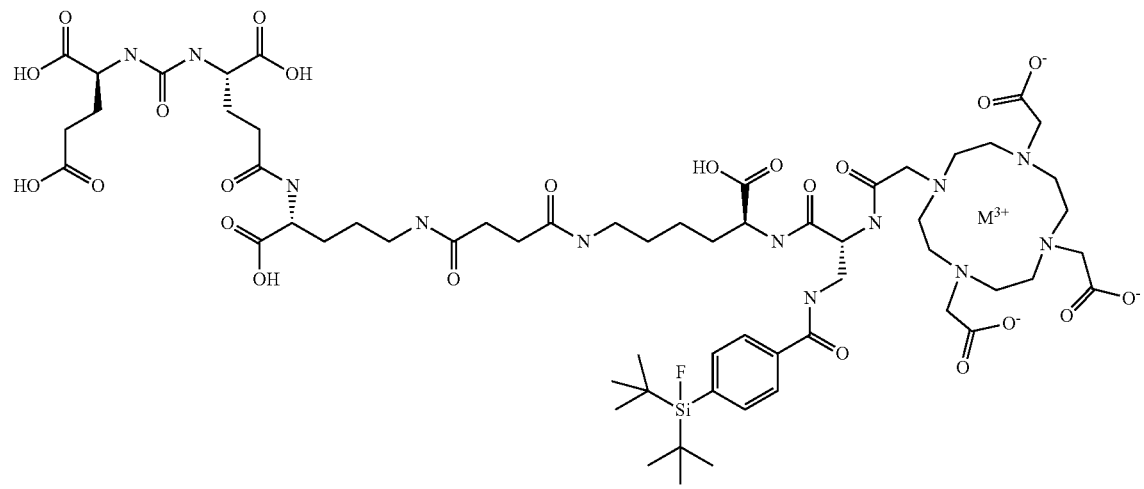
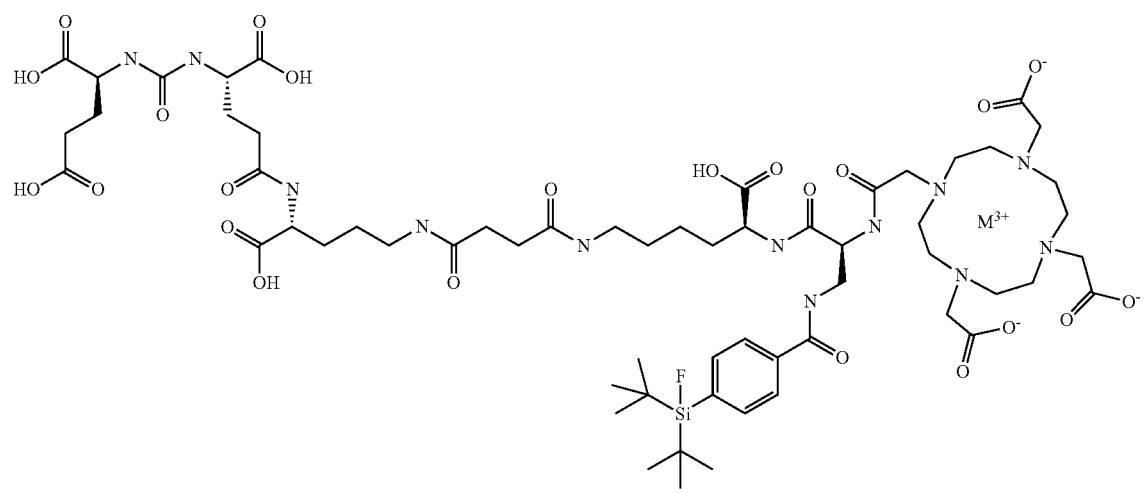
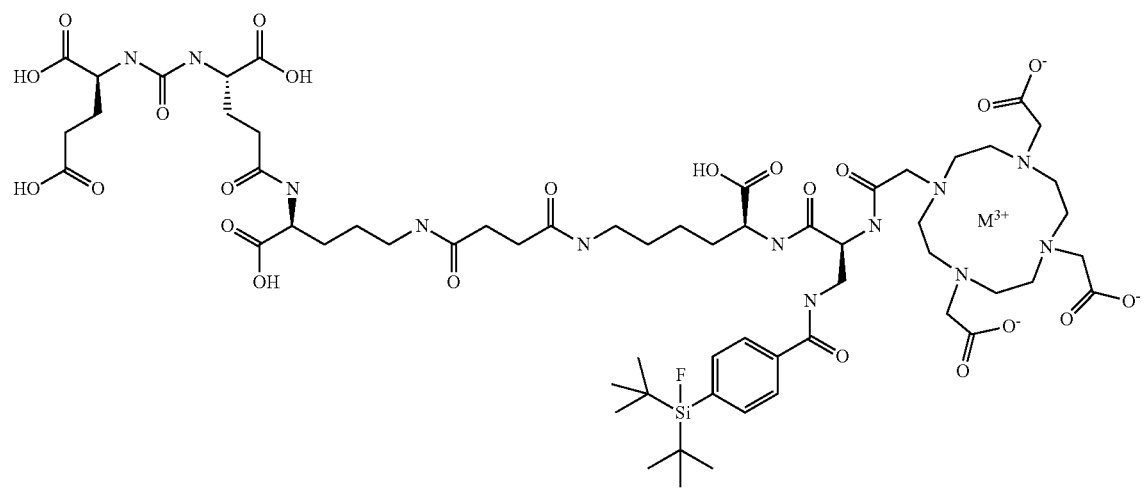

-continued
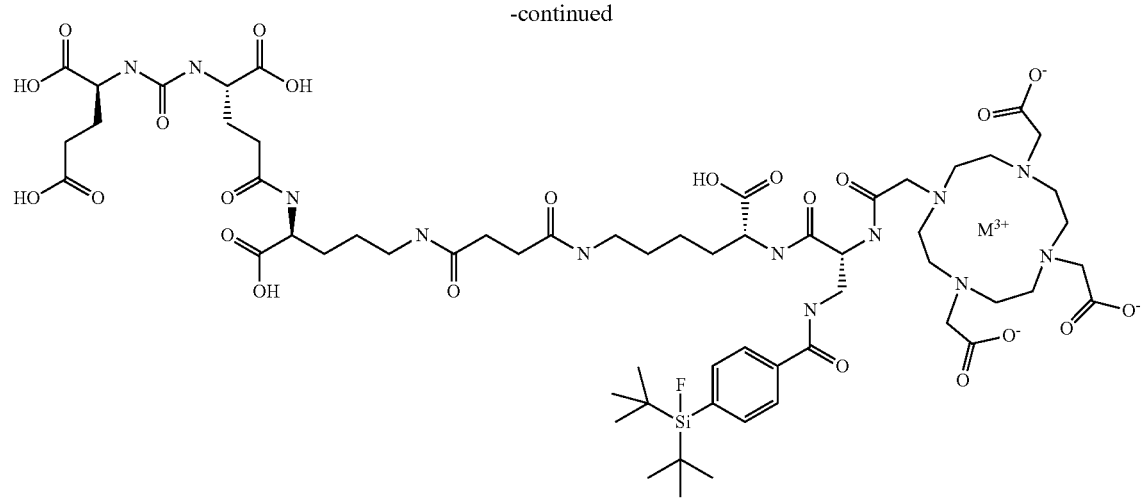
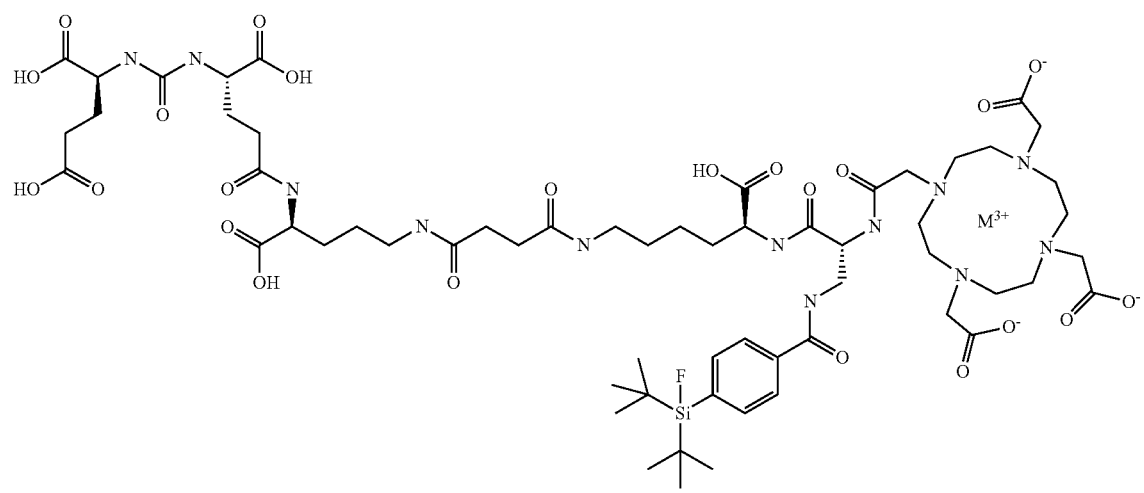
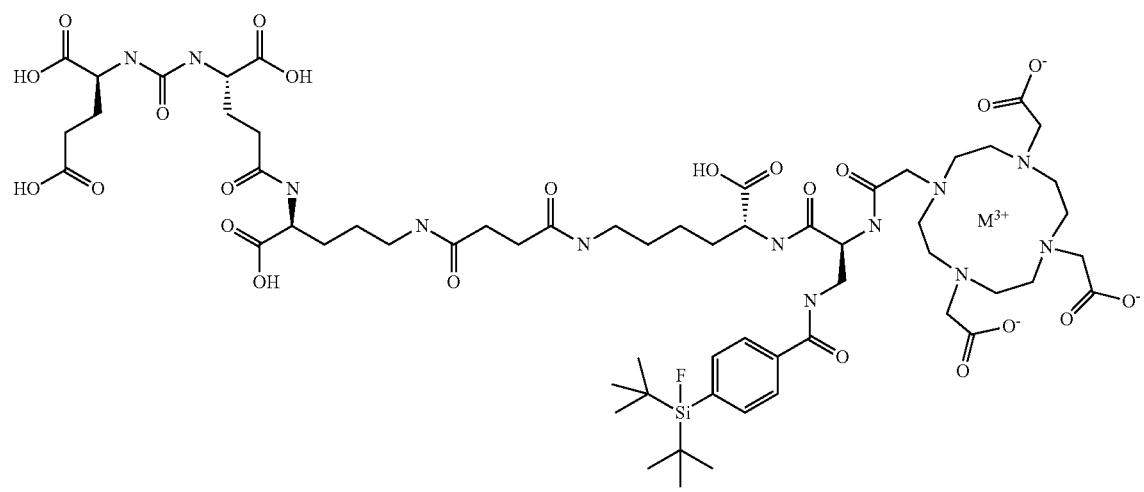

PSMA-SIFA 11
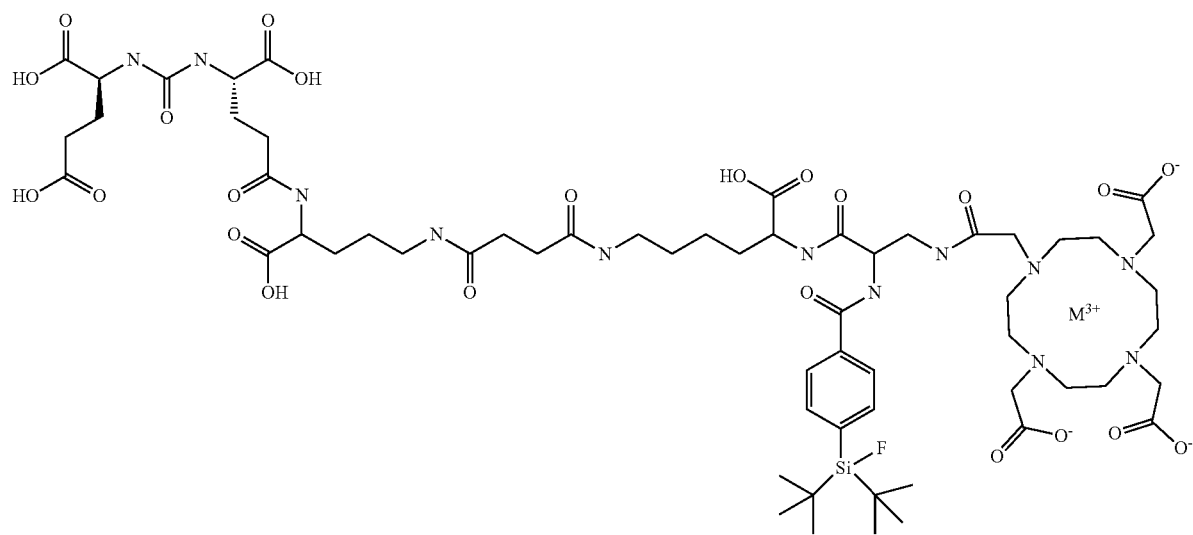 [SMILES: CC(C)(C)[Si](F)(c1ccc(C(=O)NC(CNC(=O)CN2CCN(CC(=O)[O-])CCN(CC(=O)[O-])CCN(CC(=O)[O-])CC2)C(=O)NC(CCCCNC(=O)CCC(=O)NCCCC(NC(=O)CC[C@H](NC(=O)N[C@@H](CCC(=O)O)C(=O)O)C(=O)O)C(=O)O)C(=O)O)cc1)C(C)(C)C ; "M3+"]
and isomers thereof:
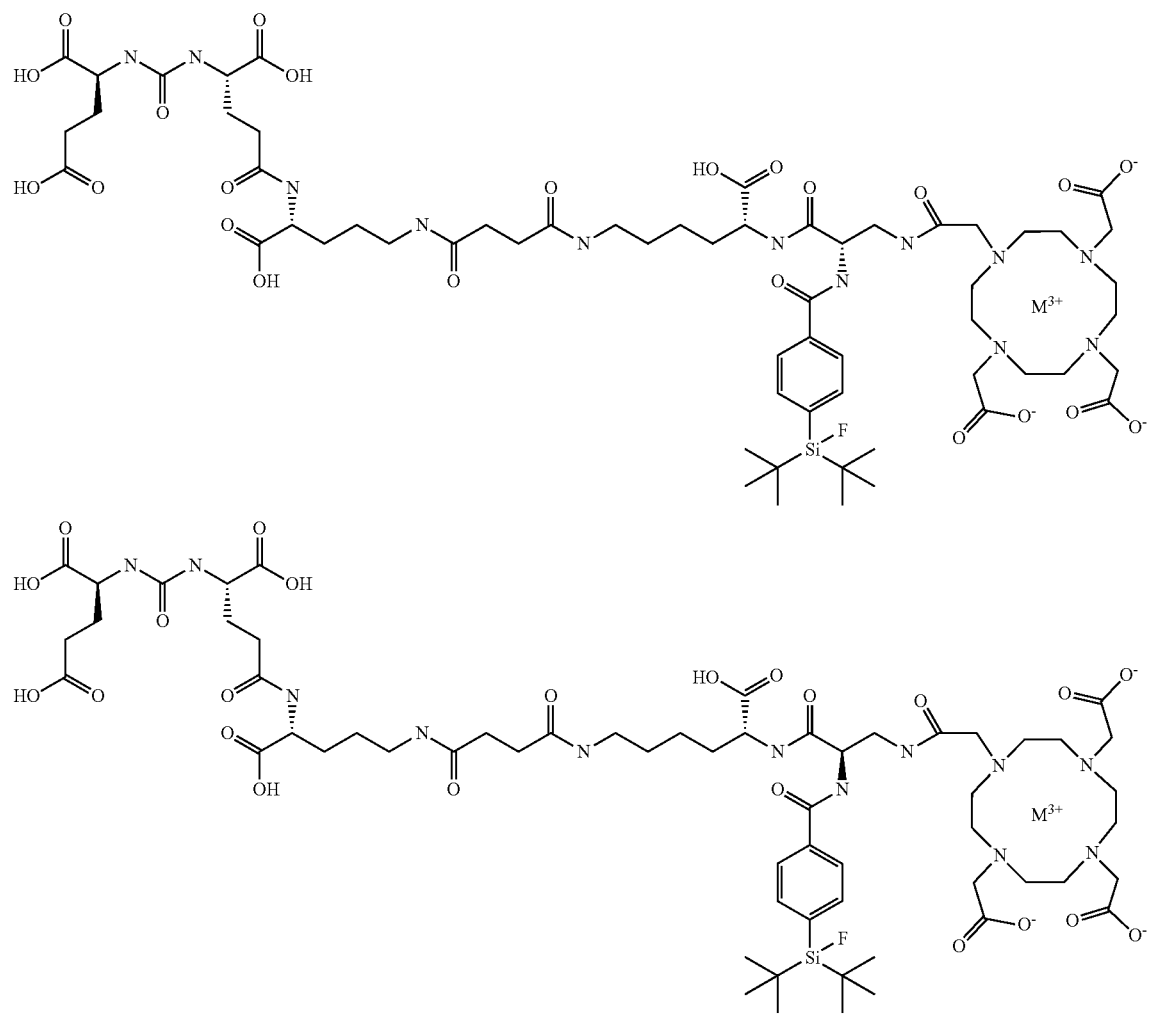

-continued
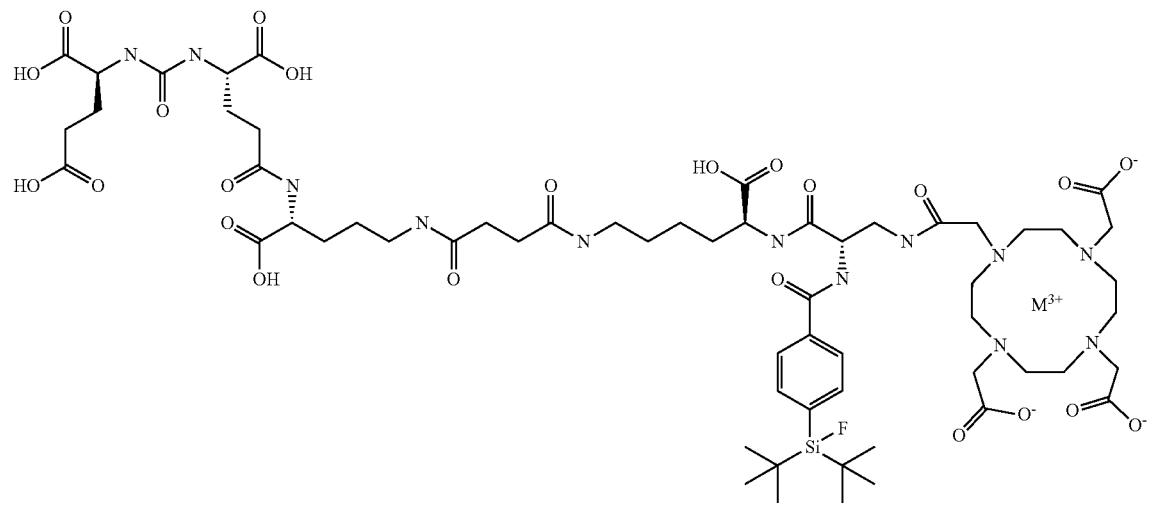
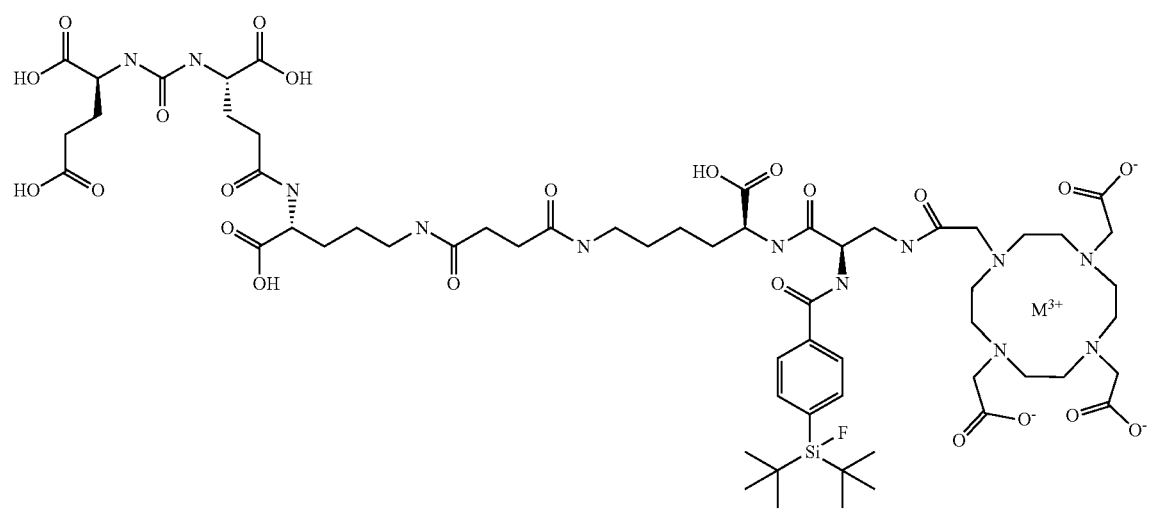
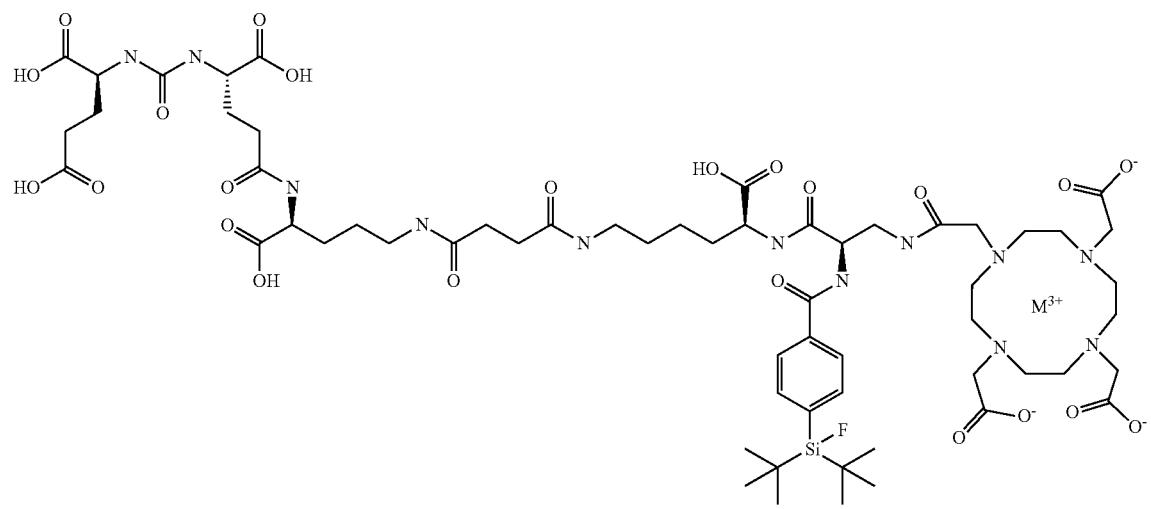

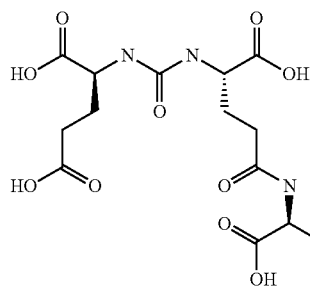
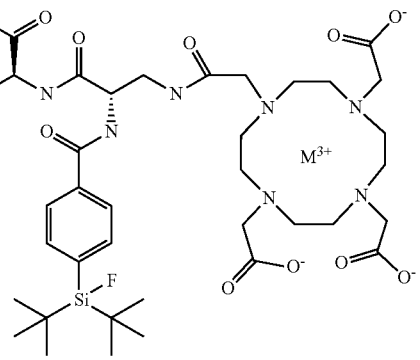
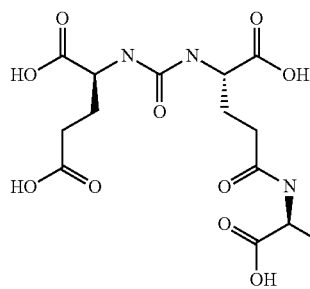
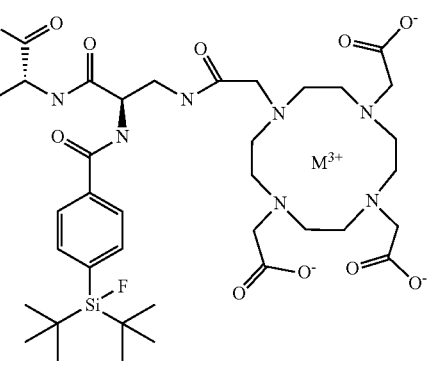
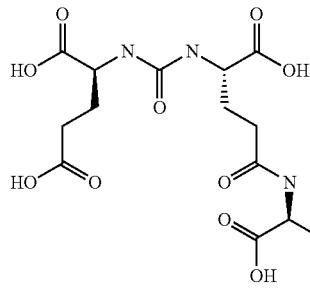
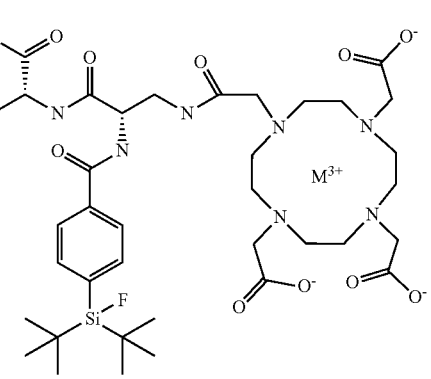

Preferred labelling schemes for these most preferred radiohybrids of the compositions are as defined herein above.

The term 'pharmaceutical composition' refers to a composition comprising a pharmaceutical together with a biocompatible carrier in a form suitable for mammalian administration. A 'biocompatible carrier' is a fluid, especially a liquid, in which a pharmaceutical is suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection or an aqueous solution such as saline.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter may be present in amounts between 0.1 ng and 10 mg/kg body weight per dose; however, doses below or above this exemplary range are envisioned, especially considering the aforementioned factors.

In a further aspect, the present invention provides one or more compositions of the invention as disclosed herein above for use in diagnostic medicine.

Preferred uses in medicine are in nuclear medicine such as nuclear diagnostic imaging, also named nuclear molecular imaging, and/or targeted radiotherapy of diseases associated with an overexpression, preferably of PSMA on the diseased tissue.

In a further aspect, the present invention provides compositions of the invention as defined herein above for use in a method of diagnosing and/or staging cancer, preferably prostate cancer. Prostate cancer is not the only cancer to express PSMA. Nonprostate cancers to demonstrate PSMA expression include breast, lung, colorectal, and renal cell carcinoma. Thus any composition containing a radiohybrid described herein having a PSMA binding moiety can be used in the diagnosis, imaging or treatment of a cancer having PSMA expression.

Preferred indications are the detection or staging of cancer, such as, but not limited high grade gliomas, lung cancer and especially prostate cancer and metastasized prostate cancer, the detection of metastatic disease in patients with primary prostate cancer of intermediate-risk to high-risk, and the detection of metastatic sites, even at low serum PSA values in patients with biochemically recurrent prostate cancer. Another preferred indication is the imaging and visualization of neoangiogensis.

In terms of medical indications to be subjected to therapy, especially radiotherapy, cancer is a preferred indication. Prostate cancer is a particularly preferred indication.

In a further aspect, the present invention provides a composition comprising a conjugate or compound of the radiohybrids as defined herein above for use in a method of diagnosing and/or staging cancer, preferably prostate cancer.

Example 1

The Gallium chelate of Compound rh-PSMA-7.3 was prepared as previously described in WO2019/020831 and EP19154500.3:

rhPSMA-7.3 (D-Dap, (S)-DOTA-GA):

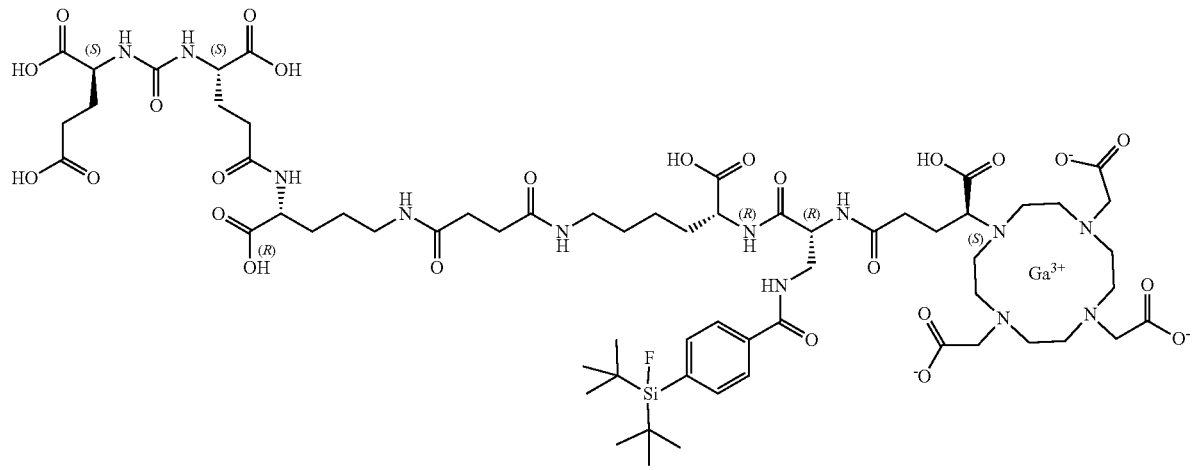

Fmoc-D-Dap(Dde)-OH (2.0 eq.) was pre-activated in a mixture of HOAt (2.0 eq.), TBTU (2.0 eq.) and 2,4,6-trimethylpyridine (6.7 eq.) in DMF and added to the resin-bound peptide for 2.5 h. Orthogonal Dde-deprotection was done using imidazole and hydroxylamine hydrochloride dissolved in a mixture of NMP and DMF for 3 h. SiFA-BA (1.5 eq.) was reacted with the free amine of the side chain with HOAt (1.5 eq.), TBTU (1.5 eq.) and DIPEA (4.5 eq.), as activation reagents in DMF for 2 h. After Fmoc-deprotection (20% piperidine in DMF (v/v, 8 mL/g resin) for 5 min and subsequently for 15 min, afterwards, the resin was washed thoroughly with DMF (8×5 mL/g resin)), (R)-DOTA-GA(tBu)$_4$ (2.0 eq.) was conjugated with HOAT (2.0 eq.), TBTU (2.0 eq.) and 2,4,6-trimethylpyridine (6.7 eq.) in DMF for 2.5 h. Cleavage from the resin with simultaneous deprotection of acid labile protecting groups was performed in TFA (The fully protected resin-bound peptide was dissolved in a mixture of TFA/TIPS/water (v/v/v; 95/2.5/2.5) and shaken for 30 min. The solution was filtered off and the resin was treated in the same way for another 30 min. Both filtrates were combined, stirred for additional 5 h and concentrated under a stream of nitrogen. After dissolving the residue in a mixture of tert-butanol and water and subsequent lyophilisation the crude peptide was obtained). $^{nat}$Ga-complexation of the peptide was carried out. The peptide (1.0 eq.) was dissolved in a 3:1 (v/v) mixture of tBuOH in H$_2$O and an aqueous solution of Ga(NO$_3$)$_3$ (3.5 eq.) was added. After heating the resulting mixture for 30 min at 75° C. the peptide was purified by RP-HPLC.

$^{18}$F-Labeling

Aqueous $^{18}$F$^-$ was passed through a SAX cartridge (Sep-Pak Accell Plus QMA Carbonate light), which was preconditioned with 10 mL of water. After drying with 10 mL of air, water was removed, by rinsing the cartridge with 10 mL of anhydrous acetonitrile followed by 20 mL of air. $^{18}$F was eluted with 100 μmol of [K$^+$⊂2.2.2]OH$^-$ dissolved in 500 μL of anhydrous acetonitrile. Before labelling, 30 μmol of oxalic acid in anhydrous acetonitrile (1 M, 30 μL) were added. This mixture was used as a whole or aliquot for fluorination of 10-25 nmol of PSMA-SiFA (1 mM in anhydrous DMSO). The resulting reaction mixture was incubated for 5 minutes at room temperature. For purification of the tracer, a Sep-Pak C18 light cartridge, preconditioned with 10 mL EtOH, followed by 10 mL of H$_2$O was used. The labelling mixture was diluted with 9 mL PBS (pH 3) and passed through the cartridge followed by 10 mL of H$_2$O. The peptide was eluted with 500 μL of a 4:1 mixture (v/v) of EtOH in water. Radiochemical purity of the labelled compound was determined by radio RP-HPLC and radio-TLC (Silica gel 60 RP-$^{18}$F$_{254}$s, mobile phase: 3:2 mixture (v/v) of MeCN in H$_2$O supplemented with 10% of 2 M aqueous NaOAc and 1% of TFA).

Alternatively [$^{18}$F]rhPSMA-7.3 may be prepared on an automated synthesis module by isotopic exchange between [$^{18}$F]fluoride ion and [$^{18}$F]rhPSMA-7.3 as follows:

Fluorine-18 in the form of [$^{18}$F]fluoride ion is prepared from $^{18}$O(p,n)$^{18}$F nuclear reaction in a cyclotron by irradiation of $^{18}$O-enriched water with protons. [$^{18}$F]fluoride is first immobilised on an ion exchange resin to allow for recovery of $^{18}$O-enriched water. [$^{18}$F]fluoride is then eluted with a solution of Cryptand 222 and potassium carbonate in acetonitrile and water. The eluate is transferred into the reaction vessel and evaporated by heating under a flow of nitrogen. [$^{19}$F]rhPSMA-7.3 in solution of DMSO, acetonitrile and acetic acid is added to the reaction vessel and reacted with nucleophilic [$^{18}$F]fluoride for at least 1 min to form [$^{18}$F]rhPSMA-7.3. The crude solution of [$^{18}$F]rhPSMA-7.3 is diluted with water and purified by hydrophobic solid phase extraction. Impurities are removed by washing the cartridge with water. [$^{18}$F]rhPSMA-7.3 is eluted with an ethanol-water solution and formulated by diluting with an isotonic formulation buffer. The formulated solution is sterilised by filtration through a 0.2 μm filter.

Dilution if applicable is performed using an isotonic sodium chloride solution for injection.

Batches of material were prepared in either a citrate buffer made from sodium citrate+HCl or a citrate buffer made from citric Acid+NaOH.

Radio-stability was measured in phosphate and citrate buffers at various pH levels to compare the level of the correct 18F—Si compound and the decomposed free 18F:

| Sample # | $^{18}$F-rhPSMA in 50% ethanol | diluent | pH t = 0 h | TLC t = 0 h [$^{18}$F][$^{nat}$Ga]-rhPSMA-7.3 [%] | [$^{18}$F] Fluoride [%] | TLC t = 6 h [$^{18}$F][$^{nat}$Ga]-rhPSMA-7.3 [%] | [$^{18}$F] Fluoride [%] | HPLC G-49 t = 6 h Impurity @ 2.6 min [Area] | Δ[$^{18}$F] Fluoride [%] (t6h-t0) |
|---|---|---|---|---|---|---|---|---|---|
| 1 | 0.5 mL | none | 8.0 | 96.1 | 3.9 | 93.2 | 6.8 | 0.406 | 2.9 |
| 2 | 0.1 mL | 0.6 mL 0.23M phosphate buffer pH 6.0 | 6.5 | 98.1 | 1.9 | 96.8 | 3.1 | 0.314 | 1.2 |
| 3 | 0.1 mL | 0.6 mL phosphate buffer pH 7.0 | 7.5 | 97.7 | 2.3 | 96.25 | 3.75 | 0.138 | 1.5 |
| 4 | 0.1 mL | 0.6 mL 0.2M citrate buffer pH 5.0 | 5.0 | 97.7 | 2.3 | 97.3 | 2.7 | 0.119 | 0.4 |
| 5 | 0.1 mL | 0.6 mL 0.2M citrate buffer pH 8.0 | 6.0 | 98.4 | 1.6 | 97.5 | 2.5 | 0.191 | 0.9 |
| 6 | 0.1 mL | 0.6 mL 0.2M citrate buffer pH 7.0 | 7.5 | 97.8 | 2.2 | 95.7 | 4.3 | 0.084 | 2.1 |

The most stable formulation was pH 5.0 in citrate buffer. Increasing the pH in citrate buffer gave an increase in the amount of free 18F (which is presumably displaced by OH). At the same pH (6.0) phosphate buffer gives a less stable product than citrate buffer.

Radiochemical and chemical purity was assessed for various formulations containing citrate buffer or citrate buffered saline (Table 1).

TABLE 1

Radiochemical and chemical purity of various formulations

| Entry | Radioactivity concentration at EOS (mCi/mL) | Formulation | pH | Radiochemical purity by HPLC (%) T0 | Radiochemical purity by HPLC (%) T = 10 h | [18F]fluoride impurity by TLC (%) T0 | [18F]fluoride impurity by TLC (%) T = 10 h | Chemical purity (%) T0 | Chemical purity (%) T = 10 h |
|---|---|---|---|---|---|---|---|---|---|
| 1 | 27 | 100 mM citrate buffer, 5% ethanol | 5.0 | 98.6 | 98.7 | 1.6 | 1.5 | 98.6 | 96.9 |
| 2 | 26 | 100 mM citrate buffer, 5% ethanol | 5.5 | 99.5 | 99.5 | 1.9 | 2.5 | 99.1 | 96.7 |
| 3 | 12 | 100 mM citrate buffer, 5% ethanol | 6.0 | 99.5 | >99.5 | 1.2 | 1.5 | N/A | N/A |
| 4 | 51 | 100 mM citrate buffer, 5% ethanol | 6.5 | 99.5 | >99.5 | <1.0 | 1.4 | N/A | N/A |
| 5 | 56 | 10 mM citrate buffered saline, 5% ethanol | 5.0 | 98.7 | 98.9 | 1.2 | 1.1 | 98.3 | 96.7 |
| 6 | 34 | 10 mM citrate buffered saline, 5% ethanol | 6.0 | 99.3 | 99.6 | 1.0 | 1.9 | 99.6 | 98.8 |

Upon dilution with sodium chloride solution for injection (0.9% w/v), the pH of the formulation (entry 5, Table 1: 10 mM citrate buffered saline, 5% ethanol) is maintained:

TABLE 2

Formulation after dilution of Table 1, entry 5 with sodium chloride solution

| Entry | dilution factor | citrate buffer (mM) | Sodium chloride (mg/mL) | Ethanol (mg/mL) | pH |
|---|---|---|---|---|---|
| 1 | 1 | 10 | 7.2 | 50.0 | 5.0 |
| 2 | 1.8 | 5.6 | 8.0 | 27.8 | 5.0 |
| 3 | 3 | 3.3 | 8.4 | 16.7 | 5.0 |
| 4 | 5 | 2.0 | 8.6 | 10.0 | 5.0 |
| 5 | 7 | 1.4 | 8.7 | 7.1 | 5.1 |
| 6 | 9.4 | 1.1 | 8.8 | 5.3 | 5.1 |

The invention claimed is:

1. A pharmaceutical composition comprising a radiohybrid agent containing a silicon-fluoride group and a chelating group, wherein either the fluorine of the silicon-fluoride group is $^{18}F$ or the chelating group contains a chelated radioactive metal, wherein the radiohybrid agent is:

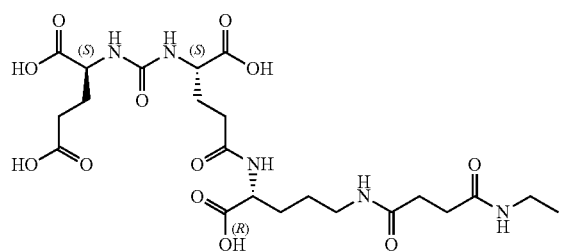

-continued

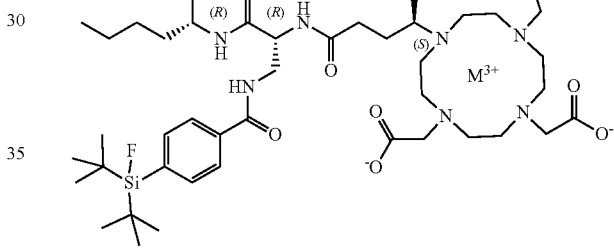

or an isomer or salt thereof, wherein $M^{3+}$ is a chelated radioactive or non-radioactive metal, and wherein the composition has a pH of 4.0-6.0 and further comprises:
 a) 0.1-200 mM citrate buffer; and
 b) 1-100 mg/mL ethanol; and
 c) 5-10 mg/mL sodium chloride.

2. The pharmaceutical composition as defined in claim 1 comprising 1-15 mM citrate buffer.

3. The pharmaceutical composition as defined in claim 1 comprising 5-50 mg/mL ethanol.

4. The pharmaceutical composition as defined in claim 1 that has a pH of 4.5 to 5.5.

5. The pharmaceutical composition as defined in claim 1 wherein the citrate buffer is prepared from citric acid and sodium hydroxide, or sodium citrate and hydrochloric acid.

6. The pharmaceutical composition as defined in claim 5, wherein 1-3 mg/mL citric acid and 0.5-1.0 mg/mL sodium hydroxide are used to prepare the citrate buffer.

7. The pharmaceutical composition as defined in claim 1 wherein $M^{3+}$ is a chelated radioactive metal and the fluorine is $^{19}F$.

8. The pharmaceutical composition as defined in claim 1 wherein the chelated metal is selected from the cations of: Sc, Cu, Ga, Y, In, Tb, Ho, Lu, Re, Pb, Bi, Ac, Th or Er.

9. The pharmaceutical composition as defined in claim 1 wherein the fluorine is $^{18}F$ and $M^{3+}$ is a chelated non-radioactive metal.

10. The pharmaceutical composition as defined in claim 8 wherein the chelated metal cation is radioactive and is a positron emitting isotope.

11. The pharmaceutical composition as defined in claim 1 that has an end of synthesis (EOS) radioactive concentration (RAC) of 5-200 mCi/mL.

12. The pharmaceutical composition as defined in claim 1 comprising 10 mM citrate buffer, 50 mg/mL ethanol, 7.2 mg/mL sodium chloride, and that is pH 5.

13. The pharmaceutical composition as defined in claim 1, which is diluted with sodium chloride solution prior to administration.

14. The pharmaceutical composition as defined in claim 13 comprising 1.1 mM (±10%) citrate buffer, 5.3 mg/mL (±10%) ethanol, 8.8 mg/mL (±10%) sodium chloride, and which has a pH of 4.5 to 5.5.

15. A method of imaging and/or diagnosing cancer comprising administering a composition according to claim 1 to a patient in need thereof.

16. A method of diagnosis, imaging or prevention of neoangiogenesis/angiogenesis comprising administering a composition according to claim 1 to a patient in need thereof.

17. A method of imaging and/or diagnosing cancer comprising administering a composition according to claim 1 to a patient in need thereof wherein the cancer is prostate, breast, lung, colorectal or renal cell carcinoma.

18. A method of producing a composition as defined claimed in claim 1, the method comprising:
preparing a formulation comprising the radiohybrid agent, the citrate buffer, and the ethanol, wherein the formulation has a pH of 4.0-6.0 and a citrate concentration of at least 10 mM, and
diluting the citrate concentration of the formulation with sodium chloride.

19. The pharmaceutical composition as defined in claim 1 wherein the metal is 68 Ga.

20. The pharmaceutical composition as defined in claim 1 wherein the fluorine is $^{18}$F and the metal is $^{68}$Ga.

* * * * *